(12) United States Patent
Foote et al.

(10) Patent No.: US 10,029,058 B2
(45) Date of Patent: Jul. 24, 2018

(54) VENT ARRANGEMENT FOR RESPIRATORY MASK

(75) Inventors: Roger Mervyn Lloyd Foote, Eastwood (AU); Ronald James Huby, North Epping (AU); Muditha Pradeep Dantanarayana, Cherrybrook (AU); Damien Julian Mazzone, Concord West (AU); Dion Charles Chewe Martin, Concord (AU); Jeffrey Peter Armitstead, North Sydney (AU); Justin John Formica, Voyager Point (AU); Zhuo Ran Tang, Maroubra (AU); Lance Steven Cohen, Neutral Bay (AU); James William Charles Vandyke, Glebe (AU); David Brent Sears, Woodland Hills, CA (US); Aleksandr S. Nagorny, Canoga Park, CA (US); Joe Sampietro, Tarzana, CA (US); Steven Paul Farrugia, Lugarno (AU)

(73) Assignee: ResMed Limited (AU)

( * ) Notice: Subject to any disclaimer, the term of this patent is extended or adjusted under 35 U.S.C. 154(b) by 813 days.

(21) Appl. No.: 14/342,972

(22) PCT Filed: Sep. 13, 2012

(86) PCT No.: PCT/US2012/055148
§ 371 (c)(1),
(2), (4) Date: Mar. 5, 2014

(87) PCT Pub. No.: WO2013/040198
PCT Pub. Date: Mar. 21, 2013

(65) Prior Publication Data
US 2014/0283831 A1   Sep. 25, 2014

Related U.S. Application Data

(60) Provisional application No. 61/558,158, filed on Nov. 10, 2011, provisional application No. 61/534,044, filed on Sep. 13, 2011.

(51) Int. Cl.
*A61M 16/00* (2006.01)
*A61M 16/06* (2006.01)
(Continued)

(52) U.S. Cl.
CPC .......... *A61M 16/009* (2013.01); *A61B 5/087* (2013.01); *A61B 5/091* (2013.01); *A61B 5/4809* (2013.01);
(Continued)

(58) Field of Classification Search
CPC .... A61M 2202/0225; A61M 2230/202; A61M 2202/0085; A61M 2230/005;
(Continued)

(56) References Cited

U.S. PATENT DOCUMENTS 1,407,216 A    2/1922   Potter
3,101,736 A    8/1963   Egger
(Continued)

FOREIGN PATENT DOCUMENTS

CN    1886167 A    12/2006
EP    0266963 A2    5/1988
(Continued)

OTHER PUBLICATIONS

European Search Report for Application No. EP12831096 dated Feb. 17, 2015.
(Continued)

*Primary Examiner* — Bradley Philips
(74) *Attorney, Agent, or Firm* — Lerner, David, Littenberg, Krumholz & Mentlik, LLP

(57) ABSTRACT

A control system (706) provides automated control of gas washout of a patient interface, such as a mask or nasal prongs. A gas washout vent assembly (60) of the system may include a variable exhaust area such as one defined by overlapping apertures of the assembly or a conduit having a
(Continued)

variable gas passage channel. The vent assembly may be formed by nested structures, such as conic or cylindrical members, each having an opening of the overlapping apertures. The vent assembly may be attached substantially near or included with the patient interface. An actuator of the assembly, such as a solenoid or voice coil, manipulates an aperture of the vent assembly. The actuator may be configured for control by a controller to change the exhaust area of the vent assembly based on various methodologies including, for example, sleep detection, disordered breathing event detection, rebreathing volume calculation and/or leak detection.

49 Claims, 32 Drawing Sheets

(51) Int. Cl.
    *A61M 16/20*     (2006.01)
    *A61M 16/10*     (2006.01)
    *A61B 5/087*     (2006.01)
    *A61B 5/091*     (2006.01)
    *A61B 5/00*     (2006.01)
    *A61M 16/08*     (2006.01)

(52) U.S. Cl.
    CPC .......... *A61B 5/4812* (2013.01); *A61B 5/4818* (2013.01); *A61B 5/4836* (2013.01); *A61M 16/0051* (2013.01); *A61M 16/0069* (2014.02); *A61M 16/026* (2017.08); *A61M 16/06* (2013.01); *A61M 16/0666* (2013.01); *A61M 16/1095* (2014.02); *A61M 16/20* (2013.01); *A61M 16/202* (2014.02); *A61M 16/0045* (2013.01); *A61M 16/0816* (2013.01); *A61M 16/0875* (2013.01); *A61M 2016/003* (2013.01); *A61M 2016/0027* (2013.01); *A61M 2202/0225* (2013.01); *A61M 2205/15* (2013.01); *A61M 2205/3331* (2013.01); *A61M 2205/3334* (2013.01); *A61M 2205/3368* (2013.01); *A61M 2205/42* (2013.01); *A61M 2205/50* (2013.01); *A61M 2230/202* (2013.01)

(58) Field of Classification Search
    CPC .......... A61M 16/0045; A61M 16/0051; A61M 16/0069; A61M 16/009; A61M 16/06; A61M 16/0666; A61M 16/0816; A61M 16/0875; A61M 16/1095
    See application file for complete search history.

(56) References Cited

U.S. PATENT DOCUMENTS

| | | | |
|---|---|---|---|
| 3,431,931 A | | 3/1969 | Cupp |
| 3,431,932 A | | 3/1969 | Cupp |
| 3,985,334 A | | 10/1976 | Domyan |
| 4,094,492 A | | 6/1978 | Beeman et al. |
| 4,796,619 A | | 1/1989 | Walther |
| 4,842,245 A | | 6/1989 | Kelsey |
| 5,193,529 A | | 3/1993 | Labaere |
| 5,370,154 A | | 12/1994 | Greer |
| 5,568,910 A | | 10/1996 | Koehler et al. |
| 5,918,597 A | | 7/1999 | Jones et al. |
| 6,006,748 A | * | 12/1999 | Hollis ................ A61M 16/208 128/204.18 |
| 6,182,656 B1 | * | 2/2001 | Sagiv ................ A61H 31/02 128/202.12 |
| 6,446,629 B1 | * | 9/2002 | Takaki ................ A61M 16/0096 128/204.18 |
| 6,543,449 B1 | * | 4/2003 | Woodring ............ A61M 16/00 128/204.18 |
| 6,581,594 B1 | | 6/2003 | Drew et al. |
| 6,581,596 B1 | * | 6/2003 | Truitt ................ A61M 16/0006 128/204.18 |
| 6,659,101 B2 | | 12/2003 | Berthon-Jones |
| 6,708,690 B1 | * | 3/2004 | Hete ................ A61M 16/0096 128/204.18 |
| 6,722,359 B2 | | 4/2004 | Chalvignac |
| 6,752,150 B1 | * | 6/2004 | Remmers ............ A61M 16/00 128/204.18 |
| 7,073,501 B2 | * | 7/2006 | Remmers ............ A61M 16/00 128/204.18 |
| 8,251,066 B1 | | 8/2012 | Ho et al. |
| 8,366,645 B1 | * | 2/2013 | Belalcazar .......... A61H 31/006 601/41 |
| 2003/0000532 A1 | | 1/2003 | Bowman et al. |
| 2003/0075176 A1 | | 4/2003 | Fukunaga et al. |
| 2004/0007232 A1 | | 1/2004 | Rochat |
| 2004/0144383 A1 | * | 7/2004 | Thomas ............ A61M 16/0045 128/204.18 |
| 2005/0126648 A1 | | 6/2005 | Vu et al. |
| 2005/0172967 A1 | | 8/2005 | McAuliffe et al. |
| 2006/0060200 A1 | | 3/2006 | Ho et al. |
| 2006/0060245 A1 | | 3/2006 | Baumgarten et al. |
| 2006/0090762 A1 | | 5/2006 | Hegde et al. |
| 2007/0033793 A1 | | 2/2007 | Schlosser et al. |
| 2008/0000472 A1 | | 1/2008 | Wall |
| 2008/0047560 A1 | | 2/2008 | Veliss et al. |
| 2008/0060656 A1 | * | 3/2008 | Isaza ................ A61M 16/0468 128/207.16 |
| 2008/0169443 A1 | | 7/2008 | Loloff |
| 2008/0283060 A1 | | 11/2008 | Bassin |
| 2008/0302364 A1 | * | 12/2008 | Garde ................ A61M 16/0045 128/204.23 |
| 2009/0260631 A1 | | 10/2009 | Aubonnet et al. |
| 2010/0043796 A1 | | 2/2010 | Meynink et al. |
| 2010/0258123 A1 | | 10/2010 | Somaiya et al. |
| 2010/0307500 A1 | | 12/2010 | Armitstead |
| 2010/0318039 A1 | | 12/2010 | Hall et al. |
| 2010/0326447 A1 | | 12/2010 | Loomas et al. |
| 2011/0126832 A1 | | 6/2011 | Winter et al. |
| 2011/0126834 A1 | | 6/2011 | Winter et al. |
| 2011/0127339 A1 | | 6/2011 | Li et al. |
| 2013/0102917 A1 | * | 4/2013 | Colbaugh ............ A61M 16/00 600/533 |
| 2015/0136137 A1 | | 5/2015 | Bugamelli et al. |

FOREIGN PATENT DOCUMENTS

| | | |
|---|---|---|
| EP | 1197238 A2 | 4/2002 |
| EP | 1327458 A1 | 7/2003 |
| EP | 1923088 A2 | 5/2008 |
| FR | 2 784 587 A1 | 4/2000 |
| JP | 2003511160 A | 3/2003 |
| JP | 2006513004 A | 4/2006 |
| JP | 2007512047 A | 5/2007 |
| WO | 9014121 A1 | 11/1990 |
| WO | 0126722 A1 | 4/2001 |
| WO | 2002/053217 | 7/2002 |
| WO | 2004069317 A1 | 8/2004 |
| WO | 2005047797 A2 | 5/2005 |
| WO | 2005/051468 | 6/2005 |
| WO | 2005051468 A1 | 6/2005 |
| WO | 2006/102708 A1 | 10/2006 |
| WO | 2008/055308 | 5/2008 |
| WO | 2011006199 A1 | 1/2011 |
| WO | 2011144541 A1 | 11/2011 |
| WO | 2012012835 A2 | 2/2012 |
| WO | 2013040198 A2 | 3/2013 |

OTHER PUBLICATIONS

International Search Report and Written Opinion for Application No. PCT/US2012/055148 dated Feb. 15, 2013.
U.S. Appl. No. 61/226,069, filed Jul. 16, 2009.
U.S. Appl. No. 61/369,247, filed Jul. 30, 2010.

(56) References Cited

OTHER PUBLICATIONS

Partial European Search Report for Application No. 13183779.1 dated Dec. 11, 2013.
Extended European Search Report for Application No. 13183779 dated Mar. 31, 2014.
Further Examination Report for NZ729631 dated Feb. 19, 2018.

* cited by examiner

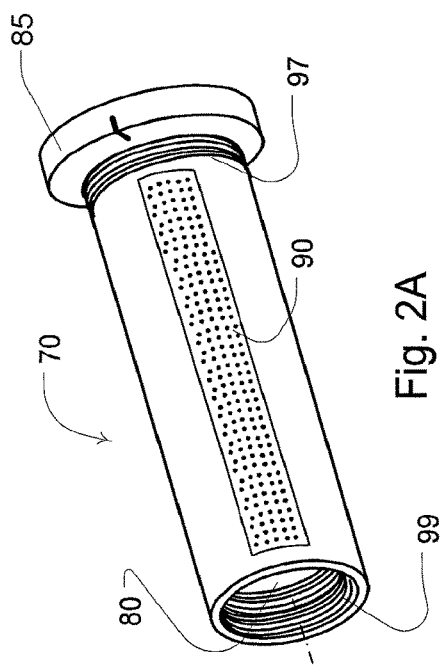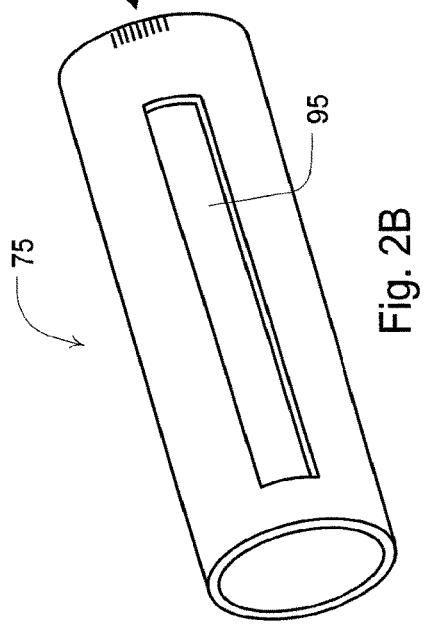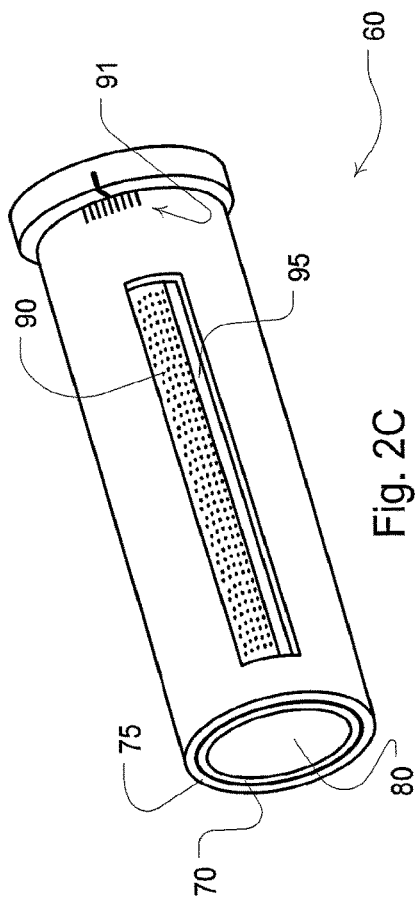

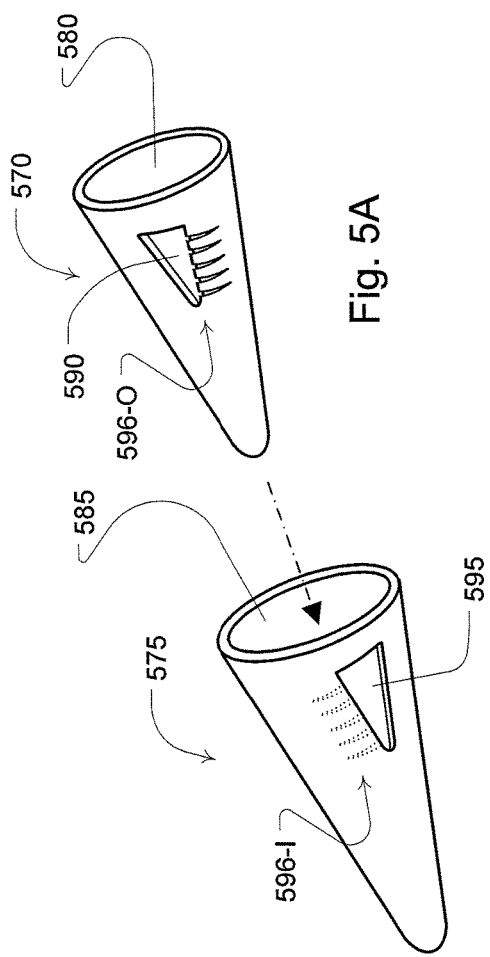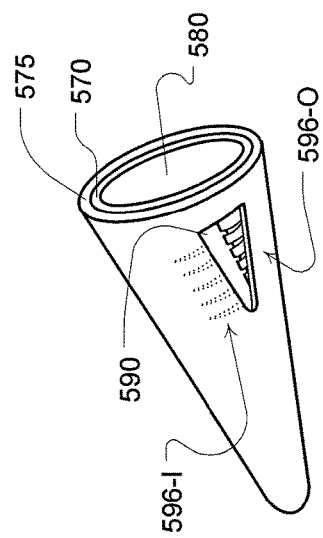

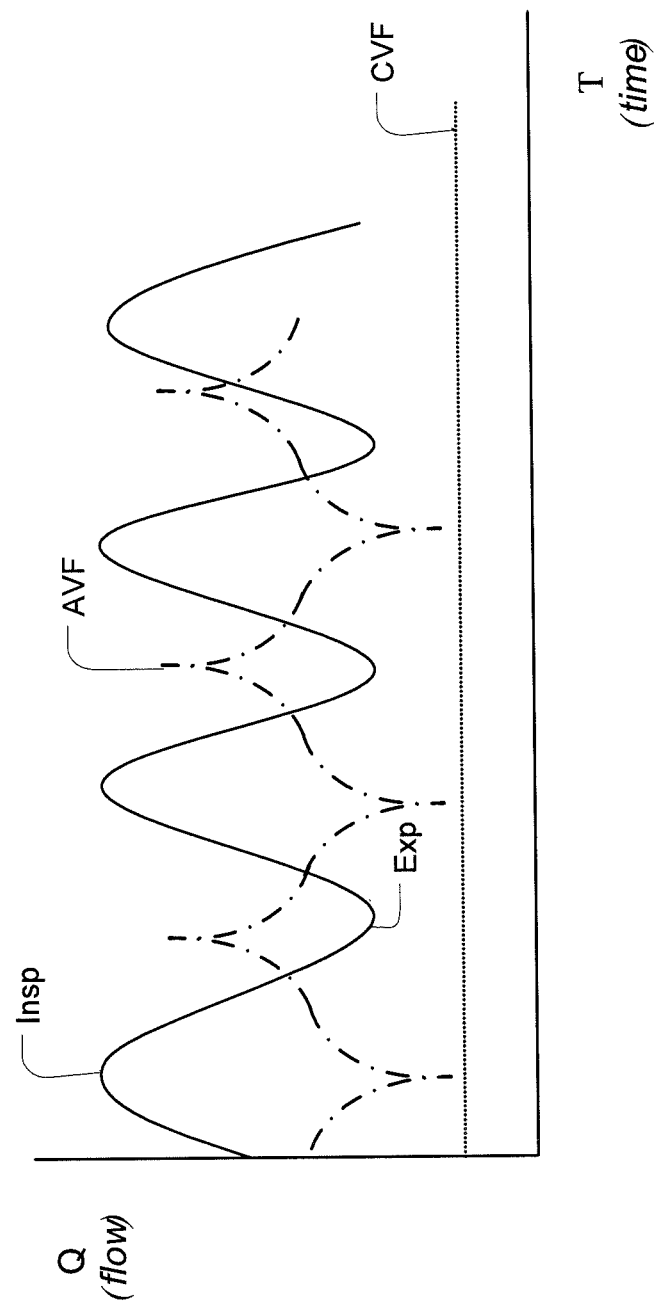

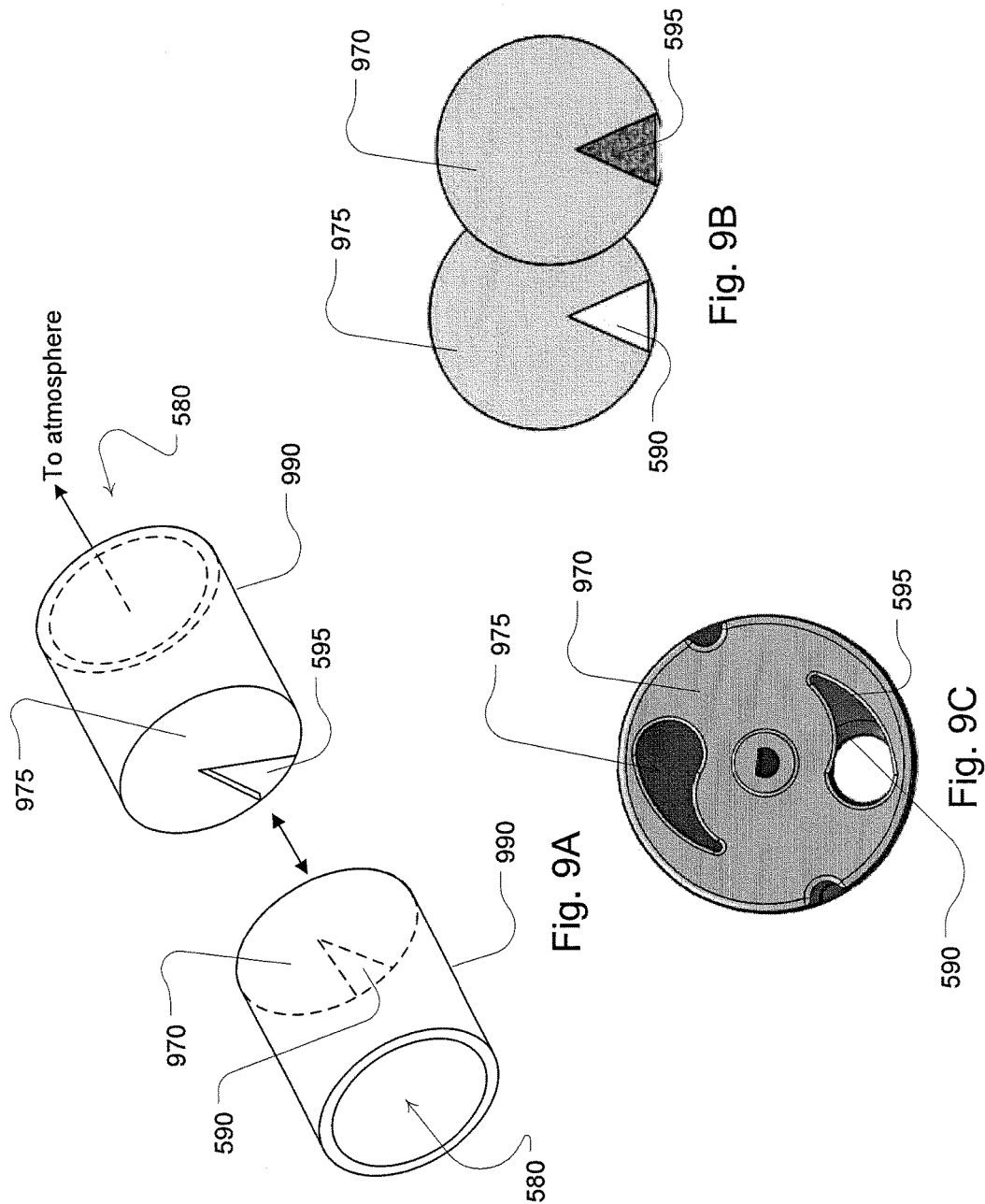

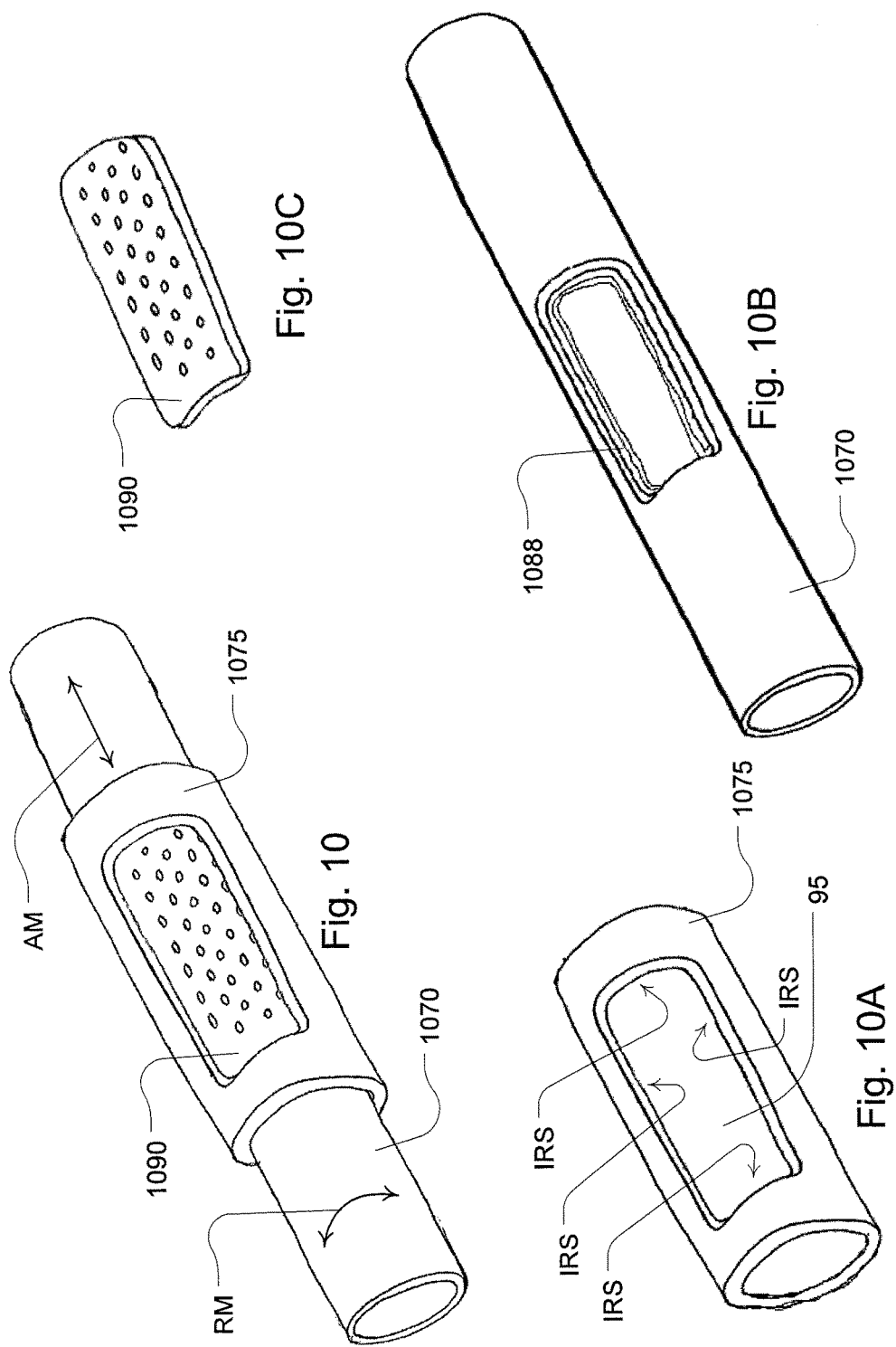

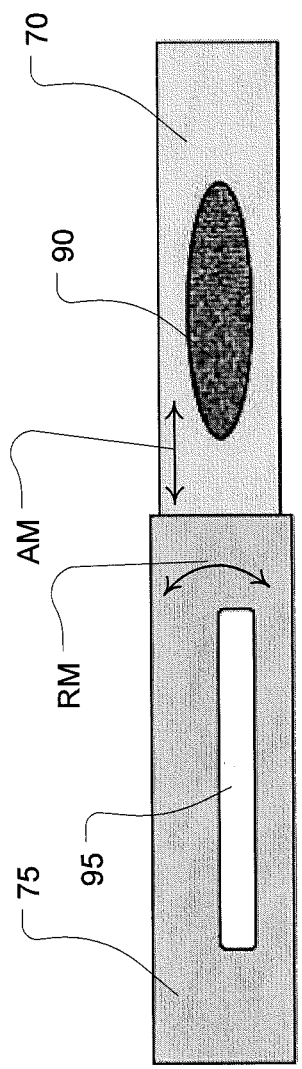

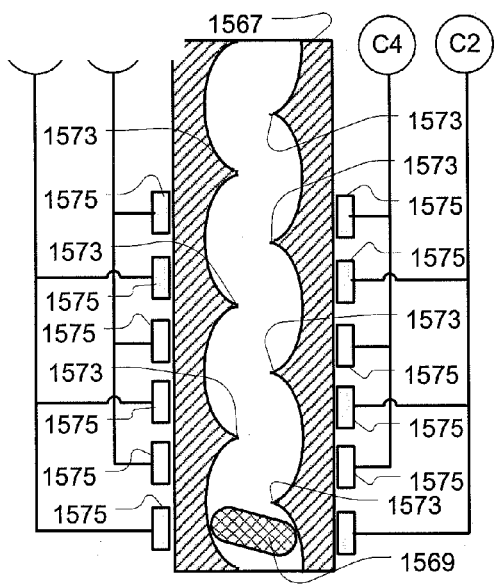
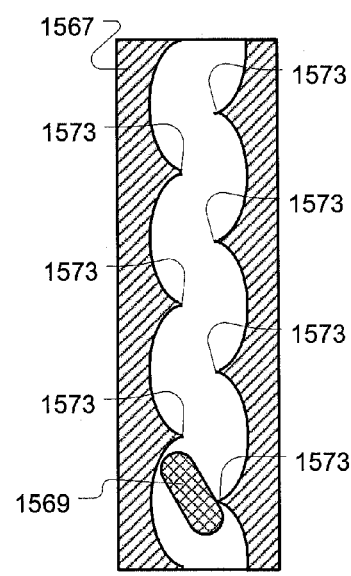
Fig. 15A
Fig. 15B
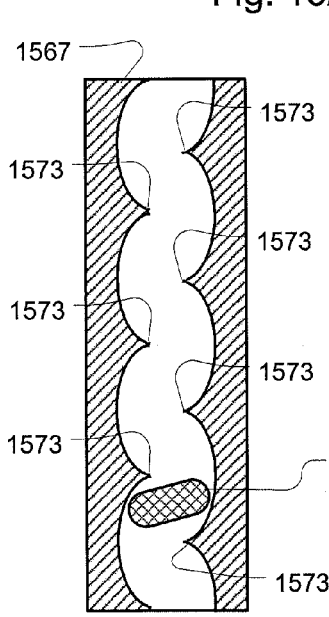
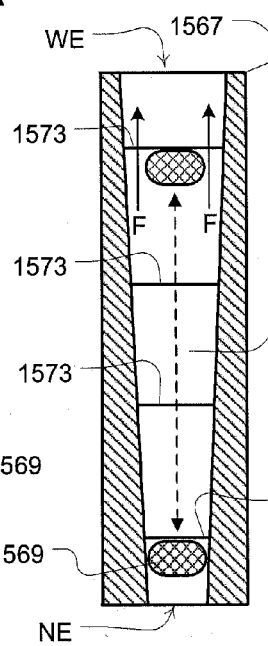
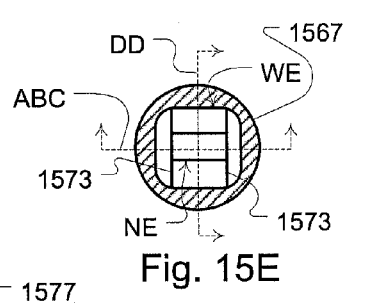
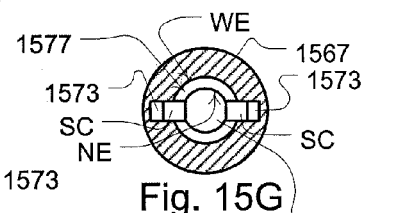
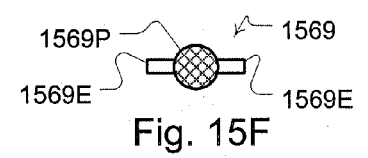
Fig. 15C
Fig. 15D
Fig. 15E
Fig. 15G
Fig. 15F

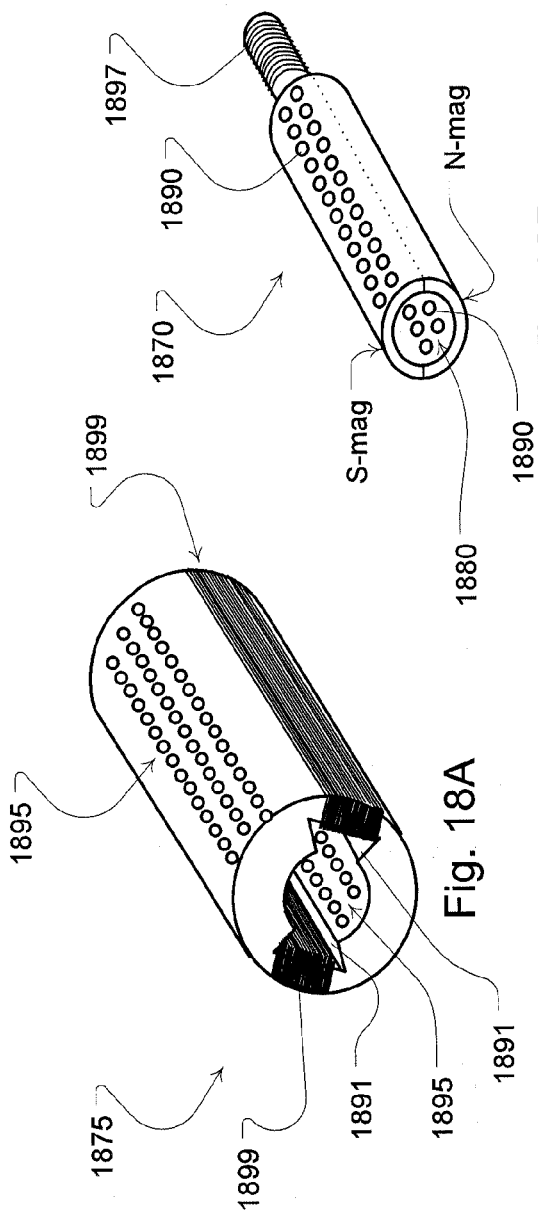

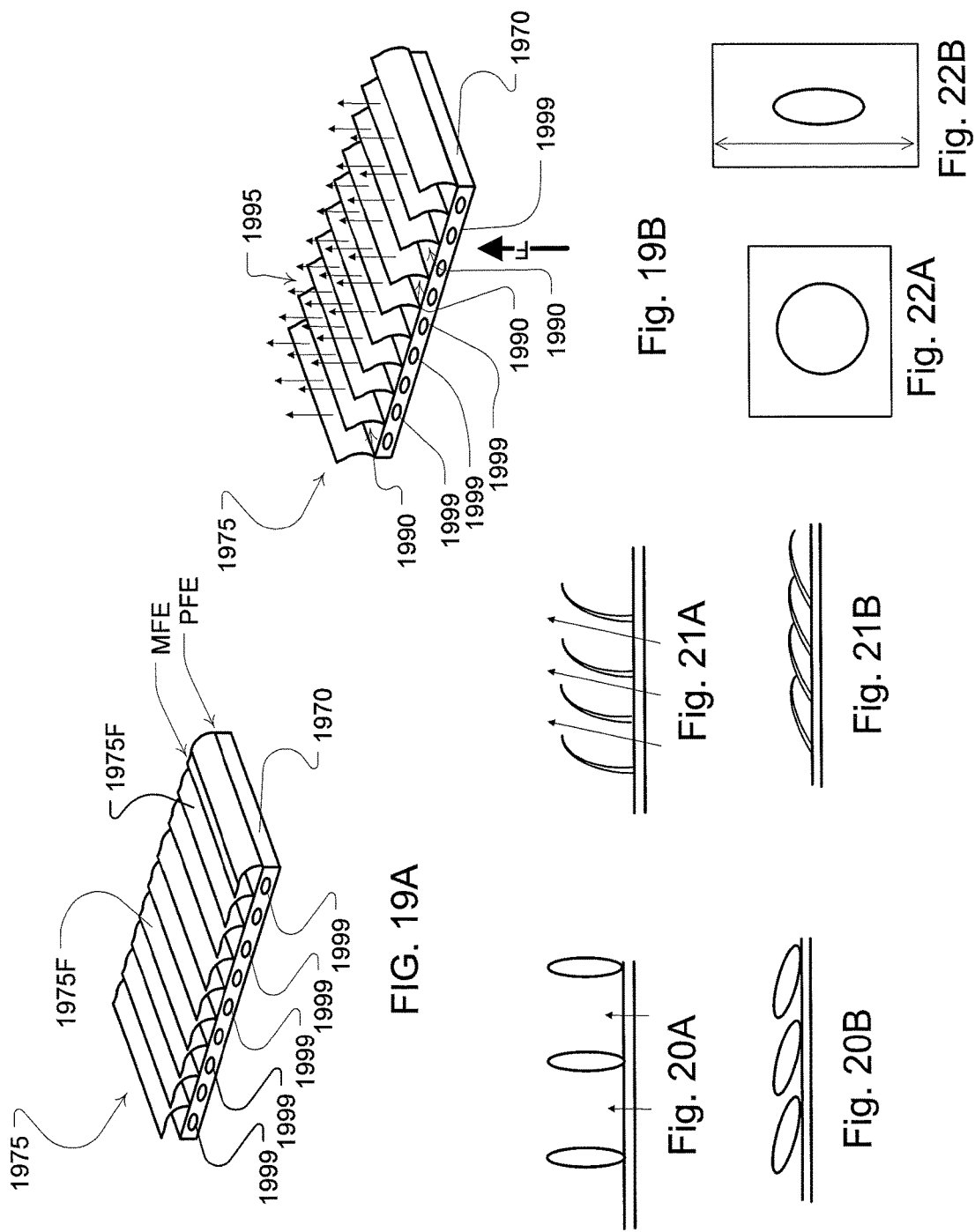

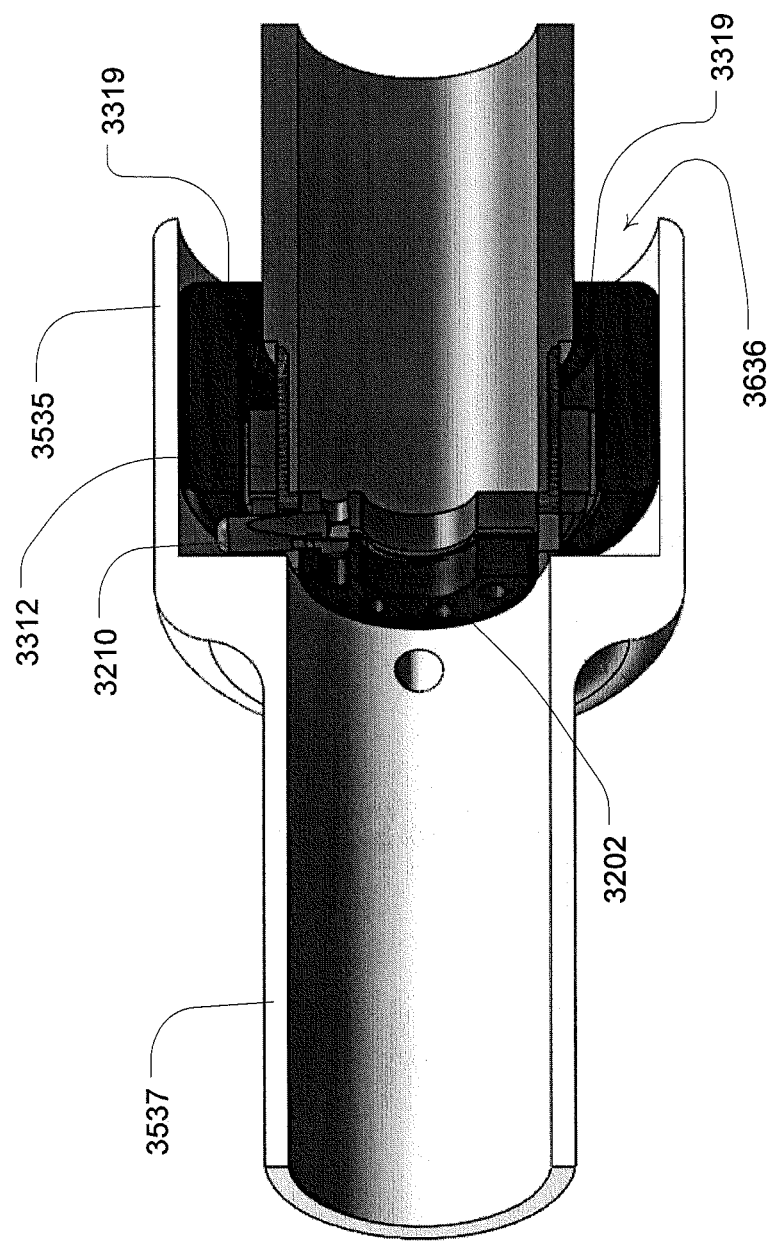

VENT ARRANGEMENT FOR RESPIRATORY MASK

CROSS REFERENCE TO RELATED APPLICATIONS

This application claims the benefit of the filing dates of U.S. Provisional Patent Application Nos. 61/534,044 filed Sep. 13, 2011, and 61/558,158 filed Nov. 10, 2011, the disclosures of which are hereby incorporated herein by reference.

FIELD OF THE TECHNOLOGY

The present technology relates to conduits for a respiratory treatment apparatus such as a vent arrangement for a mask assembly that may be implemented for a respiratory pressure treatment including, for example, Non-invasive Positive Pressure Ventilation (NPPV) and continuous positive airway pressure (CPAP) therapy of sleep disordered breathing (SDB) conditions such as obstructive sleep apnea (OSA).

BACKGROUND OF THE TECHNOLOGY

Treatment of sleep disordered breathing (SDB), such as obstructive sleep apnea (OSA), by a respiratory treatment apparatus such as a continuous positive airway pressure (CPAP) flow generator system involves a delivery of air (or other breathable gas) at pressures above atmospheric pressure to the airways of a human or other mammalian patient via a conduit and/or a mask. Typically, the mask fits over the mouth and/or nose of the patient, or it may be an under-nose style such as a nasal pillows or nasal cushion style mask. Pressurized air flows to the mask and to the airways of the patient via the nose and/or mouth. As the patient exhales, carbon dioxide gas may collect in the mask and breathing circuit. A washout vent in the mask or conduit may be implemented to refresh the gas in the circuit by virtue of the positive pressure maintained within the circuit. By providing adequate renewal of gas at the patient-end of the circuit, the patient's exhaled gas can be expelled from the mask to atmosphere.

The washout vent is normally located in the mask or substantially near the mask in a gas delivery conduit coupled to the mask. The washout of gas through the vent to the atmosphere removes exhaled gases to prevent carbon dioxide build-up. "Rebreathing" of exhaled carbon dioxide may be a health risk to the mask wearer. Rebreathing may occur of the contents of any circuit volume on the patient side of the vent (the circuit "deadspace"). This is most problematic for those patients whose tidal volume is not substantially larger than this "deadspace". Rebreathing may also occur of any exhaled volume that extends beyond the vent back up the circuit away from the patient. Any of this exhaled gas that remains at the start of the next inspiration will represent a proportion of rebreathing. Whether such a residual exhaled volume exists or not depends on the degree of venting, the patient's tidal volume, and the breath pattern. Breathing patterns more likely to foster rebreathing are those with substantial tidal volumes and minimal end-expiratory pause (e.g., obstructive lung mechanics such as in COPD). Adequate gas washout may be achieved by selecting a vent size and configuration that allows a minimum safe washout flow at a low operating CPAP pressure, which typically can be as low as 4 cm $H_2O$ for adults and 2 cm $H_2O$ for children.

WO 2006/102708 describes an air delivery system with a vent valve that is controlled to maintain a substantially constant air flow in the air delivery conduit and the air flow generator.

WO2005/051468 describes a vent assembly for use with a mask assembly. The vent assembly includes a first vent, a second vent and a selector to switch the flow of exhaled gas from a patient between the first and second vents.

There is a need for a gas washout vent arrangement which allows for adequate venting of carbon dioxide while permitting efficient air delivery to the patient.

SUMMARY OF THE TECHNOLOGY

One aspect of the present technology relates to a washout vent arrangement for respiratory mask apparatus which incorporates a variable effective venting area or aperture(s).

Further aspects of the present technology relate to an air delivery apparatus incorporating a gas vent arrangement, and to apparatus, systems and methods for controlling variable venting of gases.

In one form, the technology provides a vent arrangement for venting of gases from a respiratory treatment apparatus, including a vent member having a vent portion, and a vent cover member for controllably covering a variable area of said vent portion.

Some aspects of the present technology involve an apparatus for automated control of gas washout of a patient interface of a respiratory treatment apparatus. The apparatus may include a vent assembly having a variable exhaust area defined by apertures of the vent assembly, the vent assembly being associated with a patient interface to vent expiratory gas; and an actuator to manipulate an aperture of the vent assembly. Optionally, the apparatus may also include a controller including a processor, the controller coupled with the actuator, wherein the controller may be configured to operate the actuator to change the exhaust area of the vent assembly. Optionally, the exhaust area may be defined by overlapping apertures.

In some such cases, the processor may be configured to switch between a treatment setting for the variable exhaust area and the comfort setting for the variable exhaust area. The processor may be configured with a user interface for input of comfort settings including a setting for the variable exhaust area. Optionally, the comfort settings may be further include one or more of a humidity setting, pressure setting and a temperature setting.

In some such cases, the processor may be configured to determine a measure of patient ventilation and adjust the variable exhaust area as a function of the measure of patient ventilation. For example, the variable exhaust area may be decreased if the measure of patient ventilation meets or exceeds a threshold. Optionally, the measure of patient ventilation may include an instability index. The instability index may include at least one of a moving window standard-deviation of ventilation, a central apnoea index, a central hypopnoea index, a central apnoea-hypopnoea index, a persistent apnoea-hypopnoea index, and a respiratory disturbance index.

In some such cases, the controller may be configured to detect a Cheyne-Stokes respiration cycle from a patient flow signal and phase-lock adjustments to the variable exhaust area to control rebreathing cycles according to the phase-lock.

The controller may optionally be configured to control operation of a flow generator. The processor may also be configured to detect a presence or absence of an unintentional leak and control the change to the exhaust area based on the detection of the presence or absence of the unintentional leak. Optionally, the processor may close the exhaust area in response to the detection of a presence of a leak or open the exhaust area in response to the detection of a presence of a leak to lower a mask pressure to ambient pressure. In some cases, the processor may close and open the exhaust area in response to a continued detection of a presence of a leak.

Still further, the processor may change the exhaust area as a function of a quantification of the unintentional leak. For example, the processor may decrease the exhaust area based on a threshold comparison of a value of the quantification. The processor may also be configured to detect a sleep state and control the change to the exhaust area based on the detection of the sleep state. For example, the processor may initiate a cyclical variation of the exhaust area in response to the detection of sleep state. Optionally, the processor may maintain an approximately constant exhaust area in response to the detection of an absence of sleep.

In some cases, the processor may be configured to detect a breathing condition and control the change to the exhaust area based on the detection of the breathing condition. For example, the detected breathing condition may be a central apnea or central hypopnea and the processor is configured to control a decrease to the exhaust area based on the detection of the central apnea or central hypopnea. The processor may be configured to control an increase of the exhaust area based on a further detection of an absence of central apnea or central hypopnea.

In some cases, the processor may control changes to the exhaust area in synchrony with detected patient respiration. The processor may control changes to the exhaust area as a function of a measure of pressure. The processor may control changes to the exhaust area as a function of a measure of flow such as a measure of flow through the exhaust area. The processor may control changes to the exhaust area to permit a vent flow of the exhaust area to mirror patient flow. The processor may control changes to the exhaust area as a function of a measure of patient flow. The controller or processor may control changes to the exhaust area as a function of a calculation of a rebreathed volume.

In some cases, the vent assembly may include nested first and second conic structures, each have an opening of the overlapping apertures. The vent assembly may include nested first and second cylindrical structures, each have an opening of the overlapping apertures. Optionally, an opening of the apertures may include a set of grooves.

In some cases, the vent assembly may include nested first and second structures, each have an opening of the overlapping apertures and the actuator may include a motor and an induction coil coupled to the first structure, and the structures may be configured to adapt a size of the overlapping apertures by rotation of the first structure.

In some cases, the actuator may include one or more of a voice coil and a magnet. The actuator may include a pneumatic piston. The actuator may include a motor such as a piezo motor. Optionally, the apparatus may also include a spring mechanism, such a torsion spring, configured to return the variable exhaust area of the vent assembly to a normally open position.

In some aspects, the vent assembly may include a floating aperture portion, which may include a flexible material. The vent assembly may include a foam vent portion, such as a foam that has a variable effective porosity along its length. In some cases, the vent assembly may include a flexible cylinder having a plurality of slits, the plurality of slits being configured to expand and contract with an expansion and contraction of the flexible cylinder. Optionally, the vent assembly may include first and second plates.

Some aspects of the present technology may involve a system for automated control of gas washout of a patient interface. The system may include a vent assembly having a variable exhaust area defined by overlapping apertures of the vent assembly, the vent assembly being attachable to a patient interface; and an actuator to manipulate an aperture of the vent assembly, the actuator configured for control by a processor to change the exhaust area of the vent assembly. The vent assembly may also include nested first and second conic structures, each have an opening of the overlapping apertures.

The vent assembly may include nested first and second cylindrical structures, each having an opening of the overlapping apertures. An opening of the overlapping apertures may include a set of grooves. The vent assembly may include nested first and second structures, each having an opening of the overlapping apertures and wherein the actuator comprises a motor and an induction coil coupled to the first structure, and wherein the structures are configured to adapt a size of the overlapping apertures by rotation of the first structure. The actuator may include a voice coil. The actuator may include a pneumatic piston. The actuator may include an induction coil and/or piezo motor. The system may also include a spring mechanism, such as a torsion spring, configured to return the variable exhaust area of the vent assembly to a normally open position.

In some aspects of the system, the first cylindrical structure may include a coil groove extending along a length of the cylindrical structure and the coil groove may include a coil. Optionally, the second cylindrical structure may be magnetized. In some cases, the first cylindrical structure may be formed by halves split longitudinally such that each half includes a coil groove. In some cases, the first cylindrical structure may be formed in thirds that split longitudinally such that each third includes a coil groove.

In some aspects of the system, the vent assembly may include a plurality of adjustable flaps. Selective movement of subsets of the plurality of flaps may vary the exhaust area of the vent. A plurality of coils may generate magnetic fields to manipulate the flaps. The flaps may be flexible. In some cases, each flap may include a magnetized edge portion.

In some aspects of the system, the vent assembly may include a fabric including a plurality of flexible threads and/or a plurality of flexible layers. Selective movement of one or more subsets of the threads and/or one or more subsets of the layers may vary the exhaust area of the vent. A plurality of coils may generate magnetic fields to manipulate some or all of the threads and/or some or all of the layers.

In some aspects of the system, the vent assembly may include first and second plates. The first plate may include a plurality of projections for selectively plugging corresponding apertures of the second plate. In some such cases, the second plate may include a plurality of projections for selectively plugging corresponding apertures of the first plate. Optionally, the projections may be conic shaped and the apertures may be funnel shaped. A biasing member may be coupled to the first and second plates. The biasing member may bias the first and second plates to an open configuration.

In some aspects of the system, the vent assembly may include one or more caps. Each cap may be configured to selectively cover and uncover a plurality of apertures of an inner vent member. Optionally, a coil may generate a magnetic field to selectively attract or repel the cap(s) with respect to the inner vent member.

In some aspects of the system, the vent assembly may include a vent fan. The vent fan may be configured at an aperture of the vent assembly. The vent fan may have a controller to control the fan to regulate the exhaust through the aperture.

In some aspects of the system, the actuator may include an adjustable diaphragm. The adjustable diaphragm may be configured to selectively increase or decrease expiratory flow through the diaphragm such as by adjusting its diameter. Optionally, the adjustable diaphragm may include a piezo-ceramic ring or an electro-active polymer ring. In some such cases, a plurality of adjustable diaphragms may regulate flow through a plurality of vent apertures. The adjustable diaphragm may also be adapted on a surface of a flexible expiratory conduit. In some such cases, the flexible expiratory conduit may encompass an inspiratory conduit.

In some aspects of the system, the vent assembly may include an expiratory chamber and a piston. The piston may be arranged to move within the expiratory chamber to selectively block one or more venting apertures of a surface of the expiratory chamber. In some such cases, the actuator may include a coil to generate a magnetic field to selectively position the piston. Such vent assemblies may include a manual adjustment mechanism to limit a range of movement of the piston. The manual adjustment mechanism may be configured to apply a tension to a range of movement of the piston. In some cases, the adjustment mechanism may include a threaded post and a spring.

In some such systems, the vent assembly includes nested first and second structures, each have an opening of the overlapping apertures, the apparatus further comprising a processor configured to operate the actuator. The processor may be configured to detect a presence or absence of an unintentional leak and control a change to the exhaust area based on the detection of the presence or absence of the unintentional leak. The processor may close the exhaust area in response to the detection of a presence of a leak. The processor may open the exhaust area in response to the detection of a presence of a leak to lower a mask pressure to ambient pressure. The processor may close and/or open the exhaust area in response to a continued detection of a presence of a leak. The processor of the system may change the exhaust area as a function of a quantification of the unintentional leak. For example, it may decrease the exhaust area based on a threshold comparison of a value of the quantification.

The processor of the system may also be configured to detect a sleep state and control the change to the exhaust area based on the detection of the sleep state. The processor may initiate a cyclical variation of the exhaust area as a function of a detected sleep state. The processor may optionally maintain an approximately constant exhaust area in response to the detection of an absence of sleep. The processor may also be configured to detect a breathing condition and control the change to the exhaust area based on the detection of the breathing condition. The detected breathing condition may include a central apnea or central hypopnea and the processor may be configured to control a decrease to the exhaust area based on the detection of the central apnea or central hypopnea. Such a processor may also be configured to control an increase of the exhaust area based on a further detection of an absence of central apnea or central hypopnea.

In some cases, a processor of the system may control changes to the exhaust area as a function of a measured patient flow. The processor may control changes to the exhaust area in synchrony with detected patient respiration to permit a vent flow of the exhaust area to mirror patient flow.

Optionally, the system may include a controller having a processor, the controller coupled with the actuator, the controller configured to operate the actuator to change the exhaust area of the vent assembly. The processor may be configured to switch between a treatment setting for the variable exhaust area and the comfort setting for the variable exhaust area. The processor may be configured with a user interface for input of comfort settings including a setting for the variable exhaust area. The comfort settings may further include one or more of a humidity setting, pressure setting and a temperature setting.

The processor of the system may be configured to determine a measure of patient ventilation and adjust the variable exhaust area as a function of the measure of patient ventilation. In such a case, the variable exhaust area may be decreased if the measure of patient ventilation meets or exceeds a threshold. Such a measure of patient ventilation may include an instability index. The instability index may include at least one of a moving window standard-deviation of ventilation, a central apnoea index, a central hypopnoea index, a central apnoea-hypopnoea index, a persistent apnoea-hypopnoea index, and a respiratory disturbance index.

Optionally, the controller of the system may be configured to detect a Cheyne-Stokes respiration cycle from a patient flow signal and phase-lock adjustments to the variable exhaust area to control rebreathing cycles according to the phase-lock. The controller may also be configured to control operation of a flow generator.

Some aspects of the present technology may involve an apparatus for automated control of gas flow rate for washout of a patient interface of a respiratory treatment apparatus. Such an apparatus may include a conduit having a gas flow channel. The apparatus may also include a slug configured to traverse within the conduit to vary a gas passage size of the channel of the conduit. Optionally, the gas flow channel may include a plurality of steps for the slug. The gas flow channel may be tapered. Optionally, the plurality of steps may comprise symmetrical steps. The slug may be magnetic. In some cases, the apparatus may also include an actuator for the slug that includes a plurality of electromagnets configured to manipulate the slug.

In some cases, the conduit may include a set of threads, conduit thread, and the slug may include a set of threads, slug threads. The set of conduit threads may include one or more break portion grooves. Such a break portion groove may be a tapered groove. Optionally, the set of conduit threads may include a plurality of thread sizes. Such a set of conduit threads may further include one or more a break portion grooves.

In some cases, an actuator for the slug may be configured to manipulate the slug. Such an actuator may include a plurality of coils positioned externally of the gas flow channel. In some embodiments, the apparatus may include a controller with a processor. The controller may be coupled with the actuator and may be configured to operate the actuator to vary the size of the gas flow channel to permit more or less gas flow through the channel. Optionally, in some embodiments, the conduit may be coupled to a gas washout vent of a respiratory mask.

Some aspects of the present technology may involve an apparatus for control of gas washout of a patient interface of a respiratory treatment apparatus. The apparatus may include an assembly having a variable exhaust area defined by a plurality of overlapping blades of the assembly; and an actuator to manipulate an aperture of the vent assembly, the actuator coupled with the blades. The assembly may include first and second blade mounts. The actuator may include a drive lever coupled with the plurality of blades. The actuator may include a slot for the drive lever. In some cases, the actuator may include a yoke coupled with the drive lever. The actuator may include a ring having magnetic sections. The actuator may include a set of field coils. Optionally, in some cases, the actuator may include a yoke coupled with the drive lever. Such a yoke may include a ring having magnetic sections, and the actuator may include a set of field coils configured to control a rotation of the ring. In some such examples, the apparatus may also include a processor, such as a controller of a respiratory treatment apparatus, configured to operate the field coils.

In some cases, the apparatus may have a biasing member. The biasing member may be configured to bias movement of the actuator toward a pre-set position. The pre-set position may be an open exhaust area defined by the plurality of overlapping blades. In some cases, the apparatus may include a housing coupled with the assembly and actuator. The housing may be a conduit adaptor for a gas delivery conduit of a respiratory treatment apparatus. The housing may be a venting port of a mask for a respiratory treatment apparatus.

Other aspects, features, and advantages of this technology will be apparent from the following detailed description when taken in conjunction with the accompanying drawings, which are a part of this disclosure and which illustrate, by way of example, principles of the technology. Yet further aspects of the technology will be apparent from the appended claims.

BRIEF DESCRIPTION OF THE DRAWINGS

Further example embodiments of the technology will now be described with reference to the accompanying drawings, in which:

FIGS. 2A, 2B and 2C show the components of one example embodiment of a variable area vent assembly;

FIGS. 5a, 5b and 5c contain an illustration of conical versions of the components of a variable area vent assembly;

FIGS. 6A and 6B are graphs illustrating various functions for controlled vent flow verses patient respiratory flow in some embodiments;

FIGS. 9A, 9B and 9C illustrate a variable area vent assembly implemented with rotatable disks;

FIGS. 10, 10A, 10B, 10C, 11, 12A and 12B illustrate various embodiments of a variable area vent assembly for rotatable and/or axial adjustment of vent flow;

FIGS. 15A, 15B, 15C are cross sectional views of a stepped conduit having a movable slug for controlled adjustment of flow through the conduit taken along line ABC of FIG. 15E;

FIG. 15D is a cross sectional view of the conduit of FIGS. 15A, 15B and 15C taken along line DD of FIG. 15E;

FIG. 15E is a top plan view of the conduit of FIGS. 15A, 15B, 15C and 15D;

FIG. 15F is a top plan view of an example movable slug suitable for some embodiments of the present technology;

FIG. 15G is a top plan view of a conduit suitable for use with the slug of FIG. 15F;

FIG. 18A is an isometric view of an example electromagnetic cover member for a variable vent assembly;

FIG. 18B is an isometric view of an inner vent member suitable for use with the cover member of FIG. 18A;

FIG. 18C is an end view of the cover member of the embodiment of FIG. 18A;

FIG. 18D is an end view of a further example embodiment of a cover member similar to the embodiment of FIG. 18A;

FIGS. 19A and 19B illustrate operation of a variable venting assembly including a plurality of magnetically controlled flaps in a closed and open configuration respectively;

FIGS. 20A and 20B illustrate a porous material with layers for selectively varying flow in some vent assemblies of the present technology;

FIGS. 21A and 21B illustrate a porous material with fibers or threads for selectively varying flow in some vent assemblies of the present technology;

FIGS. 22A and 22B illustrate a porous and stretchable material for selectively varying flow in some vent assemblies of the present technology;

FIG. 35 is a cross sectional perspective of the mechanism of FIG. 29A in a conduit housing.

DETAILED DESCRIPTION

Example Respiratory Treatment Apparatus

Figure 1:
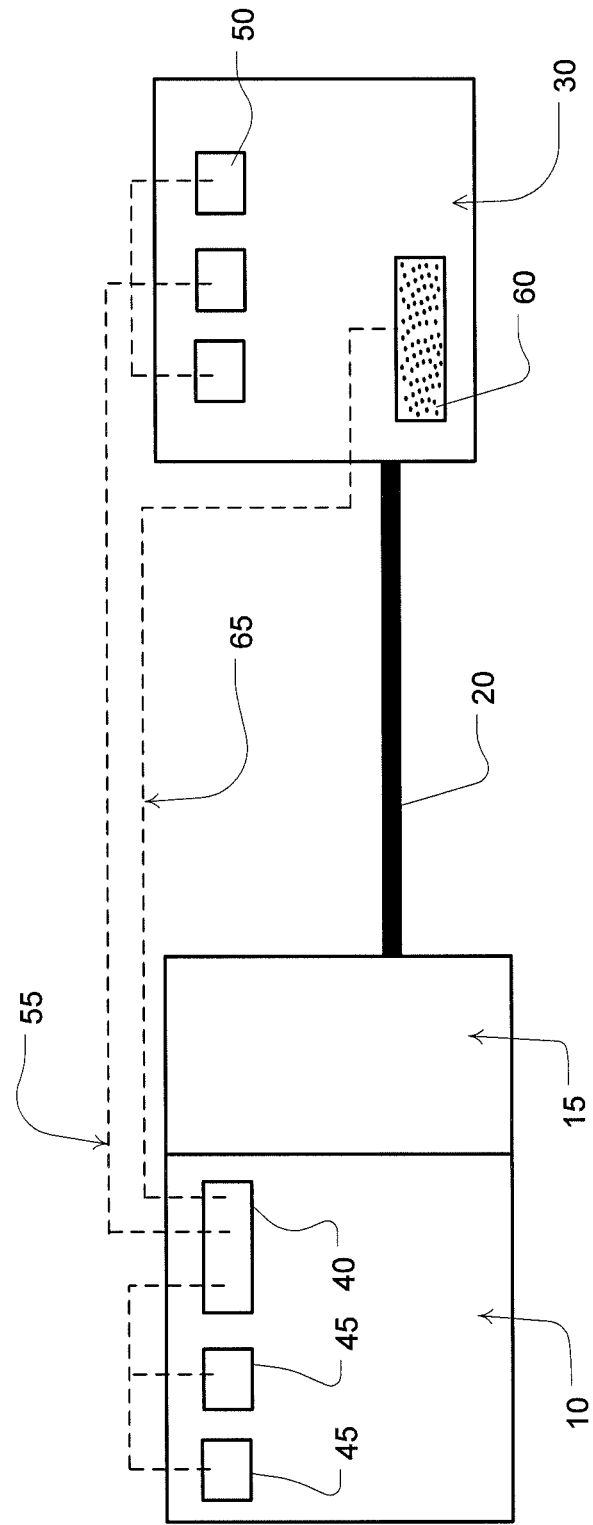
FIG. 1 is a schematic diagram of a respiratory treatment apparatus.

FIG. 1 schematically illustrates an air delivery system of a respiratory treatment apparatus for delivering breathable gas to a patient under pressure, for example, as used in CPAP therapy for sleep disordered breathing (SDB), in accordance with one example embodiment of the current technology.

The basic components of the system of FIG. 1 are a flow generator 10, optionally a humidifier 15 which may be either integrated with or separate from the flow generator, and an air delivery conduit 20 leading from the flow generator—or from humidifier if fitted—to a patient interface 30 which is in communication with the patient's airways.

The air flow generator may be of a type generally known in the art, such as the ResMed S9™ series flow generator, and may incorporate a housing with an air inlet, a blower capable of delivering air to the patient at a pressure of, for example, 2 to 30 cm H2O, or 4 to 25 cm H2O, and an air outlet adapted for connection of air delivery conduit 20 or humidifier 15.

The flow generator may further include sensors 45, such as pressure and flow sensors, and a microprocessor control (e.g., processor 40) which may be capable of receiving signals from sensors 45 and any remote sensors 50, and to use the information from those sensors in control of the flow generator 10 and/or humidifier 15.

The air delivery conduit 20 may be a flexible tube, for example between 8-22 mm or preferably 15 or 19 mm internal diameter, for delivering the pressurized (and possibly humidified) air to the patient interface 30. The conduit 20 may also incorporate one or more heating elements (not shown) for regulating temperature of the gas passing through the conduit and for preventing condensation ("rain-out") inside the tube.

The air delivery conduit 20 may also include one or more wires 55 for carrying signals to and/or from the components (e.g., remote sensors 50) located at or adjacent the patient interface 30 back to/from the processor 40. Alternatively, the signals may be multiplexed and transmitted over a heating wire of the air conduit. An example of a heated tube is disclosed in PCT application WO 2008/055308, filed 8 Nov. 2007. Still further, signals from and/or to the sensors and control components of the vent arrangements may be communicated wirelessly.

The patient interface 30 may be, for example, a nasal, pillows, prongs, cradle, full face or oro-nasal mask sealingly engaging the patient's nares, nose, and/or mouth. Examples of some of these types of mask are the ResMed Mirage Activa™, Mirage Swift™ II mask and Ultra Mirage™ masks.

In the embodiment illustrated in FIG. 1, the patient interface also includes a gas washout vent component—(schematically shown at reference character 60), examples of which are described in more detail below. The air delivery conduit 20 may have a control wire 65 for providing signals to control the gas washout vent and/or other active components at the patient interface end of the conduit. Optionally, the control wire may also carry multiplexed signals representing measurements by sensors associated with the operation of the vent arrangements or sensors of the patient interface.

Alternatively, the vent assembly 60 for gas washout may be positioned in the air delivery path proximal to the patient interface 30. For example, it may be positioned between the patient interface end of conduit 20 and the patient interface 30.

Alternatively, the vent assembly 60 for gas washout may be displaced or positioned remote from the patient interface 30. For example, the vent assembly 60 may be positioned at the flow generator 10.

Variable Area Gas Washout Vent

In some embodiments of the present technology, the gas washout vent component may be a variable area gas washout vent. A variable area gas washout vent may have one or more of the following advantages. A fixed vent will typically require an increase in flow (and power) of the flow generator in order to increase $CO_2$ washout and a decrease in flow of the flow generator to decrease washout. However, a variable vent may increase or decrease $CO_2$ washout without such power increases or decreases simply by opening or closing the vent. Changes to $CO_2$ washout may also be made more rapidly and/or with more precision with a variable vent when compared to waiting for the flow generator to change pressure and flow to do so with a fixed vent. Moreover, when combining flow generator changes with the adjustment of a variable vent, even quicker and/or more precise adjustments to washout may be achieved. Furthermore, use of a variable mask vent can permit a patient to feel less claustrophobic since a more open vent with a greater vent flow can make a mask feel more open.

Moreover, such a vent may allow for a reduction of the flow of air to the patient. It may reduce turbulence of air and thereby decrease noise. It may also reduce turbulence in the mask to better simulate normal breathing. Alternatively, control of the vent can increase turbulence in the mask to improve venting such as for better $CO_2$ washout. It may require less power from the flow generator. It may allow for smaller flow generators and their associated components (e.g., humidifiers). It may reduce the cost of the therapy system (e.g., due to the smaller components). It may also be used to reduce the exhalation pressure which increases comfort and may thereby increase or improve $CO_2$ washout.

FIGS. 2A to 2C show a variable area vent (e.g., vent assembly 60) in accordance with one example embodiment. FIGS. 2A and 2B respectively show an inner vent member 70 component (FIG. 2A) and a cover member 75 component (FIG. 2B). FIG. 2C shows the inner vent member 70 component nested with the cover member 75 component such that the inner vent member is inserted within the cover member to form the variable area vent assembly.

The inner vent member 70 of FIG. 2A may have a generally cylindrical or tubular form, having a central inner bore 80 open at one end and optionally being closed at the other end, for example with an end cap 85. End cap 85 may have an enlarged diameter adapted to locate and secure inner vent member 70 within cover member 75.

At least a vent portion 90 of the surface of the inner vent member 70 is porous and communicates with the inner bore 80 to allow air to pass from the bore through the vent portion.

The inner vent member 70 may be formed of any suitable material and may advantageously be formed of moulded plastic material such as polycarbonate, nylon or porous formed plastics such as polypropylene or similar. Alternatively, inner vent member 70 may be formed of a flexible polymer such as silicone, thermoplastic elastic, or similar. In a further alternative, vent portion 90 of the inner vent member 70 may be formed from a textile or alternative porous material such as foam. In a further alternative, inner vent member 70 may be constructed of a combination of materials, for example end cap 85 and body of inner vent member 70 may be constructed of a polymer such as nylon, with the vent portion 90 being constructed of a fabric, textile or similar.

In some embodiments, the foam for the vent portion 90 of the inner vent member 70 may be formed from a material having a variable effective porosity. For example, the foam porosity along the width and/or length of the foam may vary from less porous to more porous. Thus, depending on which portion of foam of the vent portion 90 is exposed to the venting aperture 95 of cover member 75, the flow through the vent will permit varying degrees of flow. Optionally, the variable effective porosity of the foam may be varied axially or longitudinally to allow variability in venting depending on the relative movement between the cover member and inner vent member. In this regard, the inner vent member 70 may be formed by a foam cylinder having a variable effective porosity around its cylindrical surface for varying flow by its rotational position. Still further, a section from a foam cylinder may fill the vent portion 90 of the inner vent member.

As seen from FIG. 2A, the vent portion 90 may be formed as a curved rectangular portion of a cylindrical surface of the vent assembly 60. Other shapes may also be used. For example, a tapered shape may be employed in some embodiments that are configured to vary the vent open or exhaust area in response to movement of the cover member—as discussed in more detail herein.

The vent portion 90 of the inner vent member 70 may be integrally formed in the vent assembly 60, for example by forming perforations extending from the inner bore 80 to the outside surface of the vent portion 90. The vent portion 90 may comprise a series of vent holes in a uniform or random arrangement. The vent holes may be tapered through their length. Preferably, the vent holes may be convergent (i.e., the vent hole may have a larger diameter at the bore side of inner vent member when compared to the diameter of the vent hole on the atmosphere side of inner vent member.) An exemplary vent arrangement is disclosed in U.S. Pat. No. 6,581,594, filed 15 May 2000.

In the case of an inner vent member 70 formed of porous material such as a foamed plastics material, the vent portion may be formed by surface treatment of the vent member material at the vent portion to remove an outer skin of the porous material.

Alternatively, the vent portion 90 may be formed as an insert in the inner vent member 70, for example as an insert of moulded perforated material or porous material such as foamed plastics, or of a fabric, including but not limited to woven fabrics, non-woven fabrics, spacer fabrics, 3D textiles on molded fabrics.

FIG. 2B illustrates a tubular cover member 75 which is adapted to fit closely about the inner vent member 70 as shown in FIG. 2C.

The cover member 75 formed as an outer sleeve that is movable relative to the inner vent member 70, for example by relative rotation about a common axis with the inner vent member 70. In an alternative form, cover member 75 may be co-planar with inner vent member 70 such that inner vent member translates (rather than rotates) with respect to cover member 75 in a sliding relationship. Optionally, the cover member and inner vent member may be configured to permit rotation and axial translation. Examples of such embodiments are described herein with reference to FIGS. 10 and 11.

The cover member 75 has a venting aperture 95 positioned to align with an area of the vent portion 90 of the inner vent member 70 depending on the relative positions of the cover member 75 and inner vent member 70. Thus, the vent exhaust area will be defined by the size of the overlap of the vent portion and venting aperture and may be increased or decreased depending on the alignment of the apertures of the cover member and inner vent member when at least one, or both, of the apertures is manipulated to a different position.

The vent assembly may be provided with appropriate sealing means, for example, ring seals (not shown) adjacent to each end of the inner vent member, to prevent vent flow from bypassing the aligned vent portion 90 and venting aperture 95.

The cover member 75 may be formed of any suitable material, such as moulded plastics materials including but not limited to those approved for medical uses. Optionally, it may be co-molded to form the inner vent member and cover member together. Such a co-molded embodiment may be implemented with materials that do not bond together. For example, the inner member may be molded first and then the cover member may be molded over it so that the adjacent contact surfaces suitably match each other.

The venting aperture 95 may simply be a cut-out portion of the cover member 75, as illustrated, or may have a porous material such as a foamed plastic or fabric portion.

FIGS. 5A to 5C show another variable area vent assembly 60. FIGS. 5A and 5B respectively show an inner vent member 570 component (FIG. 5A) and a cover member 575 component (FIG. 5B) of a generally conical shape. FIG. 5C shows the inner vent member 570 inserted within the cover member 575 to form the variable area vent assembly.

Generally, this vent assembly may employ two conic structures with a first cone being nested within a second cone as illustrated in FIG. 5C. Such a design employing conic structures may be more compact than alternative arrangements such as the cylindrical embodiments previously described. Conic structures may also be more compact and may withstand wear better than cylinders. That is, with use, the cones wear into each other to help remain in contact during use. The surfaces of nested cylinders on the other hand may wear out so as to cause the surfaces to separate. This wear can cause a degradation in vent performance if contact between surfaces is needed for creating a suitable seal to prevent unintentional leak between the surfaces.

The cones may have a single aperture or number of apertures in a similar manner to that described above. As illustrated in FIG. 5B, the cover member 575 has a venting aperture 595 open to the cavity of the bore 585 of the cover member 575. Similarly, as shown in FIG. 5A, the inner vent member 570 has a vent portion 590 open to the cavity of the bore 580 of the inner vent member 570. In the shown examples, the vent portion and venting aperture are tapered. However, other shapes for these openings may be employed and the shapes and sizes of these openings do not need to both be the same for any given vent assembly 60 with a variable venting area. The venting aperture 595 and vent portion 590 are positioned to align depending on the relative positions of the cover member 575 and inner vent member 570 as illustrated in FIG. 5C. This positioning of the first cone apertures relative to the second cone apertures dictates the amount of gas that can flow from within the inner cone to the outside of the outer cone. As with prior embodiments, either the cover member or inner vent member may be adjusted to increase or decrease a flow of air from the bore cavity through the vent portion and venting aperture of the cones as the area of the vent opening, as defined by the overlap of the vent portion and venting aperture, is increased or decreased depending on the alignment of the cones, when at least one, or both, of the apertures is manipulated to a different position.

As illustrated in FIGS. 5A to 5C, one or both of the cones may also optionally have grooves 596 or notches that may lead to the larger vent portion or venting aperture of the cones. As illustrated in this embodiment, the cover member 575 includes inner grooves 596-I on an internal surface of the conic structure and the inner vent member 570 includes outer grooves 596-O on an external surfaces of the conic structure. Such a configuration may be adapted to create a longer flow path for the air to reduce noise. The grooves may have a triangular or polygonal cross section. The grooves may have a semi-circular or curved cross section. The grooves may also vary in width along their length. For example, at the end of the groove positioned near a larger vent opening, the groove may have a relatively large width and at the end of the groove furthest from the larger vent opening the groove may have relatively small width. This may be a gradual change in width along the length of the grove and may be a tapered groove.

Figure 8B:
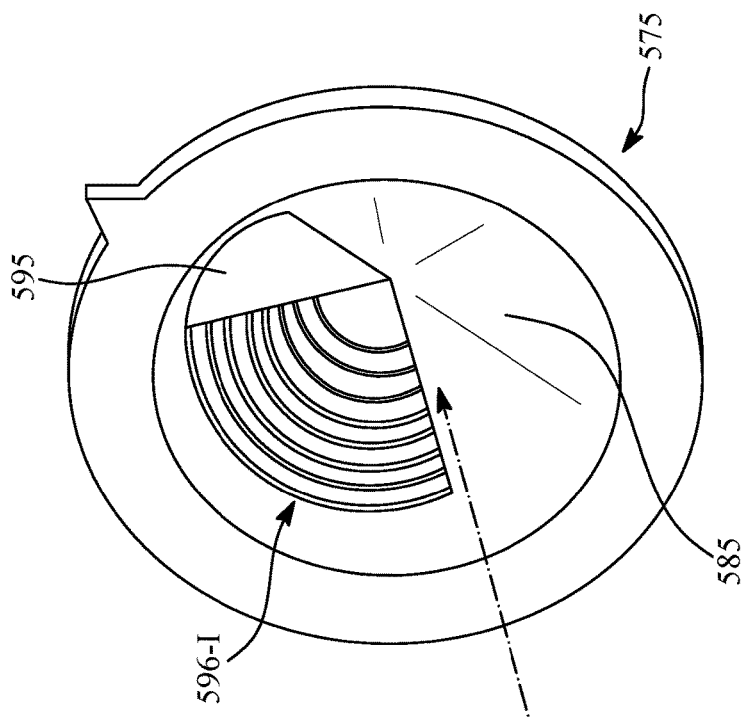
FIGS. 8A and 8B contain an illustration of a further conical example of the components of a variable area vent assembly.
Figure 8A:
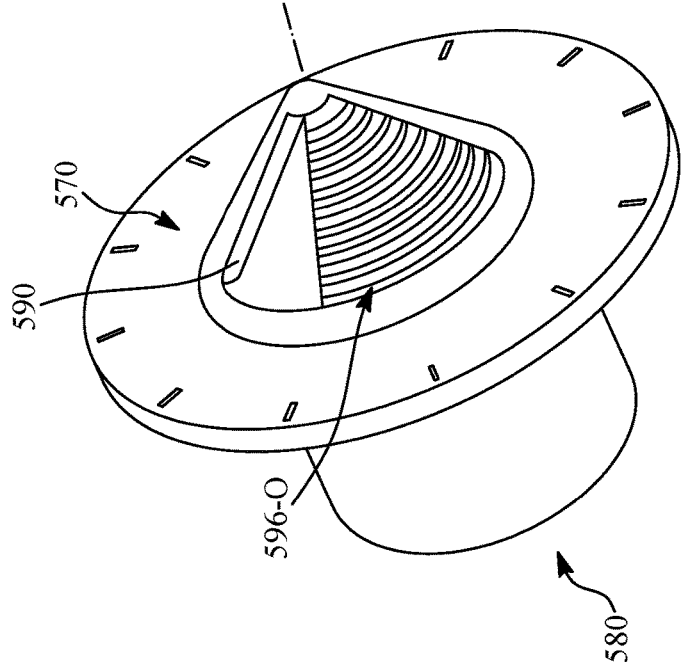

As illustrated in FIGS. 5A and 5B, the grooves of both cones have the same or similar shape. Optionally, and as shown respectively in FIGS. 5A and 5B, the grooves on one cone may be oriented in a first direction and the grooves on the second cone may be oriented in a second direction. Such an opposite orientation arrangement may yield different variations in the amount of flow permitted out of the vent depending on the position of the first cone relative to the second cone. In another version (not shown), the grooves on one of the cones may be oriented in a direction that is generally perpendicular to the grooves on the other cone. Such grooves may also have a width that tapers along their length so as to be larger towards the vent opening. A further example embodiment of a conic vent arrangement is illustrated in FIGS. 8A and 8B.

In order to achieve the variation in the effective vent opening size as previously discussed, either cone may be rotatable relative to the other cone. Optionally, both cones may be rotatable. Thus, the cones may have a screw mechanism and/or pivot to guide the rotation of the cones relative to one another. Depending on the shape of the cones and/or their vent apertures and/or grooves, it may be possible to have a small rotation of one cone relative to the other cone resulting in a large change in vent flow. This may be more effective when compared to cylindrical structures. In an alternative embodiment, the cones may not rotate relative to one another, but could be configured to translate along their central axis (i.e., displace their apexes relative to one another). In some embodiments, such translational movement may also be combined with the rotational movement previously described.

The inner vent member 570 and outer vent portion (e.g., cover member 575) may be formed of the same materials or combinations of materials as described above for inner vent member 70 and cover member 75 respectively.

Alternative physical forms for the vent assembly may be adopted, for example incorporating the vent member and cover member as parallel discs with the respective vent portion and vent aperture being formed in the discs or plates and aligned to expose a variable vent area by relative rotation of the discs or covers. Such as illustrated in FIGS. 9A, 9B and 9C. As illustrated, the surface of a first disk 970 may be positioned, such as within a conduit 990, to contact a surface of a second disk 975 such that a variable vent area is formed by apertures on the disk when the apertures (e.g., venting aperture 595 and vent portion 590) are rotated to aligned to at least partially overlap so as to permit a vent flow through the apertures. As illustrated in FIG. 9B, a triangular aperture may be employed. Tear drop shaped apertures are illustrated in disk of FIG. 9C. In some cases, a central keyed hole of the disk may serve to receive a correspondingly keyed motor shaft for rotation of the disk. Such a motor may be sized to be located within the mask or conduit which contains the disk.

As previously mentioned, in some aspects, the inner vent member and cover member combinations may be adapted to move linearly (e.g., by traversing axially along their lengths) to adjust the vent area and/or by rotation. For example, the cover member may be internally threaded and moved on threads on the outer surface of inner vent member. It may also optionally be moved on a variable helical path such as by being guided by a cam of a motor.

For example, the vent assembly of FIG. 10 may be configured for manipulation by rotation in a direction shown by arrows RM or axially along the lengths of the components (e.g., a central axis of the cylinders) as shown by arrows AM. In such arrangements, vent area flow adjustment can be constructed to provide coarse and/or fine flow adjustments. For example, one motion (e.g., rotation) may be associated with access to larger or more apertures of the vent portion, such as when the apertures are linear, while another motion (e.g., translation) may be associated with access to smaller or fewer apertures of the vent portion such as when the apertures are non-linear, as illustrated in FIG. 10. When the assembly is rotated along arrows RM, a linear row of several apertures (e.g., 7 holes) is simultaneously opened or closed for a coarse adjustment to the vent flow. However, when the assembly is translated along arrows AM, a smaller number or area of the openings is exposed or closed (e.g., as few as 2 holes) permitting a fine adjustment to the vent flow. In such a case, a linear or non-linear configuration of the apertures of the vent portion can be chosen so as to provide different flow characteristics as desired. Similarly, the shape of the venting aperture may be selected to variably expose linearly aligned apertures in a non-linear manner. The vent portions 590 and 595 may either or both be filled with a porous material such as foam or other porous material for noise control. This foam may be of variable density and/or porosity. The variability may vary in any direction.

The components of the vent assembly of FIG. 10 are illustrated in FIGS. 10A, 10B and 10C. This vent assembly employs a floating vent portion 1090 shown in FIG. 10C. The floating vent portion 1090 may be inserted to rest on shelf 1088 of an aperture of the inner vent member 1070 shown in FIG. 10B. The floating vent portion 1090 may be retained in its position in the assembled configuration of FIG. 10 by an inner retaining surface IRS of the cover member 1075 when the inner vent member 1070 is inserted in the cover member 1075. The inner retaining surface IRS includes the inner surface of the boundary of the opening of the cover member 1075, which is smaller than the boundary of the floating vent portion 1090. During use, any internal conduit pressure that results in flow out of the vent can force the floating vent portion to maintain its contact with portions of the inner retaining surfaces IRS of the cover member 1075. In this way, the floating vent portion 1090 may consistently reside in contact with portions of the inner retaining surfaces IRS during use, even in the event of wear on the contact surfaces of the floating vent portion and/or the inner retaining surface of the cover member 1075. The consistent seal between the surfaces may then prevent unintentional vent flow out of any apertures of the vent portion that are not exposed directly to the opening of the cover member. Optionally, the floating vent portion 1090 may be formed of a flexible material to further permit it to flex to maintain its contact with the opening of the cover member when flow from the bore pushes it to contact the edges of the cover member opening(s).

As such, the floating vent portion 1090 can lengthen the product useful life compared to a vent portion that may be integrated with the inner vent member since wear may be tolerated. Similarly, as a separate component from the inner vent member, manufacture of the particular vent portion may be simplified. It may also provide the opportunity for replaceable vent portions and vent portions configured for different venting characteristics. Such an assembly may also permit easier maintenance and cleaning of the components.

FIG. 11 is a top plan view of a vent assembly arrangement that may be manipulated by rotation (arrows RM) and/or axial translation (arrows AM). In this arrangement, the vent portion 90 of the inner vent member 70 has an oval shape and may, for example, include foam or other porous material. As with other embodiments, the manipulation in the various directions of the components may permit a dynamic adjustment to the vent flow.

Figure 12A:
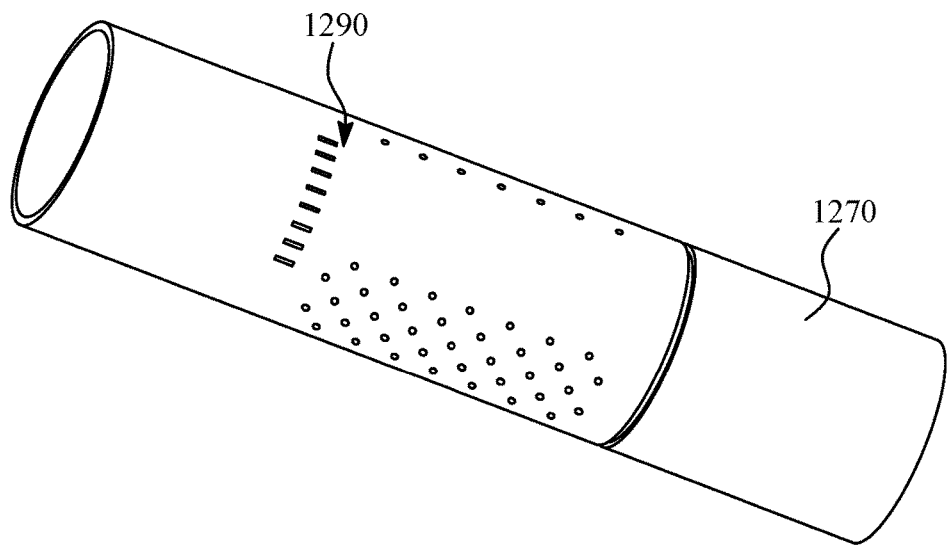
Figure 12B:
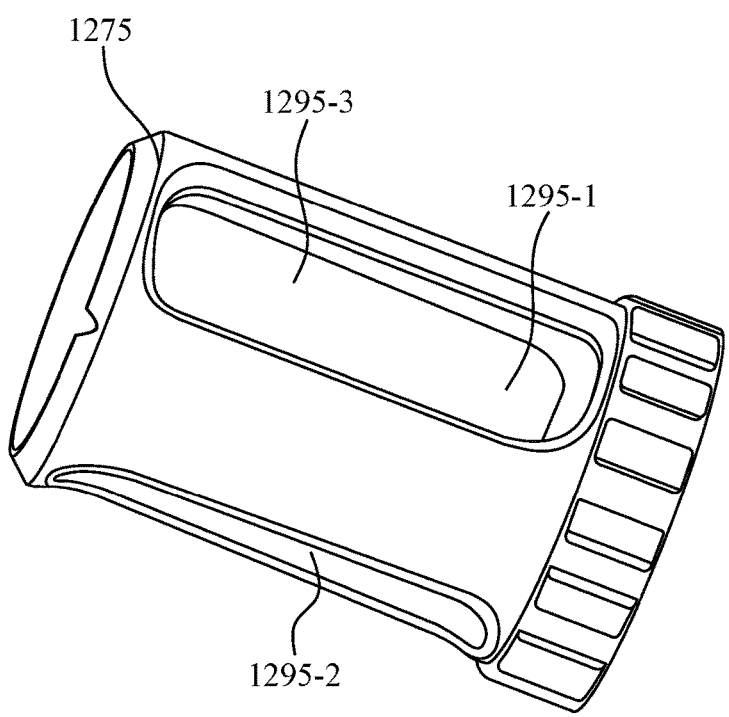

FIGS. 12A and 12B show components of another vent assembly. The inner vent member 1270 of FIG. 12A has a plurality of apertures on its vent portion 1290. The inner vent member 1270 may be inserted within the cover member 1275 of FIG. 12B. In this vent assembly, the cover member 1275 includes a plurality of venting apertures 1295-1 and 1295-2 which, in conjunction with relative movement axially and/or rotationally, can provide variable area venting.

Figure 13A:
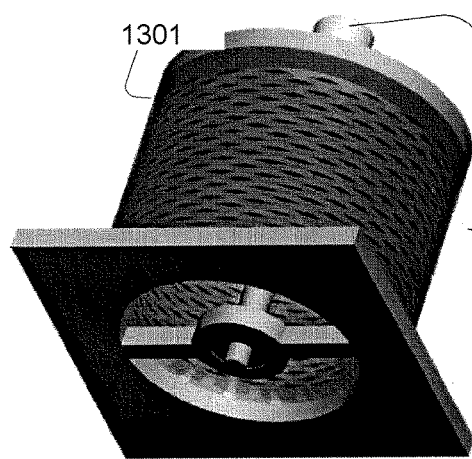
FIGS. 13A, 13B, 13C and 13D illustrate an example compressible/expandable vent assembly for varying vent flow.
Figure 13B:
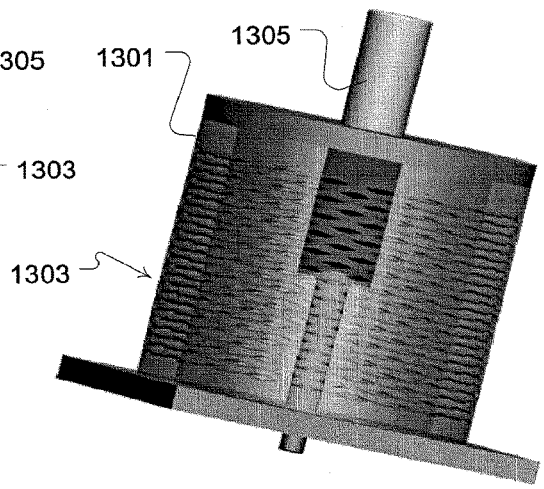
Figure 13C:
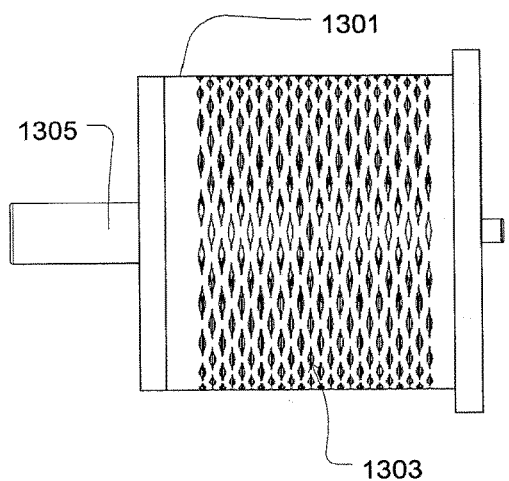
Figure 13D:
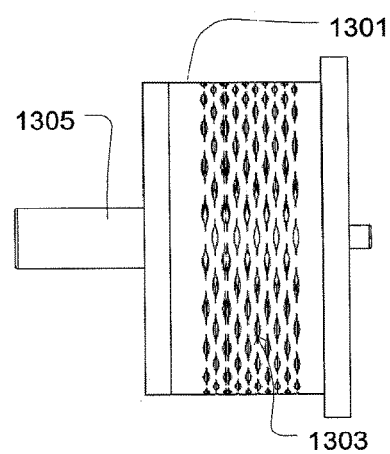

FIGS. 13A, 13B, 13C and 13D illustrate a compressible and/or expandable variable area vent. In this vent assembly, a cylindrical drum 1301 is formed of a flexible material, such as silicone. The drum includes a plurality of slits 1303 around its cylindrical surface that may flex to close and open to varying degrees in conjunction with the axial expansion or compression of the drum. When open, the slits may serve as an exhaust aperture of the variable area vent. To this end, a rod 1305 or piston may be coupled to one or both of the ends of the drum. The rod may be electro-mechanically manipulated such as by a solenoid, to axially lengthen and shorten the drum and thereby variably adjust the openings of the slits 1303. For example, as illustrated in FIG. 13C, the drum is lengthened to expand the opening of the slits and thereby increase an open area of the vent. In FIG. 13D, the drum may then be shortened to reduce the opening of the slits and thereby decrease the open area of the vent. Expired flow from a patient may enter one end of the drum and flow outward from the inside of the drum through the slits to serve as an exhaust vent. Alternatively, expired flow from a patient may enter the inside of the drum through the slits and exit an end of the drum to serve as an exhaust vent. In some cases, the slits or holes of the material (e.g., a membrane or textile) of the cylinder may decrease in size or collapse to reduce flow when stretched or expanded. In such a case, the holes of the material of the cylinder may change shape to reduce flow when the material is stretched. For example, holes of the material, such as an elastic material, may contract in one axis when stretched from the form shown in FIG. 22A to that of the form illustrated in FIG. 22B. Alternatively, the variation in hole shape or size may be triggered by other stimuli. For example, any one or more of a change in temperature, a vibration, an electrical charge or current, or a magnetic field may also be applied to such a material to control the change of shape and/or size.

Figure 14:
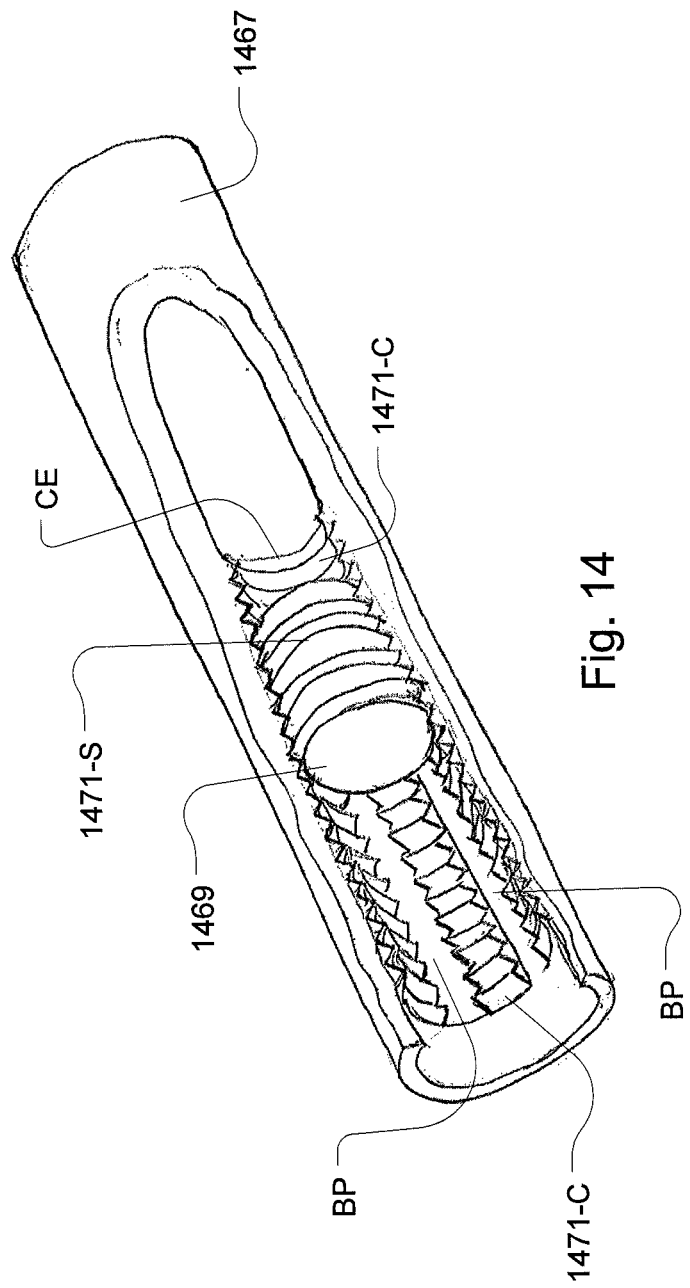
FIG. 14 shows a cross section of a threaded conduit having a movable slug for controlling adjustment of flow through the conduit such as for a variable vent.

The vent assemblies of FIGS. 14 and 15 implement flow control slugs that operate within a vent conduit and may be manipulated by control elements that reside wholly or partially outside of the airflow channel of the conduit. For example, FIG. 14 includes a threaded conduit 1467. In this vent assembly, the flow control slug 1469 is also threaded for traversing along the conduit in conjunction with the threads 1471-C of the conduit. The position of the flow control slug along the length of the conduit sets the amount of flow that may traverse through the conduit. For example, in the illustrated embodiment, the threads 1471-C of the conduit may circumscribe the complete internal surface of one portion of the conduit at one end of the threads 1471-C shown as complete end CE in FIG. 14. When the slug is threaded within these threads, no flow can traverse the conduit since the slug will block the internal channel of the conduit. However, from the complete end CE traversing along the conduit, the threads 1471-C may include one or more break portions BP where the internal surface of the conduit is not completely circumscribed by the threads. The break portion BP may be considered a groove that runs approximately perpendicularly across some portion of the threads 1471-C of the conduit. When the slug rotates through the conduit to reside adjacent to a portion of the threads 1471-C that contain one or more break portions, the conduit is opened at least to some degree so that gas flow can pass by or around the slug through the groove of the break portion, thereby allowing flow through the conduit.

Optionally, the flow can be varied by varying the location, number of break portion grooves and the width of the break portion groves along the length of the conduit. In this way, varying degrees of flow may be permitted and it may be configured to provide either course increases/decreases or fine increase/decreases in the flow of the conduit. For example, a set of grooves may be tapered along the length of the conduit. As the flow control slug rotates to reside adjacent to a small width of the taper of the groove(s), less flow through the conduit is allowed. Similarly, as the flow control slug rotates to reside adjacent to a wider part of the taper of the groove(s), more flow through the conduit is allowed. Based on a tapered configuration of the grooves, flow through the tube may be varied gradually as the threaded slug is advanced (rotated in its threads) along the tube from being near a narrow tapered portion to being near wider tapered portions.

Automated movement or rotation of the flow control slug may be implemented by driving the slug as a rotor of a brushless electric motor. Optionally, slug movement may be implemented with coils of electro-magnets on the outer surface of the conduit or embedded within the conduit wall. In such a case, the slug may be partially magnetic to promote its rotation depending on the activation of the coils. The slug may be driven to rotate by a motorized rod. Optionally, the threads may be multi-start threads to permit easier movement of the slug through the conduit. Alternatively, a rod of a solenoid, which is rotationally coupled to the slug, may push or pull the slug. Optionally the slug and conduit may not include threaded surfaces.

In further arrangements, the size of the threads 1471-C of the conduit may be varied along the length of the conduit such as by varying the clearance between threads of the conduit and slug. In this way, space between loosely fitted threads 1471-S of the slug and the threads 1471-C of conduit may permit some airflow through the conduit and around the slug. However, closely fitted threads can prevent flow. Such arrangements may be implemented without break portion grooves. For example, one portion of the conduit may have threads 1471-S of a first size, such as one with a certain profile height. A next portion of the conduit may have a second smaller size thread (e.g., a smaller profile height) and a still next portion of the conduit may have a third still smaller size thread (still smaller profile height). The first size thread of the conduit may be substantially the same as the threads 1471-S of the slug. When the slug is adjacent to the first threads, no flow will circumvent around the slug through the conduit because the slug will closely fit in the threads of the conduit. When the slug is rotated to be adjacent to the second size threads, some flow of conduit may circumvent the slug through the conduit because the threads of the slug will loosely fit in the threads of the conduit. When the slug then is rotated further to be adjacent to the third size threads, even more flow may circumvent the slug to pass through the conduit because the threads of the slug will even more loosely fit in the threads of the conduit.

In such arrangements, a gradual change of the thread size from one end of the conduit to another can provide a continuous fine adjustment of the flow through the conduit as the slug advances along the conduit through the various threads. Optionally the use of such a variation in thread sizes may also be implemented with break portion groove(s).

FIG. 15 illustrates a walking flow control slug 1569 that may be implemented without threads to regulate the gas flow through a stepped conduit 1567. FIG. 15E is a top plan view of the stepped conduit 1567. FIGS. 15A, 15B, and 15C each show a cross sectional view of the stepped conduit 1567, taken along line ABC of FIG. 15E. FIG. 15D shows another cross sectional view, taken along line DD of FIG. 15E, of the same stepped conduit of FIGS. 15A, 15B, and 15C. The stepped conduit employs a plurality of spaced steps 1573 along its length. The steps are shown staggered on opposing sides of the conduit. However, other step configurations may be implemented such as symmetrical steps that are positioned symmetrically on one side of the conduit relative to the opposing side of the conduit. As illustrated in FIG. 15A, the conduit may employ electro-magnets 1575 to manipulate the slug 1569 within the flow path of the conduit. For example, as illustrated in FIG. 15A, activating the electro-magnets coupled only to magnet control C1 and C2 can maintain the slug at the position illustrated. By sequentially operating the magnet controls (e.g., C1, C2, C3 and C4) the slug may be manipulated along the tube. Magnet controls C2 and C3 may then be activated (and C1 and C4 deactivated) to move the slug from the position of FIG. 15A to the slug position shown in FIG. 15B. Similarly, the slug may be moved to the slug position shown in FIG. 15C by activating magnet controls C3 and C4 and deactivating magnet controls C1 and C2. In this example, stationary electro-magnets manipulate the slug. However, in some embodiments, movable magnets at the exterior of the conduit may be mechanically shifted along the exterior of the conduit for stepping the slug within the conduit.

As illustrated in the cross section view of FIG. 15D, the conduit may be tapered to have a wide end WE and a narrow end NE. When the slug is held in the narrow end of the taper, little or no flow is permitted through the flow channel 1577 of the conduit since the slug will block the channel. However, as the slug is advanced to wider portions of the taper by activation of the magnets, more flow will be permitted to flow through the channel and around the wider gap of the slug. In this way, the slug may variably regulate flow through the channel. Moreover, flow may vary gradually as the slug advances along the conduit.

While a slug having an oval type configuration as illustrated in the FIG. 15D may be employed, the slug may also be implemented with other configurations, which may depend on the profile of the conduit. For example, FIG. 15F is a top plan view of a slug 1569 including a plug portion 1569P and extremity portions 1569E. A top plan view of a conduit suitable for use with the slug of FIG. 15F is shown in FIG. 15G. In such an embodiment, the plug portion 1569P may be suitably adapted for the cross sectional shape of the tapered portion of the conduit such that when it is located at the narrow end NE of the conduit, the exterior surface shape of the plug portion will correspond with an interior surface shape of the conduit with no gap or a nominal gap between the surfaces. When located at the wide end WE of the conduit, the exterior surface shape of the plug portion will correspond with an interior surface shape of the conduit but a significant flow gap between the surfaces will exist. In this way, the plug portion may be implemented for variably blocking the flow channel of the conduit. Thus, the plug portion 1569P may be approximately round as shown in FIG. 15F but also may be other shapes (e.g., rectangular, spherical, etc.). The extremity portions of the slug may extend beyond the surface of the plug portion as shown in FIG. 15F so as to permit their selective engagement with the steps of the conduit. In this regard, the steps 1573 may be optionally formed within opposing channels SC along the length of the conduit. The extremity portion may then traverse the conduit within the step channels SC to selectively engage with the steps.

The slug may be formed of any suitable materials. Thus, although the slug itself may be formed from one magnetic material, multiple materials may be utilized. For example, the plug portion may be formed of a non-magnetic material (e.g., a plastic material) suitable for movement within the flow channel of the conduit and blocking flow. The extremity portions may be formed of a magnetic material (e.g., a metal or magnet) suitable for stepping through the step channels SC of the conduit in accordance with the particular movement control elements.

Figure 23A:
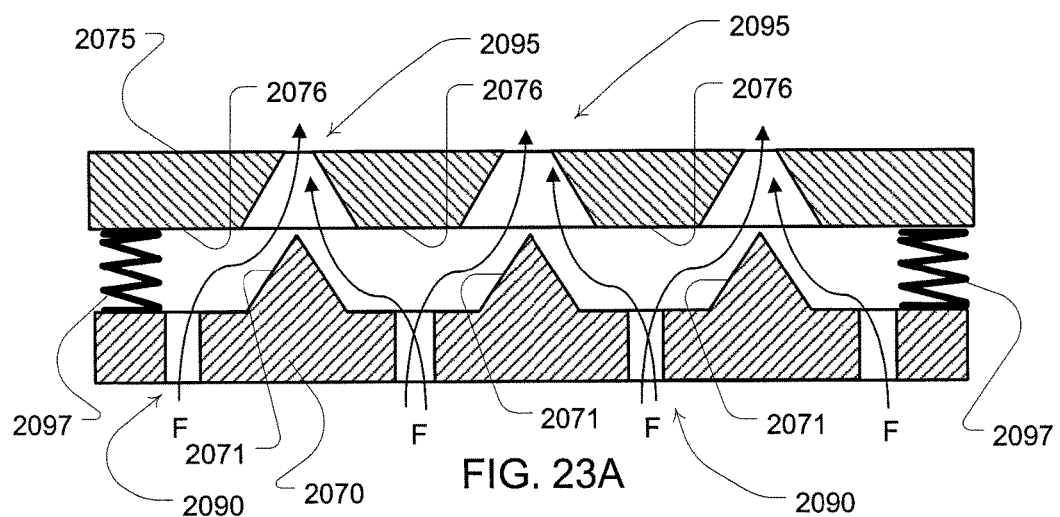
FIGS. 23A and 23B illustrate a venting assembly with mating protrusions for selectively varying flow in some vent assemblies of the present technology.
Figure 23B:
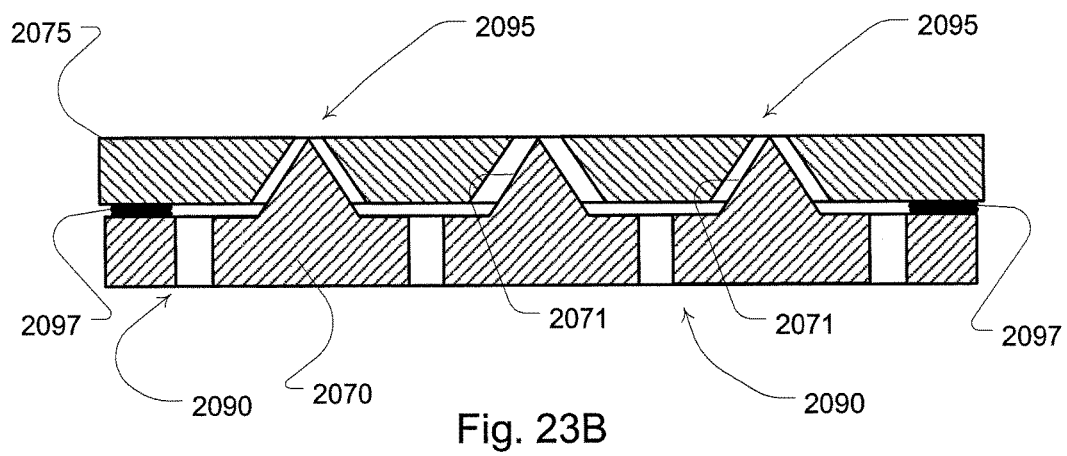

The variable vent assembly of FIGS. 23A and 23B employ complementary venting protrusions on both the cover member 2075 and the inner vent member 2070. In example of FIGS. 23A and 23B, upper and lower plates include apertures to selectively permit flow through the plates. Thus, a plate of the cover member 2075 may include venting portion with apertures and mating projections 2076 for selectively plugging or blocking the flow through apertures of the vent portion 2090. Similarly, a plate of the inner vent member 2070 may have apertures that form the vent portion 2090 and mating projections 2071 for selectively blocking or plugging the holes of the venting aperture 2095. Optionally, the projections and mating apertures may be formed by conic and funnel structures. One or more biasing members, such as spring mechanisms 2097, may bias the plates apart or together to an open or closed position respectively, such as the closed position illustrated in FIG. 23B. Optionally, air pressure on the inner vent member side of the assembly may expand the biasing member to permit flow F through the assembly as illustrated in FIG. 23A. In such a case, an absence of a sufficient air pressure on the inner vent member side will not overcome the force of the biasing member to thereby impede or prevent flow through the assembly. Selection of the different spring constant and venting aperture characteristics can allow the vent to be configured for venting operation at different pressures. Moreover, the implementation of different spring constants with several different biasing members across the length of the venting structure in one assembly can allow different responses to pressure in different areas of the vent to provide further variation of flow characteristics through the assembly in response to different pressure conditions. The biasing or movement between the two plates of the assembly may be controlled by selective activation of one or more magnetic fields using coils (not shown) where one or both of the plates may be magnetic. In such a case, the springs may or may not be omitted.

Figure 24A:
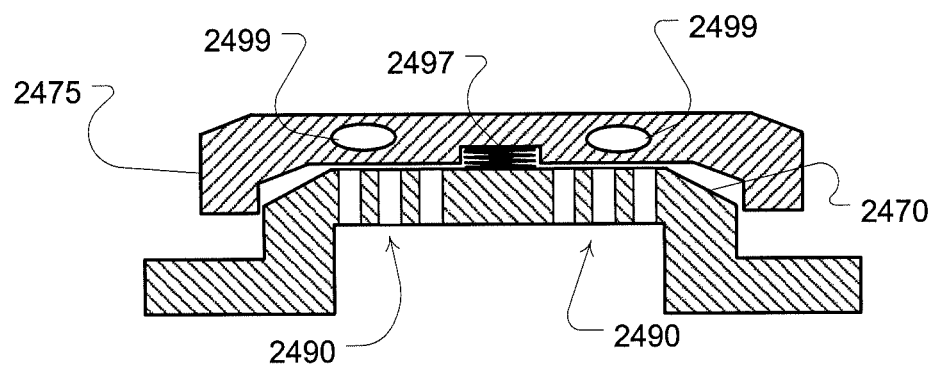
FIGS. 24A and 24B show cross-sectional views of another example embodiment of a vent assembly in closed and opened positions respectively.
Figure 24B:
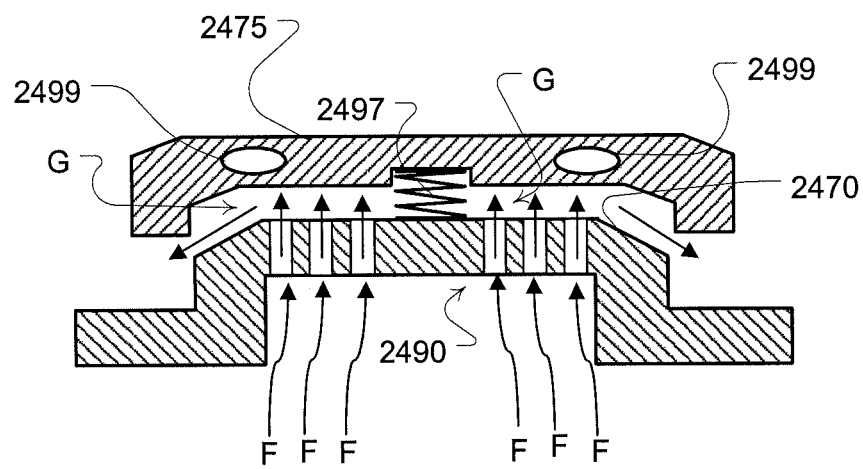

In the vent assembly of FIGS. 24A and 24B a cap-like structure may serve as a cover member 2475 to selectively open and close the apertures of the vent portion 2490 of the inner vent member. The cover member itself does not include a venting aperture. However, one or more gaps between the cover member 2475 and the inner vent member 2470 permits flow through the inner vent member to be vented to atmosphere as illustrated in FIG. 24B. A biasing member, such as spring mechanism 2497 may bias the cover member 2475 in either a closed or open position (e.g., without gap G or with gap G respectively.) Optionally, one or more coils 2499 to generate electro-magnetic field(s) may be included to alter the bias of the spring. For example, by applying current or different amounts of current to one or more coils 2499 selectively, the size of the opening or the force required to open the vent may be varied. For example, the vent may be operated to be normally closed as a result of the spring and/or electro-magnetic field acting upon the inner vent member and/or cover member. When a patient exhales, and when a sufficient internal air pressure builds due to the exhalation, the pressure may overcome a portion of the spring force and/or magnetic force to open the cover member. By increasing or decreasing the magnetic force that attracts the cover member 2475 to the inner vent member, the internal air pressure required to open the vent may be increased or decreased respectively. Alternatively, by increasing or decreasing the magnetic force that repels the cover member 2475 from the inner vent member, the internal air pressure required to open the vent may be decreased or increased respectively.

Figure 25:
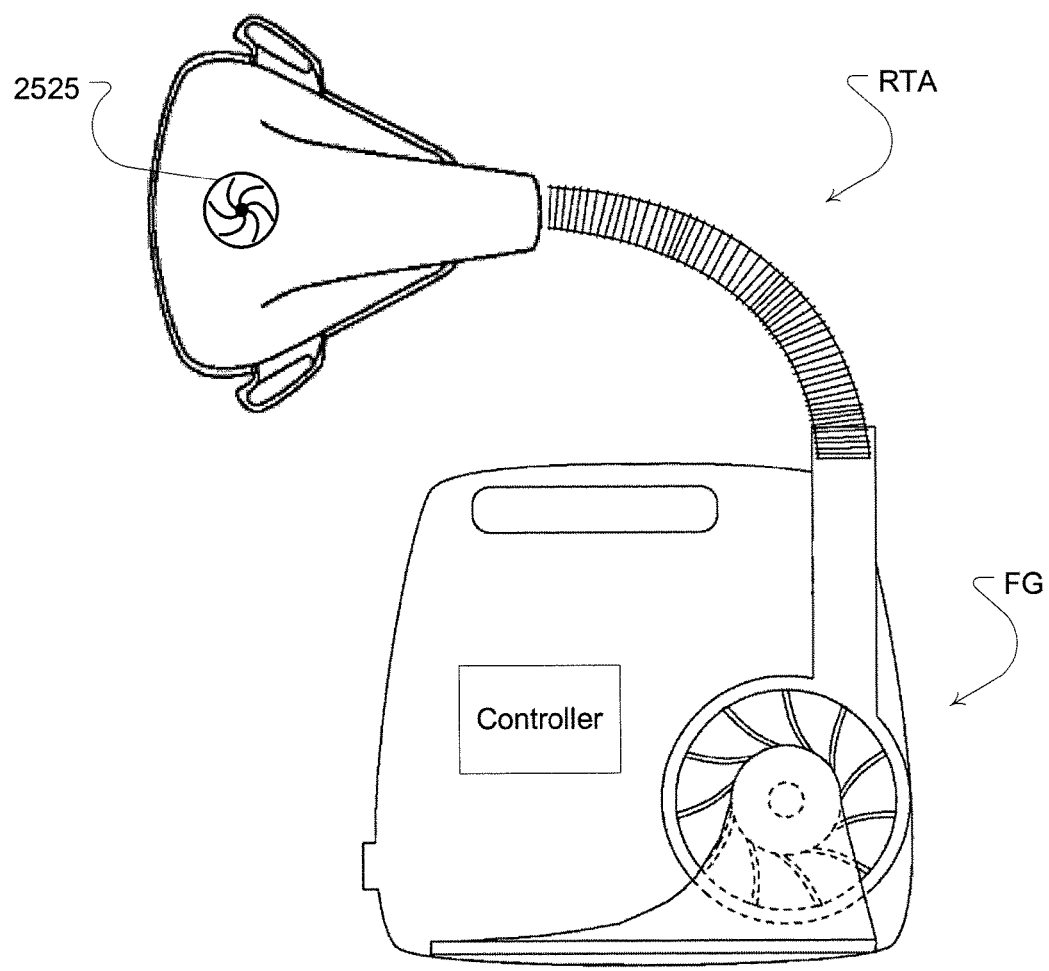
FIG. 25 is an illustration of respiratory treatment apparatus with a patient interface that includes a mask fan vent.

In some arrangements as shown in FIG. 25, flow through a vent aperture of the mask may be varied by control of a mask vent fan 2525 (e.g., a motor and a vaned disk) that is incorporated into a venting aperture of the mask. The vent fan may be controlled by a controller of a respiratory treatment apparatus RTA. The controller, such as one with one or more processors, may also be configured to control a flow generator FG (e.g., blower) of the respiratory treatment apparatus that would generate pressure treatment. The vent fan may then serve as the vent outlet in the mask. For example, the vent fan may be controlled to spin in a direction so as to apply an inward flow and pressure against an expiratory flow from the mask. Such control may prevent or impede flow out of the mask through the aperture of the vent fan. When the vent fan is unpowered, pressure in the mask may flow through the aperture of the vent fan and may thereby spin the vent fan. This expiratory spinning of the vent fan may optionally be applied to inductively charge an energy store (e.g., a battery). The vent outflow may be varied by variably powering the motor of the vent fan. For example, the vent fan may be powered to generate flow inwardly into the mask during patient expiration. In some cases, the mask fan may be powered to generate flow outwardly from the mask to ease expiratory flow.

Figure 26A:
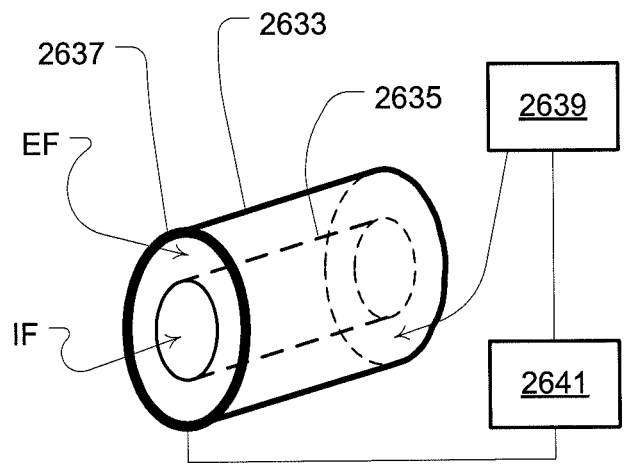
FIGS. 26A and 26B illustrate operation of a conduit for a variable area vent including an adjustable diaphragm in an open and partial closed position respectively.
Figure 26B:
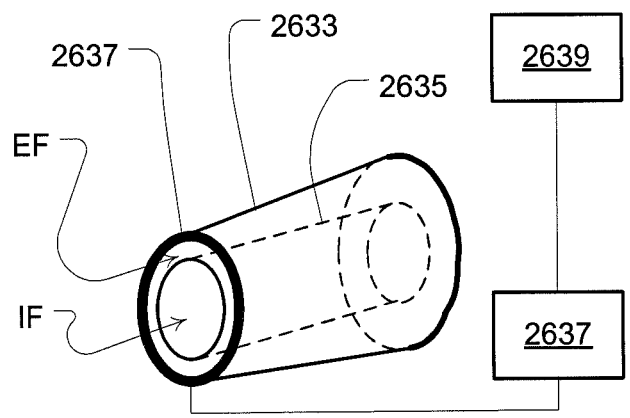

As shown in FIGS. 26A and 26B, control of variable venting may be implemented with an adjustable expiratory conduit implemented with one or more controllable diaphragms. For example, as illustrated in FIGS. 26A and 26B, an expiratory conduit 2633 that conducts an expiratory flow EF may be formed by a flexible material. Optionally, the expiratory conduit may also contain an inspiratory conduit 2635 to conduct an inspiratory flow IF. The inspiratory conduit may be formed of a more rigid material than the expiratory conduit. One or more adjustable diaphragms 2637 may be applied to the conduits such as to the outer circumference of the expiratory conduit. The adjustable diaphragm 2637, which may optionally be implemented by one or more piezo-ceramic or electro-active polymer rings, may be controlled to selectively adjust a circumferential surface of one or more of the conduits. For example, diaphragm 2637 may be controlled to expand or relax as illustrated in FIG. 26A to permit greater flow through the expiratory channel of the expiratory conduit. Similarly, the diaphragm may be controlled to reduce its circumference so as to constrict a surface of the conduit and thereby restrict a flow passage size of the conduit. For example, as illustrated in FIG. 26B, the diaphragm 2637 may be controlled to variably constrict to different degrees to thereby selectively reduce the expiratory flow passage size of the expiratory conduit. A feedback control loop of a controller 2641 may regulate this channel size, for example, by monitoring pressure with a pressure sensor 2639 associated with the expiratory channel, and by adjusting the size of the diaphragm as a function of a desired pressure and the measured pressure. While a single conduit assembly is shown, it will be understood that multiple expiratory conduits with multiple diaphragms may be configured to selectively control a venting area formed by such assemblies.

Respiratory Treatment Apparatus Incorporating Variable Area Gas Washout Vent

Figure 3:
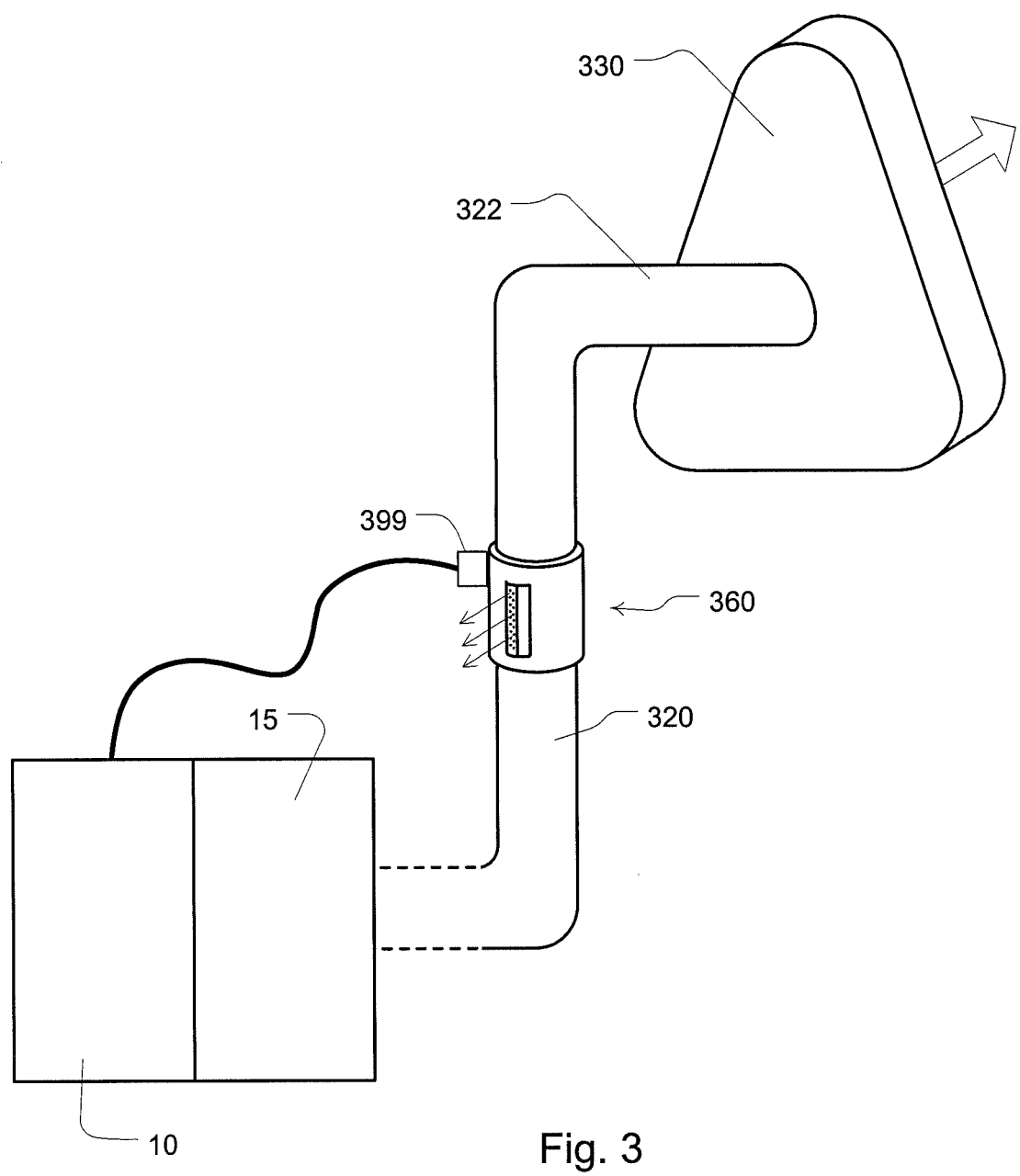
FIG. 3 shows incorporation of a variable area vent assembly into a respiratory mask and gas conduit arrangement.

FIG. 3 is a schematic illustration showing an incorporation of a variable area gas washout vent assembly into a respiratory treatment apparatus in accordance with one aspect of the current technology.

In the arrangement of FIG. 3, the respiratory treatment apparatus includes a flow generator 10 and humidifier 15 arranged generally as described above for FIG. 1. However, as noted above the use of a humidifier 15 is optional. An air delivery conduit 320 delivers pressurized air from the flow generator to a patient interface for applying the generated air pressure to the patient's airways. In the illustrated embodiment the patient interface is of the triangular full face or nasal type respiratory mask patient interface 330. However, other types of patient interface may be applicable.

The mask-type patient interface 330 includes an elbow or connecting element 322 for connection of the mask to the air supply.

The gas washout vent assembly 360, generally in accordance with any one of the aspects described above, can be provided with one or more end connectors (not shown) for connection to the air delivery conduit 320 and the elbow connecting element 322 for location in the airway path between the air delivery conduit and the elbow so that it may be substantially near the patient interface 330. Alternative positions may be implemented (e.g., between the elbow and the mask.) The gas washout vent assembly 360 thus allows venting of exhaled gases from the patient.

The vent assembly 360 and delivery conduit 320 may further include mating electrical connectors for power take off and conveyance of feedback and control signals, as further described below.

Figure 4:
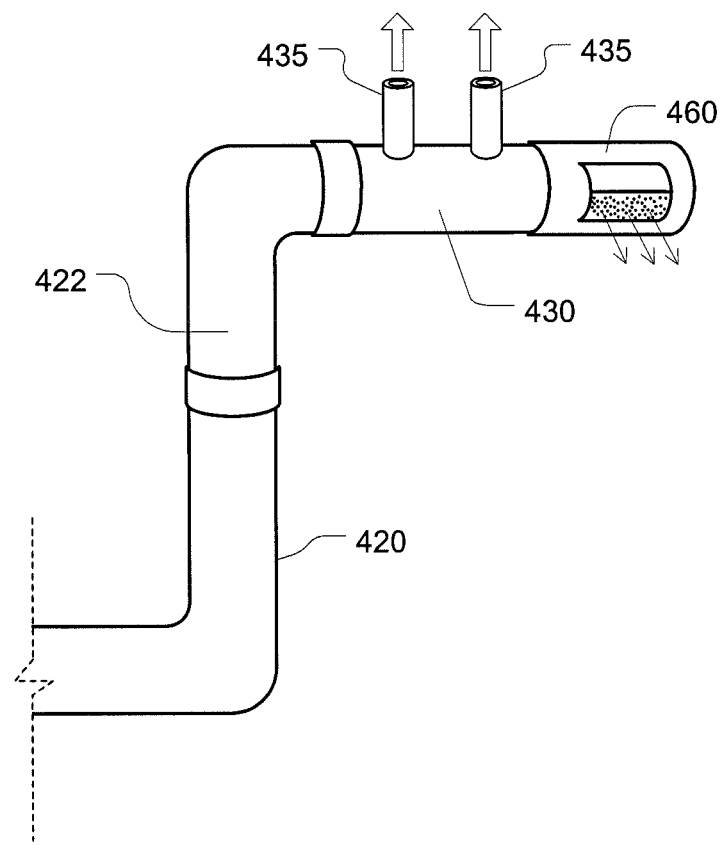
FIG. 4 shows incorporation of a variable area vent assembly into an under-nose nasal pillows style respiratory mask.

FIG. 4 illustrates a further gas washout vent according to the current technology implemented with a respiratory treatment apparatus. In this apparatus, an under-nose patient interface, such as a nasal cushion, nasal pillows or prongs, includes the gas washout vent.

The apparatus of FIG. 4 also includes an air delivery conduit 420 leading from a flow generator (not shown) to the patient interface 430, which in the illustrated example includes nozzles 435 for sealing against the patient's nares.

In contrast to the example of FIG. 3, in FIG. 4 the vent assembly 460 is incorporated in the patient interface 430, attached to the distal end of the interface 430, opposite from the pivotable elbow 422. The vent assembly 460 is illustrated as a modified version of the vent assembly of FIGS. 2A to 2C or a cone shaped assembly, but alternatively may take the form of any of the vent assembly arrangements described herein, including a disc-type vent and vent the gases from the end of the assembly rather than the circumference. In some cases, an outlet muffler may be added to assist in reducing noise at the vent. For example, a tube or conduit may be added at the output of the vent to take noise further away from the mask or ears of the patient. This may also permit expired air to be channeled away from patient's face.

Actuation of Vent Flow Adjustment

In its simplest form, the relative positions of the cover member 75 and inner vent member 70 in FIGS. 2A to 2C may be manipulated manually to cover or expose variable areas of the vent portion 90 and thus allow adjustment control of the vent flow characteristics. The vent may have a manual setting for the vent area which may provide a DC component (offset) to the vent flow. Fine or course adjustments to the vent flow of such a vent may then be controlled by a controller by increasing or decreasing the vent area from the manually set vent area. The adjustment of the vent area may be continuously variable depending on the relative displacement of the cover member with respect to the inner vent member. For example, the two may be held by friction between the inner surface of the cover member and the outer surface of the inner vent member. Alternatively, a retaining mechanism may be employed to permit the adjustment to be made by selection of a particular position from a plurality of discrete set positions. As illustrated in the example of FIG. 2C, the vent assembly may optionally have markings 91 which indicate variable vent settings based on the relative rotational positions of the cover member 75 and vent portion 90.

The range of adjustments may be preset by the clinician, to set the variable vent characteristics in accordance with a prescription for the patient's therapy.

The vent assembly may include an actuator for adjustment of the vent characteristics.

For example, the vent assembly may be biased towards the open position, such as by means of a torsion spring, to form a normally open vent which operates also as an anti-asphyxia valve for the patient mask. The actuator may then act against the force of the biasing means, to close the vent either fully or proportionally. Such an optional spring mechanism 97 is illustrated in FIG. 2A.

Suitable actuators may be implemented by different types of components. For example, a voice coil may serve as the actuator including linear and rotary or swing arm voice coil actuators. An example placement of a coil 99 for an actuator such as a solenoid or voice coil is illustrated in FIG. 2A. Alternatively, piezo actuators (both direct and/or amplified) may be implemented. Further alternatives include pneumatic actuation (including pneumatic amplification). In such arrangements, a bleed conduit from the flow generator pressure may be provided to the mask to power a piston actuator. The piston may rotate or slide the vent assembly into the desired position as controlled by the pressure applied to the bleed conduit by one or more servo-valves, proportional valves or flow control valves. An example pneumatic piston 399 is illustrated symbolically in the embodiment of FIG. 3.

When a solenoid is utilised as the actuator, a voltage may be transmitted by a controller of the flow generator to the solenoid positioned to manipulate the vent assembly such as by adjusting the relative position of the inner vent member with respect to the cover member. The voltage transmitted to the solenoid may alter the position of the solenoid and hence the position of the vent assembly. For example, a first voltage may be applied to the vent assembly to position the vent assembly at a first position (e.g., half of the vent assembly open to atmosphere). A second voltage may be applied to the vent assembly to position the vent assembly at a second position (e.g., all of the vent assembly open to atmosphere). Such adjustable positions of the vent may be discrete but they may also be continuously variable and may run between fully opened and fully closed or some other set limits there between.

In the case of an electrically powered actuator type such as voice coil or piezo actuator, the actuator may be provided with its own power source such as a battery. Optionally, it may be powered by an electrical power take-off, for example, from the heating circuit of the air delivery conduit 20 in FIG. 1. The vent assembly and air delivery conduit may be formed with mating electrical connectors for this purpose. Still further, the actuator may be powered by inductive or transformer coupling.

A voice coil actuator may be configured to achieve the relative displacement of the vent assembly, such as the displacement of the conic structures of the gas washout vent (e.g., vent assembly 60). For example, a coil of wire may be attached to one movable cone (e.g., an apex of the outer cone or inner cone.) A magnet may be positioned in a fixed location, for example, a portion of a frame of the patient interface that is adjacent to the vent assembly. When a voltage is applied to the wire, the magnetic forces may then cause the repositioning of the cone and thereby change the alignments associated with the vent openings. Different positions of the cone may be set by controlling an application of different voltages or currents to the coil.

Furthermore the actuator may include an induction coil attached to the vent apparatus, such as a portion of one of the conic or cylindrical members of the vent apparatus. Optionally, a motor, such as a piezo motor, may also be attached to the induction coil. The actuator may be implemented with just a coil and/or just a piezo motor/driver. In some cases, vent assembly may be implemented without a position sensor such as by controlling a solenoid and measuring the vent flow rather than vent position. Alternatively, the vent assembly may be implemented with just a motor or driver that adjusts the position of the vent.

The control signals for the adjustment of the vent may then be learned by running a 'learn' or 'initiation' cycle. Such a cycle may optionally be implemented by the controller of the flow generator. Such a system may learn the amount of power required to adjust the vent and may optionally do so without the need (or expense) for a position sensor. Such a learn cycle may be initiated at the commencement of therapy. In such a cycle, a series of voltages may be sent to the motor (e.g., modulate the voltage) to induce a series of voltages in the induction coil to cause the vent assembly to linearly move or step through the alignment positions of the vent from completely closed to completely open. For example, when the vent arrives at its end and no more power is required to move the vent, the system may stop. The data concerning the minimum and maximum voltages may then be recorded or saved in association with the minimum and maximum vent positions or the linear positions of the vent. Similarly, the minimum voltage required to initially move the vent may be recorded. Data representing voltage that is required or desired to move the vent from the minimum to maximum positions (or vice versa) may also be recorded. In the event that the current is controlled, the current required for setting the movement of the vent to any desired position associated with a particular voltage may alternatively be recorded. In setting the vent assembly for use, the controller of the flow generator may calculate the required vent flow based on the characteristics of a certain mask such as by the methods described in WO 2002/053217. Based on learned values and the known characteristics of the vent, the controller may control applying of a voltage or current to the motor or solenoid to position the vent to obtain the desired flow.

A piezo motor may be advantageous as it requires lower power to run such as in the case that power is only needed to move the vent and power is not needed to oppose a biasing force to maintain the vent in a certain position. A piezo motor however may be less accurate than a biasing force and solenoid actuator, as a spring and solenoid arrangement may be able to operate with more accuracy in a small stroke.

FIGS. 18A and 18B, show a vent assembly configured in a solenoid arrangement. The cover member 1875 includes both a venting aperture 1895 that may be formed by a plurality of holes and one or more winding grooves 1891. The winding grooves 1891 extend along the inner bore generally parallel with the bore of the cover member 1875. Optionally, such grooves may be implemented on the outer surface of the cover member as well (not shown). The winding grooves provide a channel for windings of the coil 1899 that may serve to electro-magnetically operate the inner vent member. In some cases, such windings may be encapsulated by the structure of the cover member 1875. As illustrated in the end view of FIG. 18C, the cover member may be formed in several portions, such as 2, 3, 4 or more portions, e.g., left cover member 1875L half and right cover member 1875R half that split the cylinder longitudinally along its length, to permit the coils to be applied to the sections of the cover member 1875 and otherwise simplify the assembly of the vent. The portions may be joined such that the inner vent member is held within the portions. The joining of the portions of the cover member may then serve to maintain the inner vent member for rotatable operation.

In operation, the inner vent member 1870 may be magnetized such that it may have poles on opposing longitudinal sides of the tube shown as N-mag and S-mag in FIG. 18B, which may depend on the number of coils 1899 of the cover member 1875. For example, in the assembly embodiment illustrated in FIGS. 18A, 18B and 18C, the inner vent member 1870 is magnetized in a plurality of sections that form two halves. However, as illustrated assembly of FIG. 18D, the inner vent member is magnetized in additional sections to complement the additional coils. As shown in FIG. 18D, the cover member includes three coil grooves 1891, three coils 1899 and the inner vent member is magnetized with sections having six poles (e.g., alternating S and N). Such an embodiment of the cover member may optionally be formed in thirds that split the cylinder longitudinally along its length. Of course, different numbers of coils may be utilized.

With such constructions, the inner vent member, shown as a tube with bore 1880 and vent portions 1890, has several magnetic poles. The outer cover member's coil windings may then be energised (e.g., by applying an electrical current) to create one or more magnetic field(s) depending on the number of coils. Optionally, the inner vent member may be coupled to the cover member with a biasing means 1897 (e.g., a spring mechanism) so that the rotation of the inner vent member may be biased to return to an initial position (e.g., open, closed or partially open) if the device is not powered. By controlling the current into the inductive winding, the generated magnetic field(s) acts on the magnetised poles of the inner vent member to cause it to move or shift (e.g., rotate) due to an attraction and/or repulsion force. The strength of the generated magnetic field may be regulated to control the amount of rotation. The rotation then results in the covering or opening of less or more holes depending on the rotating tubes vent area configurations and can thereby permit variable venting.

Figure 27A:
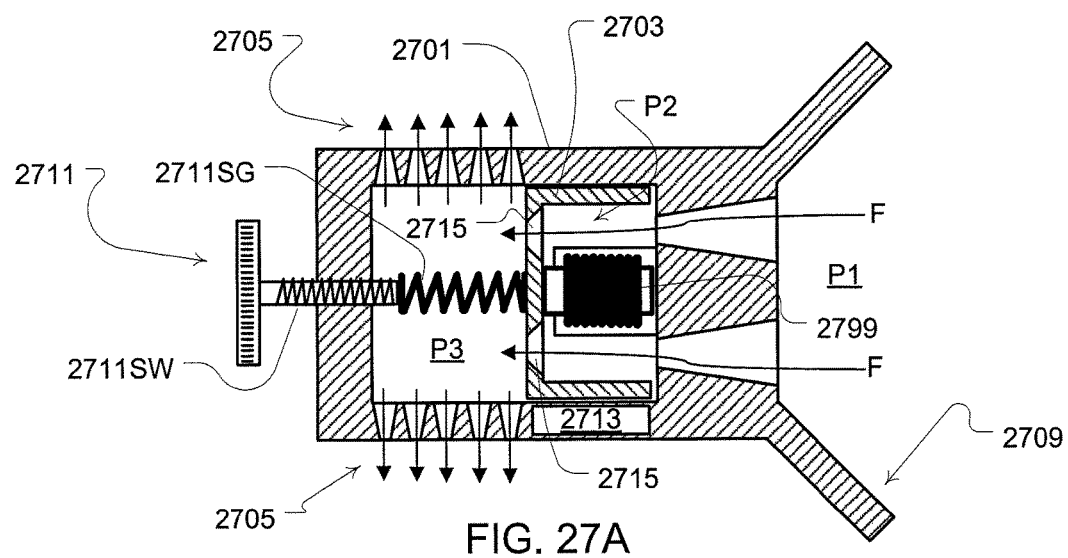
FIGS. 27A and 27B show a cross sectional illustration of a mask assembly including a variable area vent in an open and partially closed position respectively.
Figure 27B:
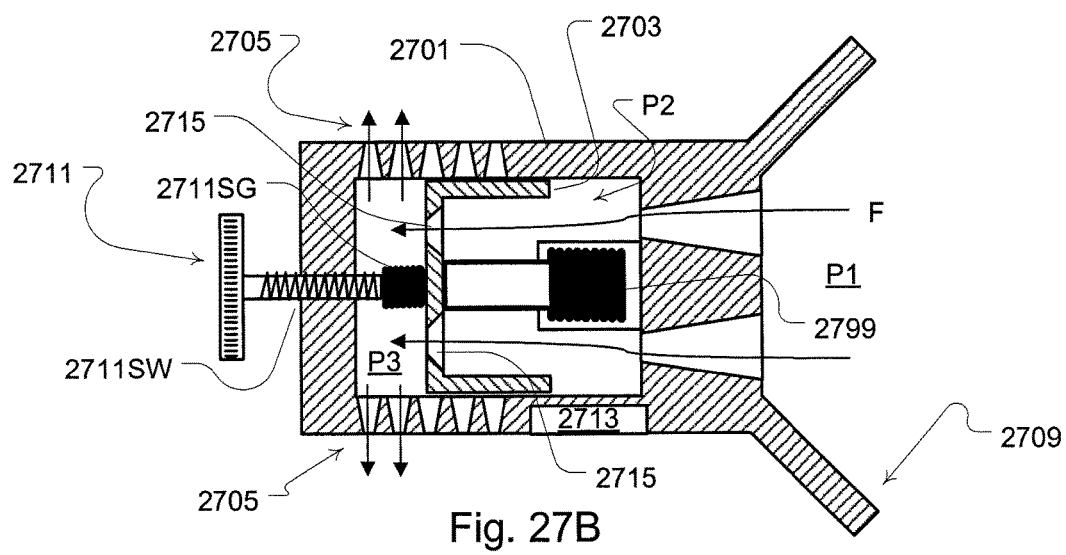

In another vent assembly arrangement, a sealed solenoid may be implemented within an expiratory chamber of mask assembly as illustrated in FIGS. 27A and 27B to form a variable area vent. An expiratory chamber P3, which may be formed by a cylindrical mask assembly 2701, included a piston 2703. The expiratory chamber includes venting apertures 2705 providing openings to atmosphere from the expiratory chamber P3. Optionally, the hole of each venting aperture may be a fine hole, such as an opening with a diameter of approximately 0.4 mm to 1 mm, such as 0.7 mm. The piston is slideably engaged within the chamber to selectively block one or more of the venting apertures. The piston may be configured to form a piston chamber P2 through which expiratory flow F will pass originating from a user at a user side chamber P1 of the mask 2709. To this end, the piston also includes one or more piston apertures 2715 to permit the expiratory flow to pass through the piston. The coil 2799 may be controlled to selectively adjust the position of the piston within the expiratory chamber P3 and thereby selectively cover more or less of the area of the venting apertures 2705. An optional manual adjustment mechanism 2711, such as a threaded post (e.g., screw 2711SW) and biasing member (e.g., spring 2711SG) may be fixed to the piston to tension and/or limit an extent or range of movement of the piston. Such a manual adjustment may be implemented for manual setting of a minimum open area of the vent. An optional position sensor 2713 may provide feedback to a controller (not shown) for selectively controlling current to the solenoid coil for positioning of the piston. As illustrated in FIG. 27A, the piston may be controlled to be in an open position such that a greater venting area is available for expiratory flow. In FIG. 27B, the piston may also be controlled to move by an electro-magnetic field to slide over a portion of the venting area of the venting apertures 2705 so as to provide a lesser venting area of expiratory flow.

In some configurations of FIGS. 27A and 27B, the solenoid may be omitted. In such a case, the vent area may be manually adjusted by the adjustment mechanism, which may omit the spring, so as to move the piston to a desired venting position. Similarly, in some configurations the manual adjustment mechanism may be omitted and vent area adjustment may be implemented solely with the control of the solenoid.

One advantage of the vent assembly of FIGS. 27A and 27B involves the multiple chambers labelled as P1, P2 and P3. With multiple chambers, expiratory venting noise may be reduced. The chambers provide several levels of gradual pressure drop (e.g., from P1 to P2, from P2 to P3 and from P3 to atmosphere) that can reduce venting noise.

Figure 28A:
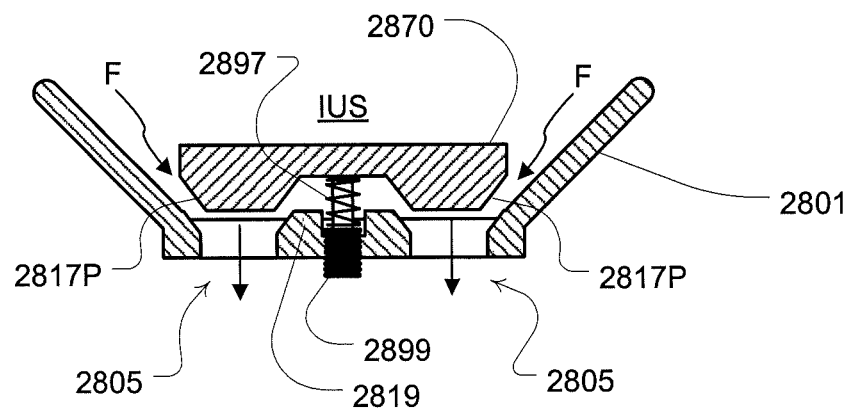
FIGS. 28A and 28B contain a cross sectional view of a further embodiment of a mask assembly including a variable area vent in an open and partially closed position respectively.
Figure 28B:
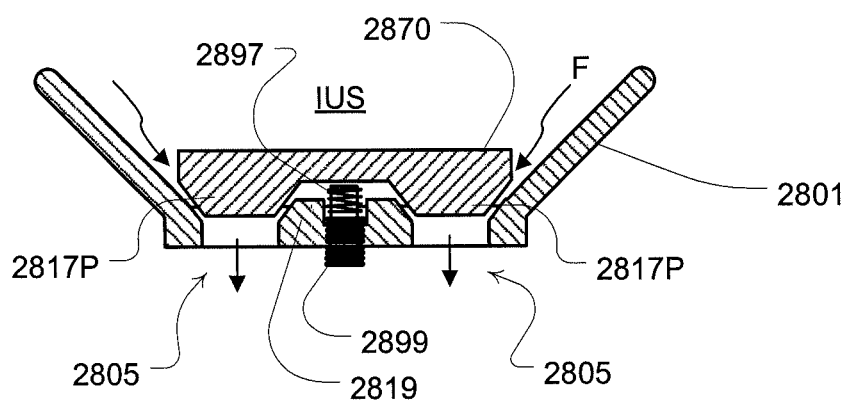
Figure 29A:
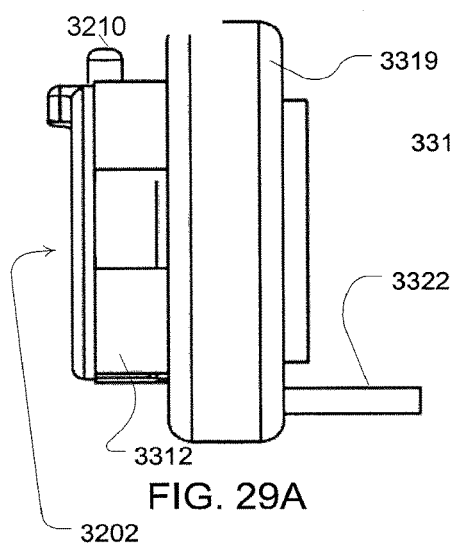
FIG. 29A is a side view of a variable area vent embodiment including an adjustable iris and controller mechanism.
Figure 29B:
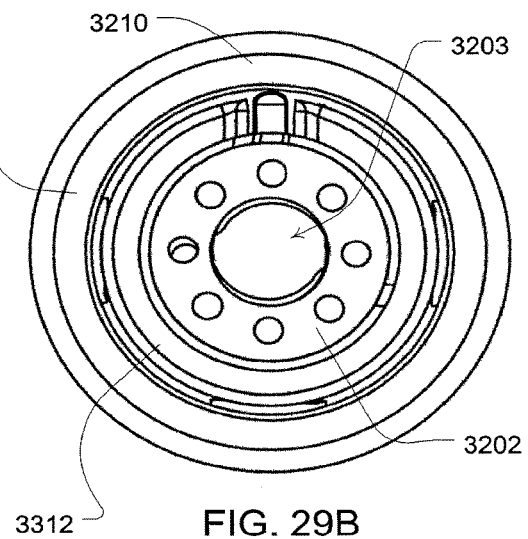
FIG. 29B is a front view of the embodiment of FIG. 29A.
Figure 29D:
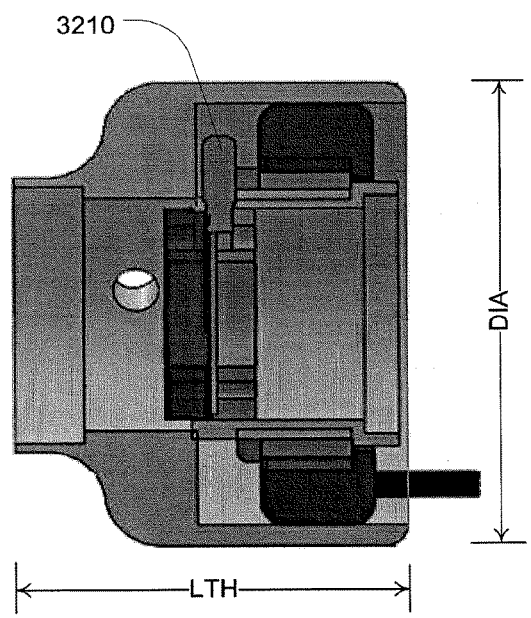
FIG. 29D is a side cross section view of a variable area vent embodiment of FIG. 29A within a housing.
Figure 29C:
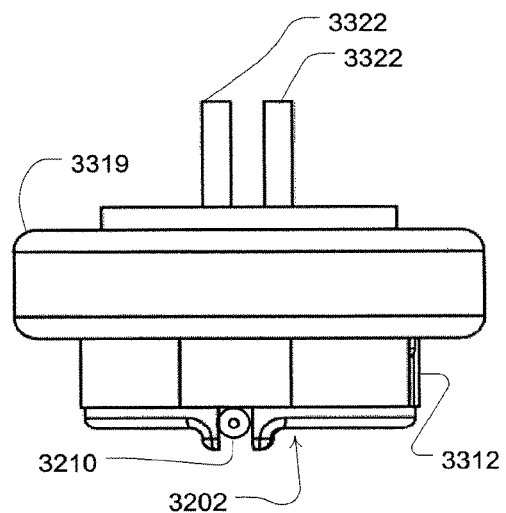
FIG. 29C is top plan view of the embodiment of FIG. 29A.

Another mask assembly 2801 that may be configured as an adjustable vent for variable area venting is illustrated in FIGS. 28A and 28B. An inner vent member 2870 may be on an inner user side IUS of the mask assembly 2801. The inner vent member may be selectively positioned to block, by variable degrees, the venting apertures 2805 of the mask assembly. In this regard, the inner vent member may include one or more projections, such as plugs 2817P, that include a profile or contour to complement the contour of the venting apertures. For example, the projections may be formed by a conic shape and the apertures may be formed with a funnel shape so that the conic shape may be moved to extend within or withdraw from the funnel shape to limit the flow through the funnel to greater or lesser degrees. Other shapes of the projections and apertures may also be implemented so as to permit varying of the flow through the apertures.

As shown in FIGS. 28A and 28B, movement of the inner vent member 2870 may be controlled by a solenoid with a coil 2899. Alternatively, the solenoid may be replaced by a stepper motor that may turn a threaded post coupled between inner vent member 2870 and an actuator support 2819 of the venting portion of the mask assembly 2801. Optionally, a biasing member 2897, such as return spring, may bias the inner vent member 2870 to either an open or closed position. Thus, movement of the vent member, such as by a slug or piston of the solenoid, will either compress or stretch the spring. For example, in the case that the biasing member biases the inner vent member to an open position, a lack of power to the coil will keep the inner vent member in an open position as illustrated in FIG. 28A to permit a maximum expiratory flow through the venting apertures from the user side. By controlling a supply of current to the solenoid, or to the stepper motor, the inner vent member may be moved closer to the venting apertures to varying degrees to reduce the area of the vent and thereby reduce the expiratory flow F from the user side of the mask assembly.

An advantage of the vent assembly of FIGS. 28A and 28B is that portions of the control unit (e.g., the solenoid and/or stepper motor, may reside outside of the mask. As such, they may be easily removed for maintenance or replacement.

A further venting assembly that may be implemented as a variable area vent is illustrated in FIGS. 19A and 19B. The cover member 1975 may be implemented with a plurality of flexible or pivotal flaps 1975F. The flaps may be attached along one edge to an inner vent member 1970 which may form the pivoting edge of the flap. The inner vent member 1970 may include holes to form vent portions 1990 shown under or between flaps 1975F. The inner vent member 1970 may also include one or more conduits for one or more electro-magnetic coils 1999. For example, each flap 1975F may be associated with its own coil 1999. The flaps may operate to permit a flow F to pass through the inner vent member and between the venting aperture 1995 formed by spaces between the flaps 1975F of the cover member 1975. The application of a current to a coil 1999 may generate an electro-magnetic field to magnetically attract a magnetic portion of a proximate flap 1975F to draw the flap to pivot or flex to close over an aperture of vent portion 1990 of the inner vent member. In such a way, the flap may be operated to prevent or impede flow through the inner vent member proximate to the flap as illustrated in FIG. 19A. Absence of such an applied current may permit a flow F to pass through the inner vent member 1970 and pass by a flap 1975F of the cover member 1975. Optionally, the coils may be activated by a common current to permit all flaps to close in the same operation. However, alternatively the flaps may be selectively activated by selective activation of one or more coils or sets of the coils 1999 (e.g., one by one) to thereby permit the vent open area to be varied as increasing subsets of flaps are opened or closed.

The flap may be formed of a magnetic material or may have portions that are magnetic. For example, a magnetic flap edge MFE may be formed along the flap of a magnetic material on an edge opposite the pivot flap edge PFE which may be formed of a non-magnetic material such as a flexible plastic or polymer (shown in 19A). Although FIG. 19B illustrates opening of the vent by raising the flaps, alternatively raising the flaps by magnetic control may serve to block an aperture or channel through the vent.

Additionally, a movable fabric portion or threads of a fabric may serve to regulate flow through an area of a vent. For example, a porous fabric may be applied to cover a portion of an inner vent member. Application of a magnetic field or physical stimuli or other mechanical movement of the fabric (e.g., stretching) may modify the fabric's flow characteristic or porosity for modifying the transfer of air through the fabric. For example, as illustrated in FIGS. 20A, 20B, 21A and 21B, the fabric may have moveable threads or layers for controlling the flow. As illustrated in FIGS. 20A and 20B, layers of a fabric, that may optionally have an airfoil shape, may be moved to permit flow through the fabric. As shown in FIG. 20A, when the layers are upright the fabric may have an increased flow characteristic. As illustrated in FIG. 20B, when the layers fall or lie down, the fabric may have a decreased flow characteristic. Similarly, in the version of the fabric of FIGS. 21A and 21B, threads, such as metallic threads that may be selectively exposed to one or more magnetic fields, may rise and fall to selectively increase or decrease the flow characteristic of the fabric.

Figure 30:
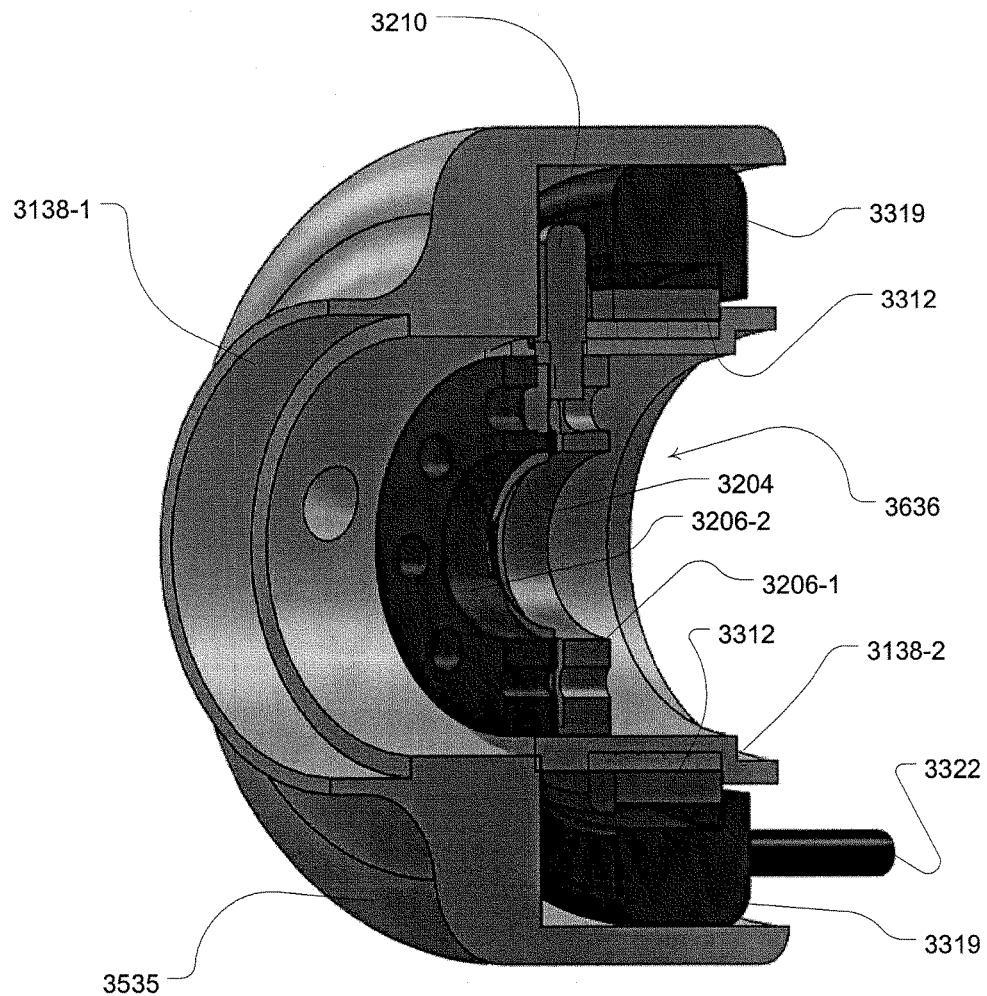
FIG. 30 is an cross sectional perspective illustration of an adapter housing with the mechanism of FIG. 29A.
Figure 31:
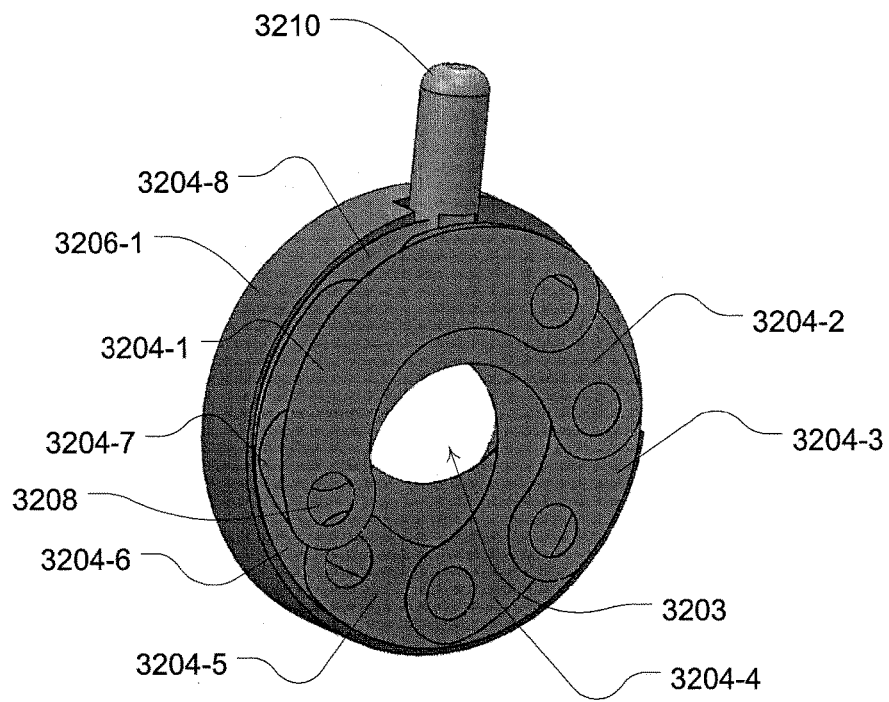
FIGS. 31 and 32 are isometric perspective view illustration of components of an iris assembly.
Figure 32:
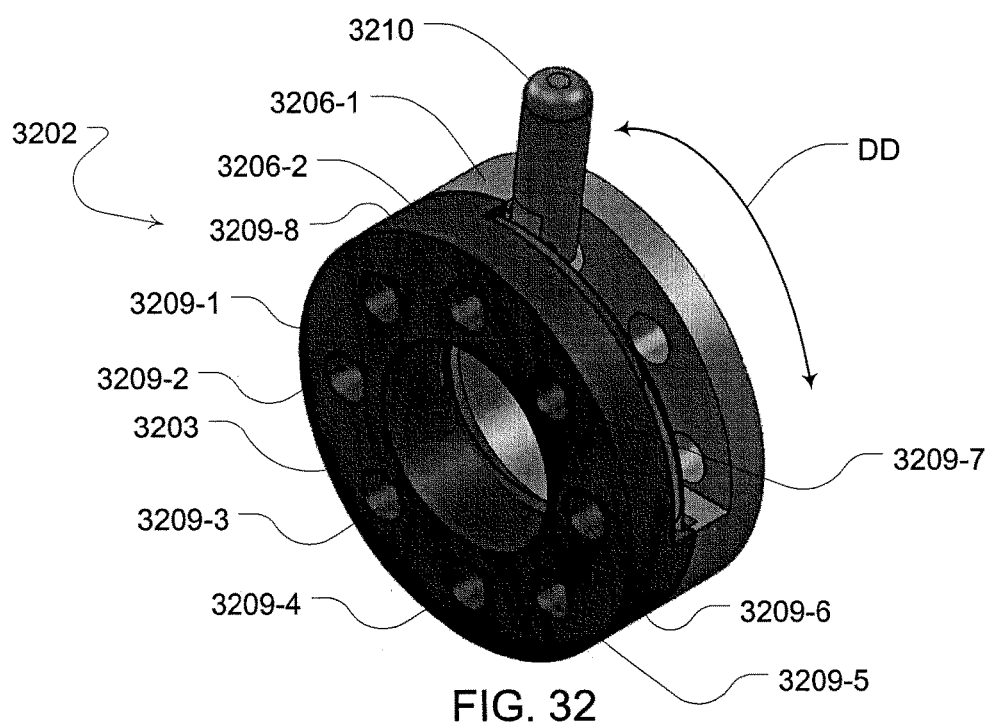

As illustrated in FIGS. 29A through 35, variable venting may employ an adjustable iris. As best seen in the illustration of components of FIGS. 31 and 32, an iris assembly 3202 may serve as a diaphragm with an adjustable aperture 3203. Blades 3204-1, 3204-2, 3204-3, 3204-4, 3204-5, 3204-6, 3204-7, 3204-8, may be rotatably mounted between first and second blade mounts 3206-1, 3206-2 to form the aperture. As illustrated in FIG. 31, the blades may be curved and implemented in an overlapping configuration such that their generally flat planar surfaces are, at least in part, in contact with each other. Each blade may rotate about a pivot pin (not shown) that is inserted near the end of the blade through a pivot aperture 3208 of the blade. These pivot pins are further engaged in apertures 3209-1, 3209-2, 3209-3, 3209-4, 3209-5, 3209-6, 3209-7, 3209-8, of the second blade mount 3206-2. Generally, the narrow edges of the blades do not contact each other. Rather, the surfaces of each blade may be slidingly engaged with the surfaces of one or two other blades. It is to be understood that the number of blades 3204 utilized may be varied, for example to use 2, 3, 4, 5, 6, 7, 8, 9 or more blades 3204.

An iris drive lever 3210, which may be formed as part of the blade mount 3206-1, is pivotably coupled with all of the blades so as to serve as an actuator for the adjustment of the aperture 3203 formed by the blades. When the drive lever is traversed in directions of arrow DD shown in FIG. 32, the blades rotate to permit either an increase or decrease in the size of the adjustable aperture 3203 formed by the blades. This actuated movement of the drive lever rotates each blade toward (or away from) the center of the adjustable aperture 3203 of the iris. Thus, the drive lever motion selectively prevents (or permits) air flow. This also selectively allows varying degrees of air flow through the iris depending on the position of the drive lever.

Accordingly, when the iris assembly is inserted in an exhaust venting component, such as a port of a mask or other conduit, a manual adjustment of the drive lever may be made to set a desired level of airflow through a vent employing the iris assembly. However, in arrangements, such as illustrated in FIGS. 29A to 29D, the iris assembly may be implemented with further actuator components for a more automated control over the drive lever, and thus, an automated control over the varying size of the adjustable aperture 3203.

Figure 33:
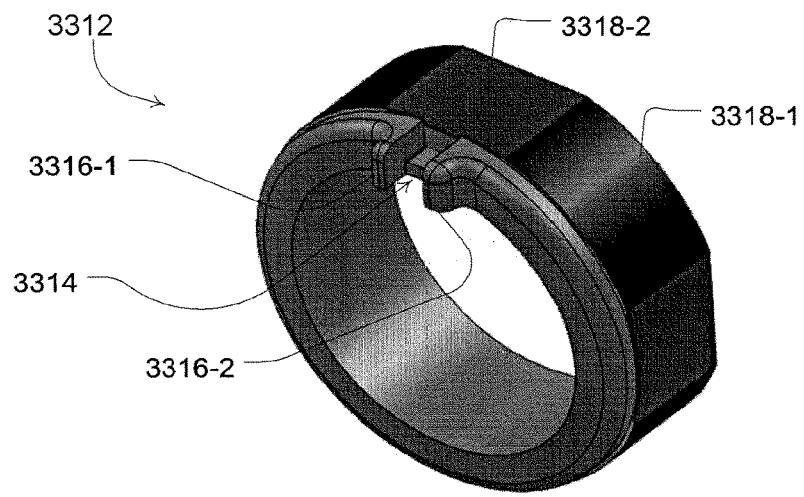
FIG. 33 is an isometric perspective illustration of a magnetic yoke assembly for the mechanism of FIG. 29A.

For example, the iris assembly may be fitted with a yoke 3312. As shown in FIG. 33, the yoke 3312 may be adapted as a ring. Optionally, the ring may be formed of a magnetic and/or plastic material. The yoke may include a drive lever catch 3314, such as one with a set of projections 3316-1, 3316-2, to ply against the drive lever when the iris assembly is inserted within the yoke 3312. The peripheral surface of the yoke may be formed to have magnetic sections 3318-1, 3318-2, or applied magnets, so as to form a set of magnetic sections around the periphery of the ring with alternating magnetic poles. The number of sections may be chosen as desired depending on the range of movement desired for the yoke. For example, a two pole configuration, a four pole configuration, etc., may be implemented.

Figure 34:
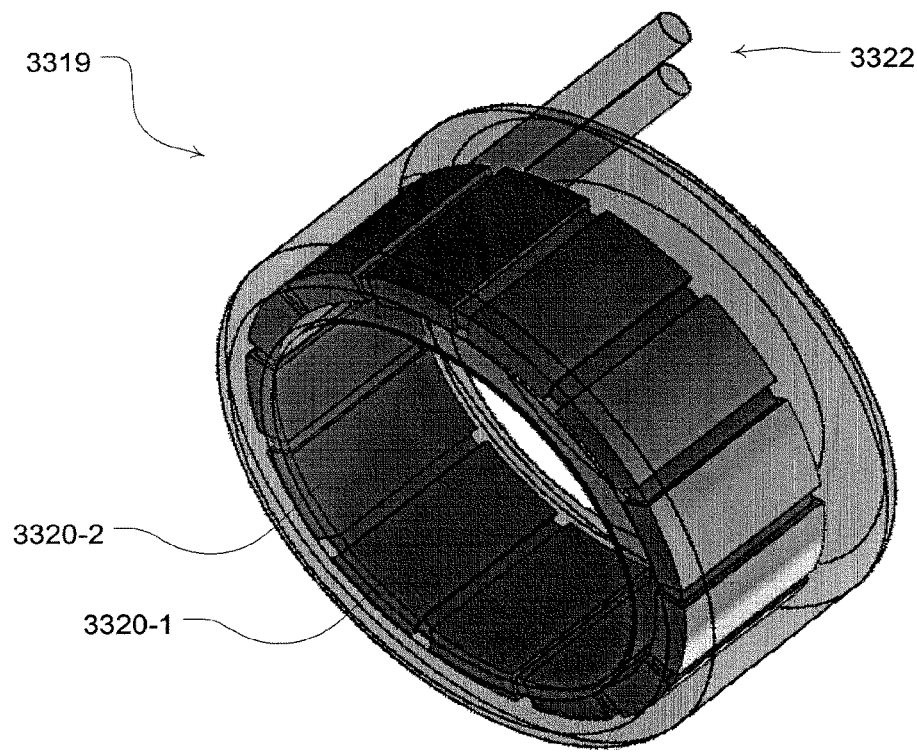
FIG. 34 is an isometric perspective illustration of a control coil assembly for the mechanism of FIG. 29A.

The yoke ring may be rotatably mounted within a control coil ring assembly, such as the coil assembly 3319 illustrated in FIG. 34. The control coil ring assembly may typically include a set of coils 3320-1, 3320-2, such as in a ring formation. Thus, the coils may be located about the periphery and be proximate to the internal surface of the control coil assembly near to where the yoke ring may be positioned. The field coils may be selectively powered by a controller with a set of leads 3322. Accordingly, selective powering of the coils by a controller may permit selective rotation of the yoke (in directions of arrow DD shown in FIG. 32) due to the magnetic forces of the field coils and magnetic sections of the yoke. For example, the yoke and coil assembly may be configured to permit approximately a 90 degree range of motion of the yoke within the coil assembly. As such, the yoke 3312 may then be controlled to move the drive lever in a slot of the yoke via the drive lever catch 3314 when the iris assembly is installed within the yoke. As such, the control of the powering of the field coils may selectively control the size of adjustable aperture 3203, and thus, control the venting flow through the iris. In this regard, the airflow of the vent may pass through the open aperture formed by the blades and will also travel through the rings formed by the coil assembly and yoke. In some example implementations, a controller or processor of a respiratory treatment apparatus may control a vent flow with such an iris using any of the control methodologies described in more detail herein.

Optionally, in some embodiments, the yoke may employ one or more biasing members to bias the yoke in a certain position. For example, the yoke may be biased by one or more springs such that the biased position of the drive lever in the yoke will settle the iris assembly in a fully open position. Powering the coils may then serve to move the iris assembly away from its spring biased position and against the biasing force toward a more closed position. In the absence of any power to the coils, such a biased iris assembly will return to a fully open position as a result of the biasing force of the biasing member (e.g., spring). Similarly, the yoke may be biased by one or more spring components such that the biased position of the drive lever in the yoke will settle the iris assembly in a fully closed position. Powering the coils may then serve to move the iris assembly away from its spring biased position and against the biasing force to a more open position. In the absence of any power to the coils, such a biased iris assembly will then return to a fully closed position as a result of the biasing force of the spring.

Still further, a spring component(s) may be employed to bias the yoke and the position of the drive pin in the yoke so as to settle the iris assembly in a half open/half closed position. Selectively powering the coils may then serve to move the iris assembly away from its spring biased position and against at least one biasing force to either move toward a more open position or toward a more closed position. In the absence of any power to the coils, the iris assembly will return to a half open/half closed position as a result of the biasing force(s) of the spring components.

As illustrated in FIGS. 30 and 35, the iris assembly and control mechanism (e.g., yoke and control coil assembly) may be inserted in a housing 3535 that may serve as part of a conduit of an exhaust vent or a washout vent for a mask. For example, as shown in FIG. 35, a housing 3535 may couple with the iris mechanism 3636 to regulate flow of air through a conduit 3537 of the housing. Optionally, as shown in FIG. 30, the housing 3535 with the inserted iris mechanism 3636, may itself be formed as a conduit adapter. Thus, air delivery conduits may be coupled to the housing 3535 so that the iris mechanism may control flow through the conduits connected by the adapter. In such a case, adapter openings 3138-1, 3138-2 may serve as couplers for additional conduits (e.g., air delivery tubes, for example, by an interference fit between the openings and the conduits. In some cases, the iris mechanism with its yoke and coil assembly may be sized for insertion within an exhaust port of a patient mask so as to serve as a washout vent. For example, the length of the diameter line DIA of the adapter assembly of FIG. 29D may be 15 mm to 30 mm such as about 22 mm and the length shown by line LTH may be 12 mm to 25 mm, such as about 17 mm. Thus, the diameter of the iris mechanism itself may be less than 22 mm and its length may be less than 17 mm. Such a component size may permit its use in a mask without causing the mask to be too large. As such, it may be more comfortable for patient use while sleeping.

In FIG. 1, the vent assembly 60, 360, 460 may further include one or more sensors, such as a pressure sensor or flow sensor to measure the flow or pressure for use in the control of the vent. For example, pressure of the mask may be measured and used as a function to control the vent. Similarly, flow in or through the vent may be measured and used to control the vent. Moreover, a measure of patient flow may be applied as an input to a function for making control changes to the vent. Optionally, a position sensor may be implemented to sense the relative position of the vent member and the cover member. Based on one or more of such sensors, the venting characteristics of the vent may be evaluated during operation, such as by the controller or processor of the flow generator.

Communication between the flow generator processor 40 and the vent assembly actuator and sensors may be through dedicated wires, or alternatively may be multiplexed with other sensor wires or multiplexed with the tube heater wires or inductively coupled to the heater wires. Alternatively, communication may be by wireless communications, such as with a Bluetooth link.

The actuator assembly may also include an infrared light that pulses infrared light rays in the direction of the vent assembly. The vent assembly may reflect the infrared light ray back to the actuator assembly where a microprocessor then calculates the time delay between emitting the infrared light and receiving the reflected infrared light. The time delay may be taken as an indication of the position of the vent assembly. Alternatively, the reflectivity may be measured such as by the amplitude of the received light, which may then be implemented as an indicator of the vent position where different amplitudes are associated with different positions of the vent. Once the position of the vent assembly is known, a processor of the flow generator may be configured to calculate the pressure and/or flow at the mask and adjust the settings of the flow generator accordingly. In addition, the actuator or motor may adjust the position of the vent assembly if the flow generator calculates that an alternative vent position is required.

Control of Vent Flow

The variable area vent arrangement of the current technology may improve the control of gas washout. This, in turn, may permit improved patient treatment and/or functioning of a respiratory treatment apparatus. For example, the vent may be operated to achieve a more instantaneous response with a flow generator to conditions at the mask. It may be operated with the flow generator to achieve faster rise and fall times. In some cases, operation of the vent can permit use of a blower that operates with a single pressure while still allowing the pressure at the mask to be varied by controlling changes to the venting area. In some cases, the changes in vent conduit impedance may also allow for an adjustment to the pressure levels in the mask. For example, the conduit embodiments of FIGS. 14 and 15 may be coupled to an output of a vent. As such, changes in the conduit impedance that may be made by manipulation of the flow control slug can thereby change the pressure at or flow of the vent.

Figure 6A:
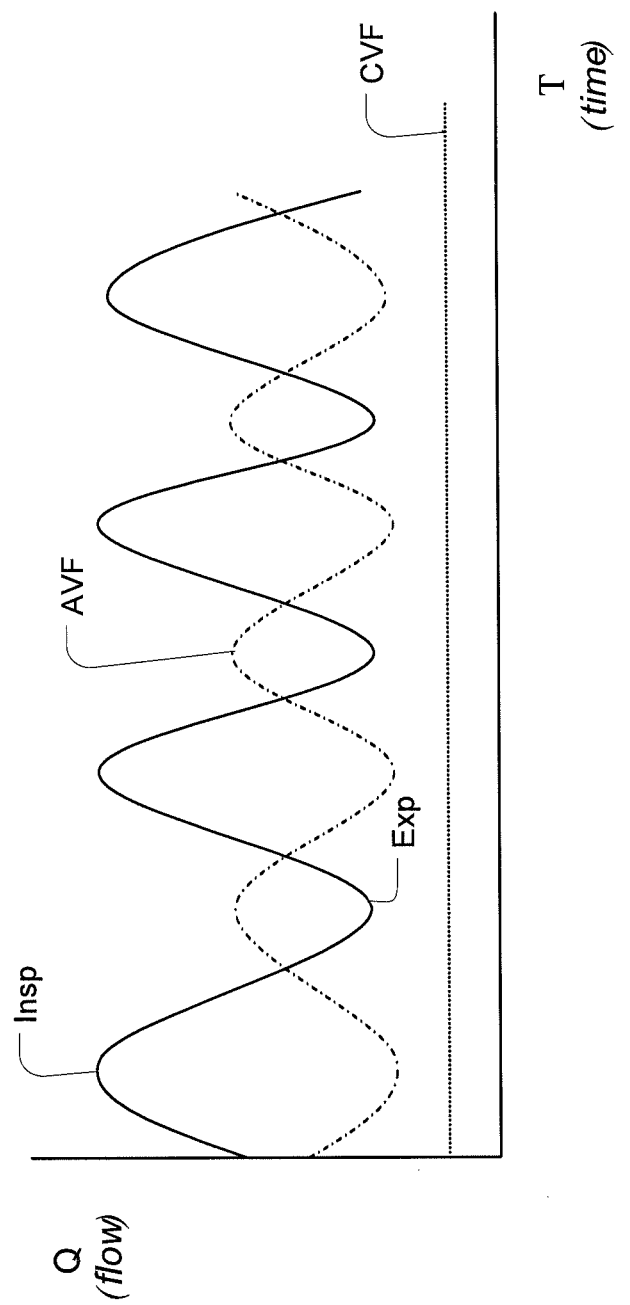

For example, control of the vent area may be implemented in synchronization with a patient's breathing cycle so as to participate in the pressure treatment of the patient. For example, the actuation of the active vent may be implemented so that the vent flow mirrors the flow of the patient's respiratory flow cycle as illustrated in FIGS. 6A and 6B. As illustrated in FIGS. 6A and 6B, the vent flow is out of phase with patient respiration. Thus, a minimal vent flow may be set for peak inspiration so that the patient may inhale more of the gases from the flow generator (as opposed to a typical non-adjustable gas washout vent where some of the gas from the flow generator passes straight out of the vent), and a maximum vent flow may be set for peak expiration. As illustrated in the graphs, different functions (e.g., sinusoidal function, shark-fin function, etc.) may be implemented for setting the change in amplitude of the vent flow.

Optionally, the control of the venting area and the resulting vent flow could also be phased or timed depending on the sleep state of the patient (e.g., whether they are awake, sleeping, etc.). For example, when the patient is awake (e.g., trying to get to sleep) the vent may be controlled to operate in a more open or higher flow position in cooperation with the flow generator, such as a higher flow position held approximately constant over the patient's breathing cycle, so that there is less impedance when the patient inhales. As the patient enters a sleep state, the controller of the system may then initiate operation of the vent so that it functions in the manner illustrated in FIG. 6A or 6B. Optionally, if the device then detects an awake state or non-sleep state, the vent may be controlled to return to operate in the higher flow position in cooperation with the flow generator, such as the more constant higher flow position. A determination of sleep state may be made by any suitable process but may in some embodiments be made in accordance with the sleep condition detection technologies described in PCT Patent Application No. PCT/AU2010/000894, filed on Jul. 14, 2010, the disclosure of which is incorporated herein by reference.

The control of the vent may be implemented in response to detected patient conditions, such as sleep disordered breathing events. For example, an analysis of flow and/or pressure data by a processor of the controller of the flow generator may detect respiratory conditions such as central or obstructive apnea, central or obstructive hypopnea, and/or snoring etc. Example methods for detecting such conditions are described in U.S. patent application Ser. No. 12/781,070, filed on May 17, 2010, the entire disclosure of which is incorporated herein by reference. The controller may then set the vent area based on the analysis of the patient's detected condition. For example, if a central apnea is detected (an open airway apnea) or a central hypopnea, the processor may control the vent to close or reduce the vent area so that the patient is permitted to re-breath $CO_2$. This may induce the patient's brain to detect an increase in $CO_2$ in the body and thereby cause the patient to spontaneously breath. Thereafter, if the controller detects a patient's breath or if a safety time period lapses without a breath, the vent may then be controlled to return to its normal operation, such as that associated with the varied operation of FIG. 6A or FIG. 6B or a more constant open position that provides a required vent flow during respiration. Beneficially, pressure or flow adjustments that are attributable to changes of the vent area may take effect faster than such changes controlled by adjustments to some flow generators. Thus, an initial adjustment of mask conditions by manipulation of the vent may be performed before flow generator changes are implemented. This may provide the controller of the flow generator an opportunity to determine with its sensors how a patient's airway is reacting and/or how the flow generator should thereafter respond.

Furthermore adjustments to the venting area may be implemented to improve patient comfort or to offset a potential leak due to an improperly positioned mask. Essentially, these procedures may permit adjustments to the position of the patient's mask. For example, the controller of the flow generator may detect an occurrence of an unintentional leak that may be attributable to a displaced positioning of the mask. If such a leak is detected, the controller may control an adjustment to the vent area such as to close or rapidly close the vent assembly. Optionally, such a closing of the vent may be joined by a simultaneous controlled increase in speed of a flow generator to temporarily increase airflow or pressure delivered to the mask. The pressure increase at the mask resulting from the closing of the vent assembly may then cause the mask to 'jump', shake or disrupt from the patient's face. This jump or movement of the mask may result in the mask re-positioning its seal to the patient's face and potentially sealing the detected leak path.

As an alternative controlled approach, the controller may then control the vent arrangement to open (and/or simultaneously control a reduction in generated pressure by the flow generator) so that the pressure of the mask is substantially reduced (e.g., to a pressure or atmospheric pressure) for some predetermined period of time. This substantial reduction of pressure in the mask may then allow the mask to be re-positioned by some movement of the patient or allow the mask to change in the case of an auto adjusting mask and thereby potentially correct the seal issue. Optionally, this controlled opening approach may be implemented subsequently to a prior 'jump' attempt previously described, in the event that mask leak is still detected after the 'jump' attempt. Such controlled procedures may be repeated or performed (in any order) until the leak is no longer detected or for a predetermined number of times. Moreover, both opening and closing the vent may be repeated rapidly and may coincide with the flow generator decreasing and increasing the pressure respectively. Such a shaking process may result in the mask vibrating to a degree to help in reset the mask position to rectify the detected leak.

Other vent area control procedures may also be implemented in response to leak detection, such as the detection of unintentional leak, performed by the controller. For example, the degree of venting may be variably controlled as a function of a detection of unintentional leak and/or mouth leak (such as in the case of a nasal only mask). Consequently the pressure and flow output from the flow generator may be determined. Additionally, the vent leak may be calculated by sensing pressure or flow at or near the vent assembly. The difference between the air flow generated by the flow generator and the vent leak flow may be determined to be the sum of unintentional leak and mouth leak (where applicable). Mouth leak may be determined, for example, as described in U.S. Provisional Patent Application No. 61/369,247, filed 30 Jul. 2010, the entire disclosure of which is incorporated herein by reference. Thus, the unintentional leak flow may be calculated. (e.g., $Flow_{unintentional\_leak} = Flow_{total\_generated} - (Flow_{mouth\_leak} + Flow_{vent\_leak})$)

The vent area of the vent assembly may then be controlled based on such a determination of unintentional leak quantity by the processor of the flow generator. In one example, upon the flow generator processor determining increased or excessive unintentional leak, such as by a comparison of the quantified leak to a threshold that may be indicative of a required gas washout flow, the processor may control the vent actuator to reduce the vent open area, since less gas washout venting is required with increased unintentional leak at the patient's face. Similarly, if such a leak is no longer detected, the processor may thereafter control an increase to the vent open area so that the flow of the gas washout vent satisfies a required gas washout flow.

Furthermore, by knowing the open area against pressure characteristic for the vent assembly, the processor may control the vent actuator based on the sensed or calculated pressure at the vent, to control the vent flow to remain constant or to follow a predetermined pattern.

Additionally, the venting may be controlled in response to the patient's breathing cycle or therapy need.

Algorithms for determining cycling between inhalation and exhalation are known, and described for example in US Patent Application 2008/0283060, filed 21 Dec. 2006. By employing such an algorithm, the variable area vent controller may be controlled to synchronise with the breathing cycle, for example to reduce the vent open area or close the vent completely during part of the patient's breathing cycle. For example, the vent area is reduced or closed at a time corresponding to inhalation when gas washout is not required, and is opened coinciding with patient exhalation.

By reducing gas venting during inhalation, it is believed that the mean and peak flow rate required to be generated by the flow generator may be reduced, with resultant decreases in flow generator capability and size, air delivery conduit diameter and humidifier capacity being possible. Furthermore, the power and water consumption of the apparatus may be able to be reduced.

The actuation of the active vent may be controlled by software. The software may be upgradeable or re-settable in accordance with particular patient's needs or clinical direction. For example, a patient (e.g., a patient suffering from Cheyne-Stokes respiration CSR) may have a first vent flow requirement during their first period of treatment (e.g., first month, first week, first year, number of days, etc.) and then have a second vent flow requirement in a second period of treatment (e.g., the second month, second week, second year, a following number of days respectively). The software may control this change of the vent flow setting according to the particular period (e.g., year) by checking an internal clock and adjusting the setting accordingly. Alternatively, the data of the software may be upgraded to re-program the active vent in the second period of treatment to cause the vent to achieve the second vent flow requirement. As discussed in more detail herein, controlled adjustments to the vent may also be made during a treatment session and may depend on detected patient conditions such as sleep stage or time in treatment. Moreover, vent adjustments may also optionally be made based on blood gas measurements or surrogates thereof, such as from a transcutaneous pCO2 sensor, of the patient during treatment. For example, a controller may reduce vent size to cause re-breathing of $CO_2$ upon detection of lower than normal paCO$_2$ relative to one or more thresholds. The controller may then return the vent size for normal $CO_2$ washout when the blood gas measurements normalize.

In some cases, an anti-asphyxia valve may no longer be necessary. The active vent could also serve as an anti-asphyxia valve. For example, when the vent includes a biasing member. The biasing member may maintain the vent in a normally open position for breathing through the vent if the controller is not powered and/or operating the flow generator. When under power and operating, the controller may then control the vent to limit vent flow to any desired $CO_2$ washout level.

Patient compliance with OSA therapy such as CPAP and APAP is affected by many factors. One of the significant factors affecting success of an OSA patient remaining on effective therapy is the level of comfort associated with the wearing of the device and mask during the period while still awake. If the patient comfort can be paramount until the onset of sleep then there is likely to be an increased compliance with CPAP or APAP therapy overall. Similarly, the patient may resist continuation of therapy if woken for any reason during sleep. The awakening may be unrelated to the patient condition, for example the arrival home of another family member may wake the patient. Once awake, the patient may suffer discomfort and remove the CPAP system.

One factor that may decrease patient comfort, especially when not sleeping or in an aroused state, is the potentially low pressure during wake state of an APAP machine. Typically an APAP machine uses low pressure when the wearer is not experiencing an occluded airway. For fixed aperture vented mask systems the low pressure also will result in a low intentional leak (or vent) flow and may result in decreased $CO_2$ washout. Potentially, the patient may experience some re-breathing, while not significantly of clinical concern it may be sufficiently uncomfortable to the patient and discourage use of the mask system.

Potentially, due to the low washout levels and additionally the level of humidity and heating levels of the air proximal to the patient airways in the conduit and mask, the patient may feel uncomfortable.

During treatment and the period waiting to fall asleep and also during potential arousal events, the patient may suffer a feeling similar to claustrophobia where there is a desire to remove the CPAP/APAP system.

A variable vent system, such as one that employs the conduits and vents previously described, can potentially improve comfort during sleep state periods, including wake, when therapy is not required. For example, a controller of the adjustable vent may detect appropriate sleep related periods of a patient, such as wake, or potentially light sleep. In response to these detections, the controller may then alter the pneumatic, humidity and heat settings set by the controller.

For example, the controller may increase the vent flow when the respiratory treatment apparatus is set to generate lower pressures. Similarly, the controller may decrease the vent flow when the respiratory treatment apparatus is set to generate higher pressures. This may be suitable if these pressure settings contribute to events that may wake or result in patient arousal.

When increasing the vent flow at lower pressures, the APAP/CPAP respiratory treatment device could compensate by increasing the flow supply from the controlled flow generator to maintain the set pressure at the patient interface but with increased flow through the conduit and mask and out the vent. The result is significantly increased $CO_2$ washout at the desired pressure setting.

This controlled adjustment may also result in a change in feeling of the patient as the flows near the facial skin and nasal nares may have a cooling and drying effect. Similarly, reducing the vent flow may increase the feeling of the temperature and moisture content of the air to the patient.

By changing the vent flow, the patient may feel hotter/cooler, and/or moister/drier simply with the changing flow rate of the air near sensitive skin and nasal tissue. Thus, the regulation of vent flow can provide a basis for adjusting patient comfort.

The detection of sleep state may serve as a basis to change the vent flow to improve the patient's feeling of comfort. Similarly, the humidity and delivered air temperature may also be optimised to suit the patient during such conditions in the event that the controller of the respiratory treatment apparatus also controls a humidifier and/or air warming element.

If normal or deeper sleep states are detected by the controller, the prescribed patient therapy (e.g., CPAP and APAP therapy settings), humidity and temperature settings will be set and delivered by the apparatus.

However, comfort changes from the prescribed treatment settings may be set when the apparatus detects light sleep or awake states. The physician prescribed settings during these states may not be necessary since OSA is not likely to occur during such stages of sleep (or awake) states. Thus, patient preferred settings may automatically take effect on the detection of the light sleep or awake states.

Such features as a "ramp" and similar from current CPAP machines do not deliver the prescribed titration level of pressure until the patient is expected to be in the correct sleep state by delaying the delivery of therapeutic pressure levels for a period of time by gradually raising the pressure to the therapeutic level.

A further feature can exploit the lack of need for therapeutic pressures during light sleep or awake states to allow the patient to adjust the flow through the vent during such states. Normal therapeutic settings can resume during usual sleep states requiring it. For example, when the "ramp" feature is engaged, the respiratory treatment apparatus may set the vent flow levels to those specified by some "patient comfort" settings rather than the prescribed therapeutic settings. Thus, the apparatus may have a user interface to allow the patient to input or adjust the "patient comfort" settings (e.g., within permitted ranges) to the apparatus for these controlled features.

As an extension and as part of the "patient comfort" settings, the apparatus may permit the patient to adjust CPAP/APAP pressure within the safe limits that may be set by clinical staff during titration or to some range that may be found to be safe during the detected awake or light sleep periods.

Similarly, as part of the "patient comfort" settings, the patient may be able to have favored humidity and heat settings during such sleep phases that revert to needs based settings in other sleep states.

In some cases, the settings may be automatically controlled or adjusted by the respiratory treatment apparatus based on detected environmental conditions such as temperature and/or humidity outside of the device. For example, cooler settings may be utilized during warmer seasons and warmer settings may be utilized during cooler seasons.

There may be a plethora of settings and/or "patient comfort" profiles of settings that may be preferred by the patient, or even the clinical or prescribing staff. The different profiles even for a single patient may be activated by the device depending on various detected conditions, such as a particular sleep state, environmental conditions, etc.

For example, the apparatus may be configured to activate a particular preferred profile of the air delivery parameters that improve patient comfort at a preferred automatic time or particular sleep state.

Priority in control or profile may be given to comfort, pressure, flow ($CO_2$ washout), moisture, heat, battery or power supply endurance, noise, machine/consumable part life or other system parameter that may be preferred.

In a particular example, an OSA respiratory treatment apparatus may be configured to deliver pressure, vent flow ($CO_2$ washout), humidity/moisture and/or heat to the tastes of the patient as set in "patient comfort" settings by a user interface of the apparatus. Any combination of parameters pressure, flow, moisture and temperature of delivered air may be profiled individually or in any combination. The patient comfort settings then may be activated depending on the particular detected conditions of the machine such as sleep state (e.g., awake or light sleep) and/or environmental conditions. When prescribed therapy is required, such as during detected sleep states, physician prescribed "therapeutic settings" may then be activated such that some or all of the comfort settings will be deactivated.

Cheyne-Stokes respiration (CSR), Complex Sleep Apnoea and other forms of central sleep apnoea may be characterised as (on-average) hyperventilation during sleep. This hyperventilation frequently manifests itself as a lower-than-normal daytime $PaCO_2$. However, it is mainly CHF—or altitude-related periodic breathing with that association—that can be predicted from daytime $PaCO_2$. Complex Sleep Apnoea cannot typically be predicted from daytime $PaCO_2$.

Figure 16:
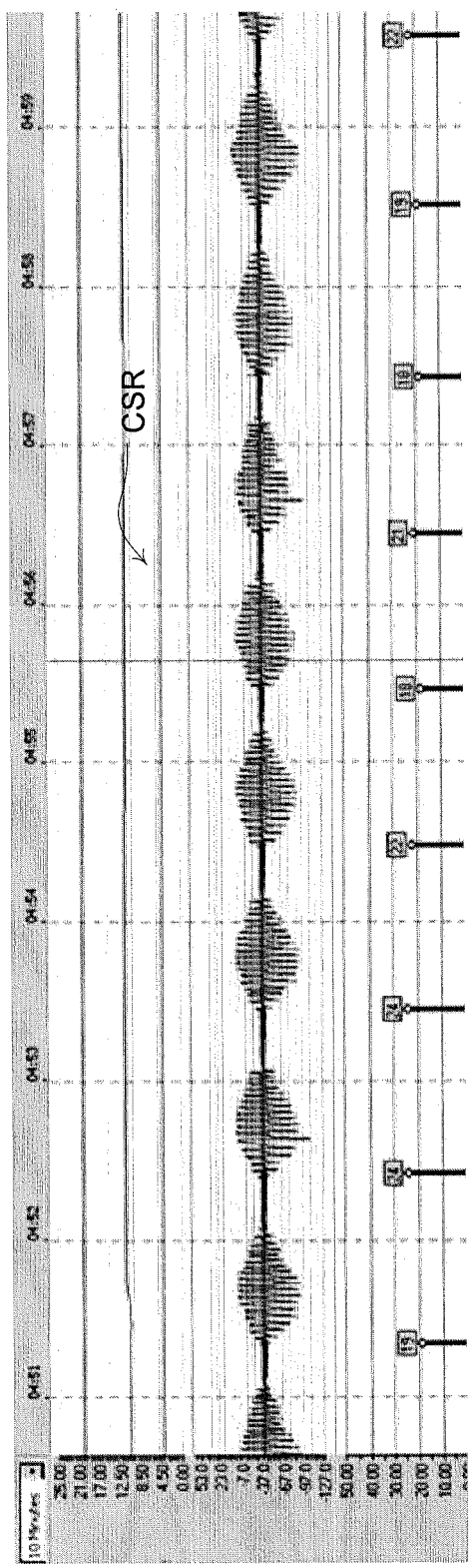
FIG. 16 is an illustration of a Cheyne-Stokes breathing pattern.

The graph of FIG. 16 shows the typical waxing and waning pattern of CSR in a patient getting CPAP treatment from a CPAP respiratory treatment apparatus. The pattern is characterized by periods of hyperventilation (hyperpnoea) interspersed with periods of low ventilation (hypopnoea) or central apnoea. The pattern is strikingly periodic with little variation neither in the length of each cycle nor in the length of the components of each cycle.

Therapeutic methods to return $PaCO_2$ to a normal range have focused on restoring a normal breathing pattern. For example, the ResMed AutoSet CS (or VPAP Adapt) is a non-invasive pressure-control ventilator that stabilises $PaCO_2$ by increasing pressure support during periods of apnoea or hypopnoea and decreasing pressure support during periods of above-normal or normal ventilation. This method acts to 'break' the vicious cycle whereby hyperventilation drives the patient's $PaCO_2$ below the apnoeic threshold which in-turn leads to a new cycle of hyperventilation. By servo-ventilating short term ventilation to a target which is a fraction of a longer term ventilation, the CSR pattern is often abolished. The ventilator has sensors and methods to reliably measure patient respiratory flow in the presence of a known mask vent flow and a variable inadvertent mask leak. The ventilation measures are derived from the patient respiratory flow estimate.

Another way to abolish or ameliorate the CSR pattern is by having the patient re-breathe some fraction of their own exhaled $CO_2$. The rebreathed $CO_2$ acts to either raise the patient's $PaCO_2$ or to prevent $PaCO_2$ from falling during hyperventilatory phases. In this way it can reduce the drive to hyperventilate. A convenient way to do this is to have an actively controlled vent at the mask such as one of the embodiments previously described. In existing vented breathing systems, the vent is a fixed orifice which provides enough flow over the expected mask pressure range to adequately purge the mask of exhaled $CO_2$ over each breathing cycle. By controlling the vent orifice, the amount of $CO_2$ rebreathed by the patient can also be controlled. Such an actively controlled vent can form part of a servo-control system of a respiratory treatment apparatus.

In one example, the respiratory treatment apparatus, such as a ventilator, may implement a fixed hyperventilation threshold setting, such as in liters per minute (LPM). This setting may be set by a clinician before the start of therapy. If the patient's average measured ventilation (measured over a period such as three minutes) were to exceed the threshold, the vent may be actively controlled by the controller to reduce the flow such as by reducing its venting size such that the patient would start to re-breath a small fraction of their own $CO_2$. If the detected hyperventilation subsequently resolved, such as if the threshold is no longer exceeded, the vent could be controlled by the controller to return to a normal position.

In another alternative approach, a servo-control mechanism of the controller may continuously adjust the vent size to keep fresh gas ventilation under a pre-determined threshold. Such a servo-controlled system might utilise a PID type controller with the error signal being the degree to which ventilation was above threshold and it would output the size of the vent. The controller could also regulate the vent size so as to constrain it to be within pre-determined maximum and minimum sizes.

In another example, instead of a fixed ventilation threshold, there might be an index of ventilation instability. For example, the following indices may serve as a single measure or combined measure of ventilation instability:

a. Ventilation stability may be measured by a moving window standard-deviation of ventilation assessed by the controller;

b. A central apnoea index, a central hypopnoea index or a central apnoea-hypopnoea index as detected by the controller;

c. An apnoea-hypopnoea index (which persists despite automatic adjustment of EPAP to abolish upper airway obstruction) as detected by the controller;

d. A respiratory disturbance index, (e.g., an arousal index such as one derived from flow, $SpO_2$ and/or photoplethysmogram) as detected by the controller.

Methods for detection and automated determination of such indices may be considered in view of the discussion of PCT/AU2010/000894, filed Jul. 14, 2010, based on U.S. Provisional Patent Application No. 61/226,069 filed Jul. 16, 2009, the disclosures of which are incorporated herein by reference.

In each case, the vent orifice size may be adjusted either in step fashion or continuously so as to minimise the measure of ventilation instability. Optionally, the controlled changes to vent size could be between two sizes chosen for 'normal' breathing and "re-breathing" or it may be continuously adjustable through many sizes in a range between fixed preset limits.

Figure 17A:
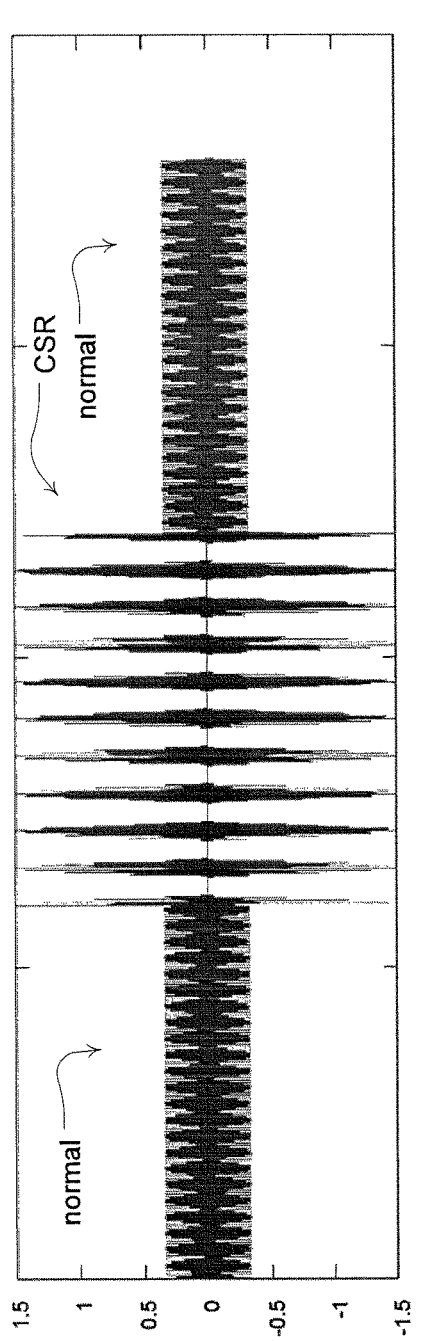
FIG. 17A is a graph illustrating a simulated Cheyne-Stokes breathing flow pattern.
Figure 17B:
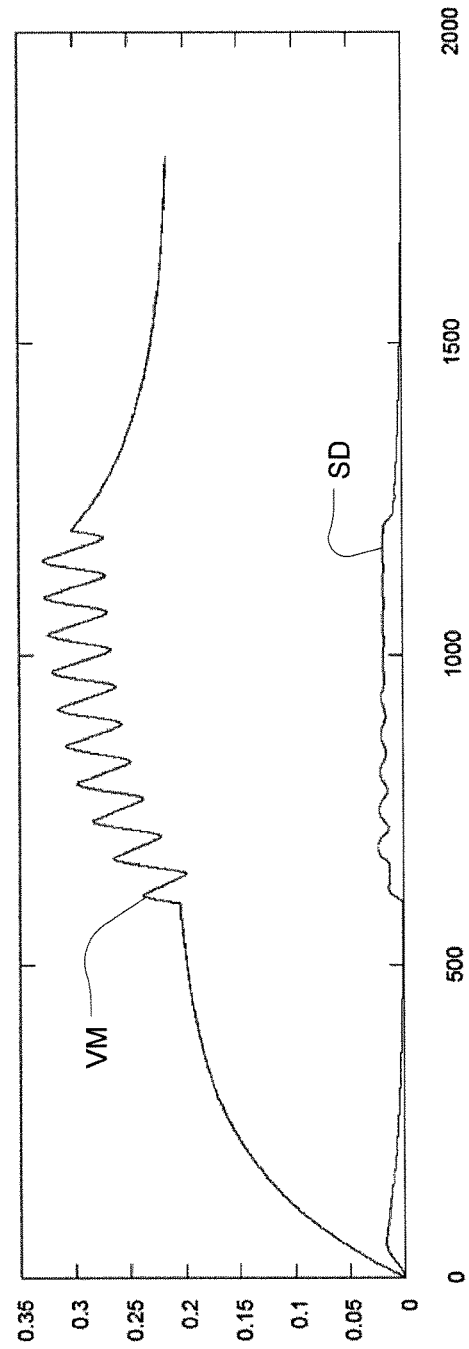
FIG. 17B is a graph of a ventilation measure and a standard deviation SD of the ventilation measure taken from the simulated patient flow of FIG. 17A.

FIGS. 17A and 17B show a simulated CSR flow pattern and some filter outputs plotted on a common time scale. The trace in FIG. 17A is a simulated patient flow with CSR breathing bracketed by two periods of normal breathing. The plot of FIG. 17B shows a ventilation measure VM (filtered with a three minute time constant) and the moving window standard deviation SD of the ventilation measure taken from the simulated patient flow of FIG. 17A. Allowing for the time it takes the filters to initialize (slow rise at the beginning), it can be seen that the ventilation during the CSR period is a) higher on-average and b) variable. The standard deviation SD trace shows that the instability in the ventilation can be measured by a moving window SD metric.

As previously mentioned, in some embodiments, the adjustable vent may be controlled by an actuator and servo-controlled to minimise a respiratory disturbance index. For example, in the plot of FIG. 17B, the determined rise in the windowed standard deviation SD of ventilation would cause the controller to reduce the vent size to increase the fraction of inspired $CO_2$. Then, when the windowed SD reduced, the controller would begin reopening or increasing the area of the vent.

In another example, the controller of the respiratory treatment apparatus may 'phase lock' to the CSR cycle. This process would involve learning the CSR cycle via a phase-locked loop and then adjusting the vent area so as to initiate a rebreathing cycle for the optimum time and with the optimum phase relationship to the CSR cycle. This would result in a lower on-average amount of rebreathing compared to a fixed level or a quasi-statically adjusted level.

In such a case, the CSR cycle is typically 60 seconds in length with a typical range of between 40 and 90 seconds. In general, the cycle length increases with worsening heart failure HF (e.g., bad $SpO_2$ reference) as does the hyperpnoea length. The cycle length does not vary quickly or substantially within a night. Therefore, once a system had phased locked to a CSR cycle, it may be possible to maintain phase lock despite a lessening degree of CSR amplitude modulation. Alternatively, if the CSR signal were to disappear altogether (i.e., normal breathing resumed) then the apparatus may re-establish a phase lock quickly based on a previously learned cycle length, hyperpnoea length and apnoea or hypopnoea length, or metrics indicative of these features.

If the patient is experiencing a CSR pattern with frank apnoeas, it may only be possible to initiate rebreathing during the hyperpnoea phase (i.e., while the patient is actually spontaneously breathing). However, once apnoeas have been abolished by the apparatus and a CSR pattern with continuous spontaneous breathing throughout the breathing cycle is detected, then it may be advantageous to vary the controlled rebreathing process to the optimum point in the cycle and for the optimal length that minimises the instability to the greatest extent. This phase delay and length of the rebreathing cycle might be pre-programmed or learned after starting at a predetermined 'best guess' starting point.

In some cases, the apparatus may simply monitor the patient over time by recording the CSR metrics previously mentioned. The apparatus may then evaluate the metrics and recommend use of a vent having a lesser venting flow if residual CSR exists. For example, the apparatus may reference an array of standard vents to choose from with particular vent flow characteristics, the apparatus may determine that a step down to a smaller vent should be implemented by issuing a warning or text instruction. Optionally, in the case of constant flow venting, it may suggest an adjustment to the vent such as a manual adjustment or insertion of an alternate mylar tab or vent aperture that will make some change to the flow characteristics of the vent.

In the above examples, the active vent control system can be run at each treatment session (e.g., each night) to provide therapy to the patient in a real time detection/response to patient needs. However, in some embodiments, it might be used on one or more nights to determine a suitable fixed vent size for the patient's subsequent therapy (e.g., by implementing a vent flow titration protocol.)

In the examples above, the active vent system and associated control system for rebreathing could be used in conjunction with adaptive servo-ventilation (e.g., ResMed AutoSet CS2). In such a combined system, the pressure control adjustment process might be used as the primary driver for suppression of CSR breathing and a rebreathing control process as previously described might supplement that process, in tandem, to damp out any residual instability (if it is detected). Alternatively, the two systems might work in concert with a master process controlling both pressure-support and rebreathing via active vent in order to more simultaneously operate to stabilise ventilation to the greatest degree. For example, such a system might implement a pressure support control-loop acting with a 'fast' time constant and a rebreathing control process acting with a 'slow' time constant.

In another example, the rebreathing control process might be the primary means of suppressing CSR breathing, with the ventilator pressure support component acting to suppress frank apnoeas via the insertion of backup breaths.

Phasic venting may be implemented with a venting protocol to treat CSR. For example, during detected hyperpnoea periods, the controller may adjust the vent to close or reduce the venting area to treat the hyperpnoea but only during detected patient expiration. In such a case, the vent area would be increased during inspiration.

Alternatively, a process of the controller may directly regulate rebreathing by calculating or estimating the quantity of flow out through the vent and controlling it to be at a desired quantity or percent.

Figure 17C:
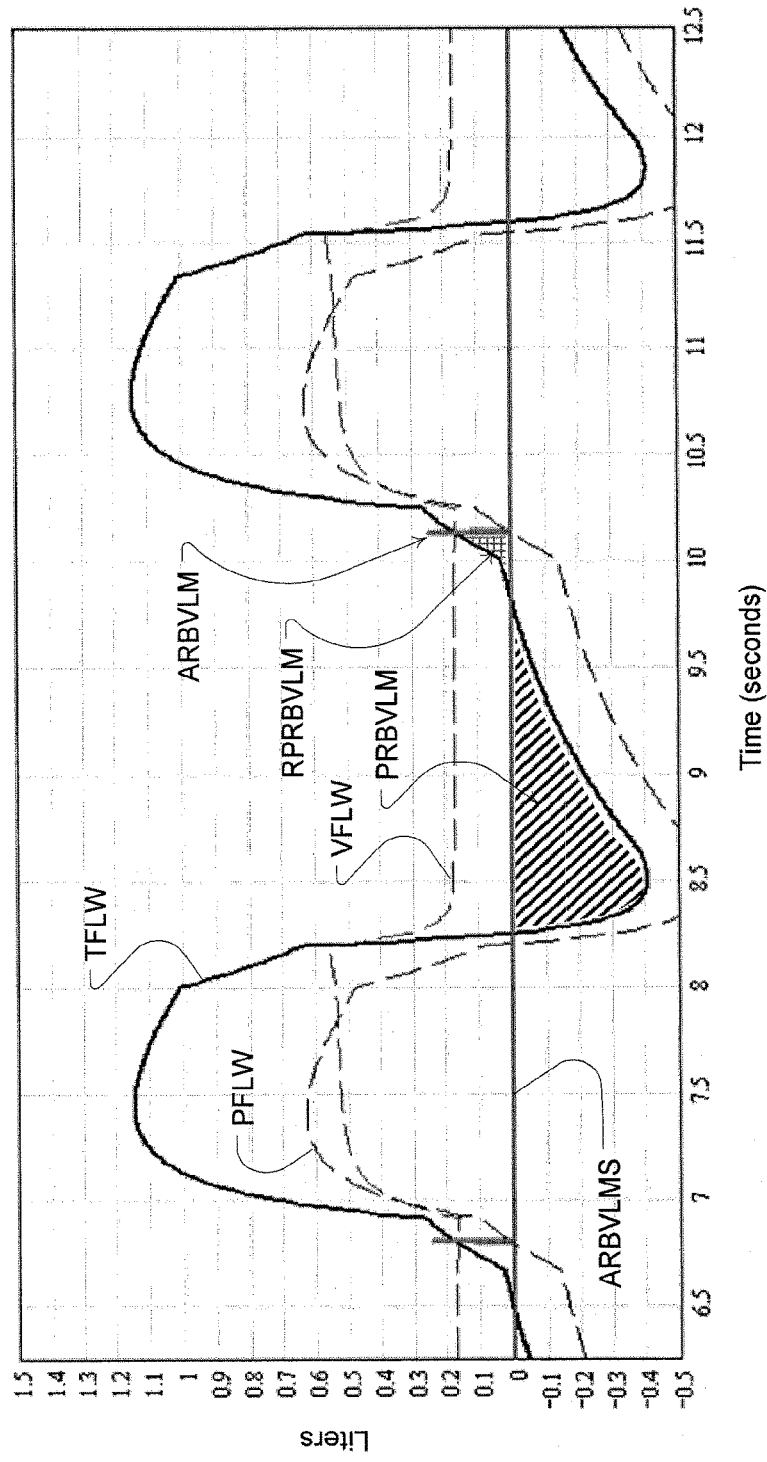
FIG. 17C is a signal graph illustrating an example calculated rebreathed volume signal suitable for controlling operations of a vent assembly of the present technology.

In one control methodology example, the presence of $CO_2$ rebreathing may be estimated using analysis of sensor measures, and the vent may be adjusted to reduce this estimate to an acceptable level. As discussed in the Background section above, if the patient's exhaled volume is still residing in the breathing circuit at the time of the next inhalation, rebreathing may occur. The magnitude of $CO_2$ rebreathing can be estimated with knowledge (or estimation) of the patient's respiratory flow and knowledge (or estimation) of current vent flow, with the intention of 'tracking' the exhaled volume remaining in the tube at next inhalation. As illustrated in FIG. 17C, this may be achieved utilizing the total flow TFLW delivered to the patient and an estimate of mask pressure. For example, the measured signal from a flow sensor within the air-delivery path of a respiratory treatment apparatus will comprise two components: an alternating component being patient respiratory flow PFLW, and a pressure-dependent bias flow being the sum of vent flow and any flow from unintentional leak (e.g., mask or mouth leak) from the breathing circuit of the respiratory treatment apparatus. The respiratory apparatus may estimate each component by a variety of methods, such as any of those described in International Patent Application No. PCT/AU2011/000950 filed on Jul. 30, 2012 and/or U.S. Pat. No. 6,659,101 filed on Jul. 10, 2001, the entire disclosures of which are incorporated herein by reference. For example, the combined leak can be modelled as a fixed size orifice, the flow through which can be predicted from the mask pressure and the orifice impedance. In this case the orifice impedance can be estimated using a relationship between long-term average (multiple breath cycles) mask pressure and long-term average total flow. Having thus estimated the orifice impedance, the total leak flow VFLW (both intentional and un-intentional leak) at any instant can be estimated. During the expiratory phase, the integral of any reverse flow back up the circuit represents a potentially re-breathable exhaled volume PRBVLM. Any of this volume remaining at the start of inspiration is actually rebreathed, which may be calculated as the potential rebreathed volume PRBVLM less the integral of estimated total leak flow VFLW minus total flow TFLW over the balance of the expiratory phase (shown in FIG. 17C at reference character RPRBVLM). The calculated difference may thus represent the actual rebreathed volume ARBVLM which may be calculated and represented each breath in an actual rebreathed volume signal ARBVLMS determined by a controller or processor.

By so doing the vent can be adjusted to reduce this estimate of the actual rebreathed volume to an acceptable level, regardless of the PEEP/EPAP value, the tidal volume, and the breathing pattern. That is, the vent can be actuated so as to open the vent or to increase the venting or venting area of the vent assembly. Any such adjustment of the vent should typically be made over a time scale many times longer than the averaging period used by the leak impedance calculation. The actuation of the vent assembly by the controller may be by a closed loop control methodology so as to servo-control the vent such that it prevents rebreathing while minimising losses. In some versions, the controller may have a set of thresholds to keep the flow of the vent in a desired range, such as a range defined by two thresholds.

For the above processes a pressure treatment therapy is generated by a respiratory treatment apparatus that also includes the venting control. However, in some embodiments a mask with a vented control may be used without a flow generator that generates a pressure treatment (e.g., a snorkel) or in some cases pressure treatment may be stopped while venting control is activated.

Figure 7:
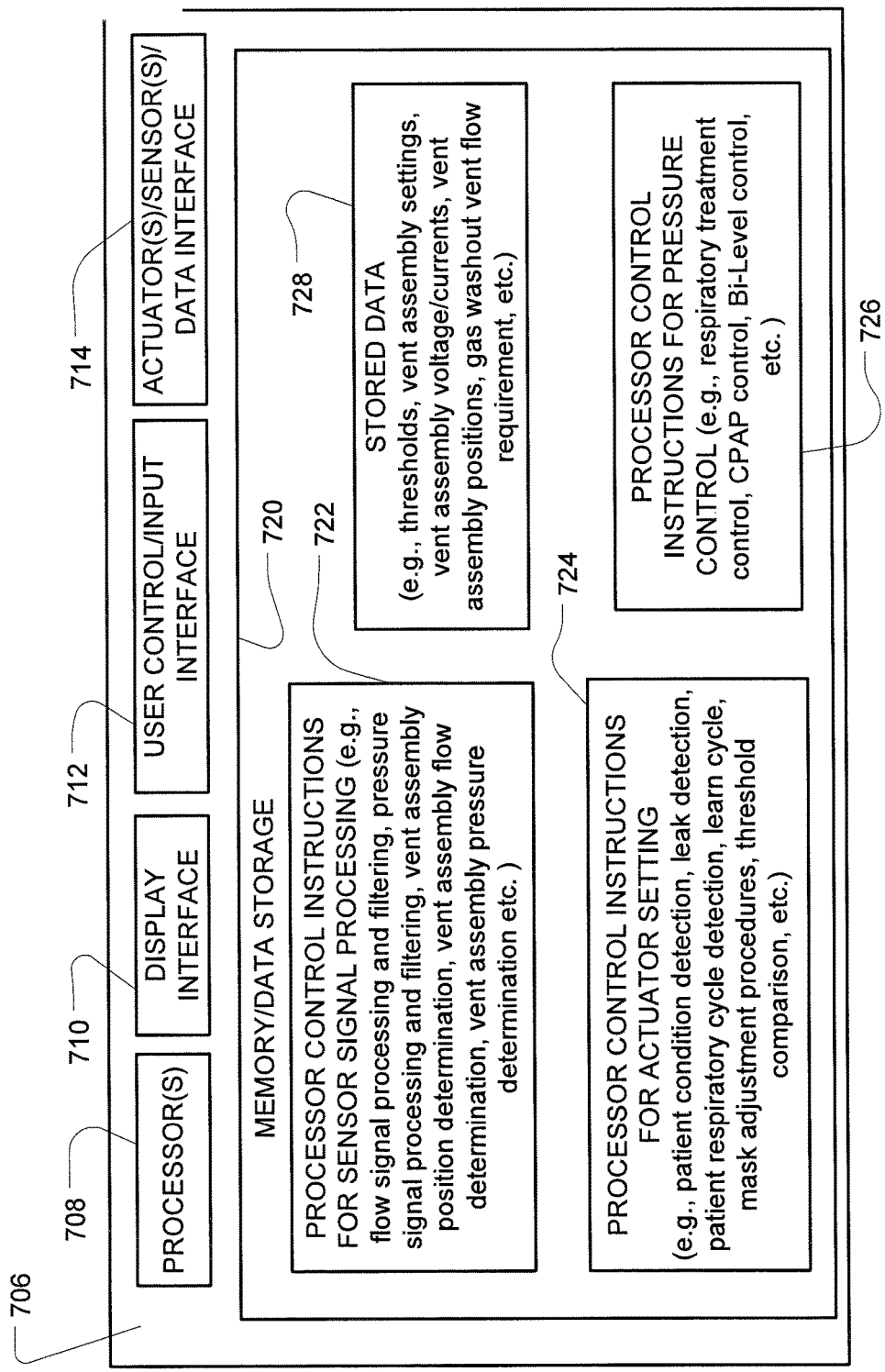
FIG. 7 is a schematic diagram showing example components of a controller suitable for implementation in some embodiments of the present technology.

An example system architecture of a controller of a respiratory treatment apparatus suitable for controlling actuation of the variable area vent assembly of the present technology is illustrated in the block diagram of FIG. 7. In the illustration, the controller 706 for a respiratory treatment apparatus may include one or more processors 708. The system may also include a display interface 710 to output event detection reports (e.g., central apnea, obstructive apnea, central hypopnea, obstructive hypopnea, etc.) or vent assembly related data (settings, vent flow vs. time plots, vent area, etc.) as described herein such as on a monitor or LCD panel. This may be used to log and/or monitor the performance or controlled changes in the vent characteristics during a treatment session. A user control/input interface 712, for example, a keyboard, touch panel, control button(s), buttons, dial, mouse etc. may also be provided to activate or modify the control methodologies described herein. The system may also include an actuator, sensor or data interface 714, such as a bus, for receiving/transmitting data such as programming instructions, pressure and flow signals, positioning signals, actuator control signals, etc. The device may also typically include memory/data storage components 720 containing control instructions of the aforementioned methodologies. These may include processor control instructions for sensor signal processing (e.g., flow and/or pressure signal processing and filtering, vent assembly position determination, vent assembly flow determination, vent assembly pressure determination, etc.) at 722. These may also include processor control instructions for control of the variable vent area vent assembly actuation/setting (e.g., patient condition detection, leak detection, patient respiratory cycle detection, learn cycle, sleep detection, mask adjustment procedures, related threshold comparisons, etc.) at 724 as previously discussed in more detail herein. These may also include processor control instructions for treatment control (e.g., respiratory treatment control, pressure adjustments, CPAP pressure control, Bi-level pressure control, or other flow generator control methodologies etc.) at 726. Finally, they may also include stored data 728 for or from the methodologies of the controller (e.g., vent assembly settings, vent assembly voltage and/or current data, vent assembly positions, gas washout flow requirements data, recorded vent flow data, etc.).

In some embodiments, these processor control instructions and data for controlling the above described methodologies may be contained in a computer readable recording medium as software for use by a general purpose computer so that the general purpose computer may serve as a specific purpose computer according to any of the methodologies discussed herein upon loading the software into the general purpose computer. Still further, the methodologies may be contained in a device or apparatus that includes integrated chips, a memory and/or other control instruction, data or information storage medium. For example, programmed instructions encompassing such detection methodologies may be coded on integrated chips in the memory of the device or apparatus to form an application specific integrated chip (ASIC). Such instructions may also or alternatively be loaded as software or firmware using an appropriate data storage medium.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

While particular embodiments of this technology have been described, it will be evident to those skilled in the art that the present technology may be embodied in other specific forms without departing from the essential characteristics thereof. The present embodiments and examples are therefore to be considered in all respects as illustrative and not restrictive, the scope of the technology being indicated by the appended claims rather than the foregoing description, and all changes which come within the meaning and range of equivalency of the claims are therefore intended to be embraced therein. It will further be understood that any reference herein to subject matter known in the field does not, unless the contrary indication appears, constitute an admission that such subject matter is commonly known by those skilled in the art to which the present technology relates.

The invention claimed is:

1. An apparatus for automated control of gas washout of a non-invasive patient interface of a respiratory treatment apparatus comprising:
   a vent assembly having a variable exhaust area defined by one or more apertures of the vent assembly, the vent assembly being (1) associated with the non-invasive patient interface to vent expiratory gas and (2) proximal to the non-invasive patient interface;
   an actuator to manipulate said one or more apertures of the vent assembly; and
   a controller, including a processor, that is coupled to the actuator and configured to operate the actuator to change the variable exhaust area of the vent assembly,
   wherein the variable exhaust area is configured to be set to a plurality of open positions, the plurality of open positions providing different vent flow areas that are adapted to provide an increase or decrease in flow rate of the expiratory gas through the variable exhaust area.

2. The apparatus of claim 1 wherein the controller is configured to switch between a treatment setting for the variable exhaust area and a comfort setting for the variable exhaust area.

3. The apparatus of claim 1 wherein the controller is configured with a user interface for input of comfort settings including a setting for the variable exhaust area, wherein the comfort setting includes one or more of a humidity setting, pressure setting, and a temperature setting.

4. The apparatus of claim 1 wherein the controller is configured to determine a measure of patient ventilation and adjust the variable exhaust area as a function of the measure of patient ventilation and the variable exhaust area is decreased if the measure of patient ventilation meets or exceeds a threshold, wherein the measure of patient ventilation comprises an instability index.

5. The apparatus of claim 4 wherein the instability index comprises at least one of a moving window standard-deviation of ventilation, a central apnoea index, a central hypopnoea index, a central apnoea-hypopnoea index, an persistent apnoea-hypopnoea index, and a respiratory disturbance index.

6. The apparatus of claim 1 wherein the controller is configured to detect a Cheyne-Stokes respiration cycle from a patient flow signal and phase-lock adjustments to the variable exhaust area to control rebreathing cycles according to the phase-lock.

7. The apparatus of claim 1 wherein the controller is further configured to control operation of a flow generator.

8. The apparatus of claim 1 wherein the controller is configured to detect a presence or absence of an unintentional leak and control the change to the exhaust area based on the detection of the presence or absence of the unintentional leak.

9. The apparatus of claim 8 wherein the controller closes the exhaust area in response to the detection of the presence of the unintentional leak.

10. The apparatus of claim 8 wherein the controller closes and opens the exhaust area in response to a continued detection of the presence of the unintentional leak.

11. The apparatus of claim 8 wherein the controller changes the exhaust area as a function of a quantification of the unintentional leak.

12. The apparatus of claim 11 wherein the controller decreases the exhaust area based on a threshold comparison of a value of the quantification.

13. The apparatus of claim 1 wherein the controller is configured to detect a sleep state and control the change to the exhaust area based on the detection of the sleep state.

14. The apparatus of claim 13 wherein the controller initiates a cyclical variation of the exhaust area in response to the detection of the sleep state.

15. The apparatus of claim 13 wherein the controller maintains an approximately constant exhaust area in response to the detection of an absence of sleep.

16. The apparatus of claim 1 wherein the controller is configured to detect a breathing condition and control the change to the exhaust area based on the detection of the breathing condition.

17. The apparatus of claim 16 wherein the detected breathing condition comprises a central apnea or central hypopnea and the controller is configured to control a decrease to the exhaust area based on the detection of the central apnea or central hypopnea.

18. The apparatus of claim 17 wherein the controller is configured to control an increase of the exhaust area based on a further detection of an absence of central apnea or central hypopnea.

19. The apparatus of claim 1 wherein the controller controls changes to the exhaust area in synchrony with detected patient respiration and the controller controls changes to the variable exhaust area as a function of any one of a measure of pressure; a measure of flow through the variable exhaust area; a measure of patient flow; or a calculation of a rebreathed volume.

20. The apparatus of claim 1 wherein the actuator comprises a motor and an induction coil coupled to a first structure and a second structure, and wherein the structures are configured to adapt a size of overlapping apertures by rotation of the first structure.

21. The apparatus of claim 1 wherein the actuator comprises one or more of a voice coil; a magnet; a pneumatic piston; a motor; or a piezo motor.

22. The apparatus of claim 1 further comprising a spring mechanism configured to return the variable exhaust area of the vent assembly to a normally open position.

23. The apparatus of claim 1 wherein the variable exhaust area is defined by overlapping apertures.

24. A system for automated control of gas washout of a non-invasive patient interface comprising:
a vent assembly having a variable exhaust area defined by one or more apertures of the vent assembly, the vent assembly being (1) attachable to the non-invasive patient interface and (2) proximal to the non-invasive patient interface; and
an actuator to manipulate an aperture of the vent assembly, the actuator configured for control by a controller to change the exhaust area of the vent assembly, wherein the variable exhaust area is configured to be set to a plurality of open positions, the plurality of open positions providing different vent flow areas that are adapted to provide an increase or decrease in flow rate of expiratory gas through the variable exhaust area.

25. The system of claim 24 wherein the actuator comprises a motor and an induction coil coupled to a first structure and a second structure, and wherein the structures are configured to change a size of overlapping apertures by rotation of the first structure.

26. The system of claim 24 wherein the actuator comprises at least one of a voice coil; a pneumatic piston; an induction coil; or a piezo motor.

27. The system of claim 24 further comprising a spring mechanism configured to return the variable exhaust area of the vent assembly to a normally open position.

28. The system of claim 24 wherein the controller is configured to detect a presence or absence of an unintentional leak and control the change to the exhaust area based on the detection of the presence or absence of the unintentional leak.

29. The system of claim 28 wherein the controller closes the exhaust area in response to the detection of the presence of the unintentional leak.

30. The system of claim 28 wherein the controller opens the exhaust area in response to the detection of the presence of the unintentional leak to lower a mask pressure to ambient pressure.

31. The system of claim 28 wherein the controller closes and opens the exhaust area in response to a continued detection of the presence of the unintentional leak.

32. The system of claim 28 wherein the controller changes the exhaust area as a function of a quantification of the unintentional leak.

33. The system of claim 32 wherein the controller decreases the exhaust area based on a threshold comparison of a value of the quantification.

34. The system of claim 24 wherein the controller is configured to detect a sleep state and control the change to the exhaust area based on the detection of the sleep state.

35. The system of claim 34 wherein the controller initiates a cyclical variation of the exhaust area as a function of a detected sleep state.

36. The system of claim 34 wherein the controller maintains an approximately constant exhaust area in response to the detection of an absence of sleep.

37. The system of claim 24 wherein the controller is configured to detect a breathing condition and control the change to the exhaust area based on the detection of the breathing condition.

38. The system of claim 37 wherein the detected breathing condition comprises a central apnea or central hypopnea and the controller is configured to control a decrease to the exhaust area based on the detection of the central apnea or central hypopnea.

39. The system of claim 38 wherein the controller is configured to control an increase of the exhaust area based on a further detection of an absence of central apnea or central hypopnea.

40. The system of claim 24 wherein the controller controls changes to the exhaust area as a function of a measure of patient flow.

41. The system of claim 24 wherein the controller controls changes to the exhaust area as a function of a calculation of a rebreathed volume.

42. The system of claim 24 wherein the controller controls changes to the exhaust area in synchrony with detected patient respiration to permit a vent flow of the exhaust area to mirror patient flow.

43. The system of claim 24 wherein the controller is configured to switch between a treatment setting for the variable exhaust area and a comfort setting for the variable exhaust area.

44. The system of claim 24 wherein the controller is configured with a user interface for input of comfort settings including a setting for the variable exhaust area, wherein the comfort setting includes one or more of a humidity setting, pressure setting, and a temperature setting.

45. The system of claim 24 wherein the controller is configured to determine a measure of patient ventilation and adjust the variable exhaust area as a function of the measure of patient ventilation, wherein the measure of patient ventilation comprises an instability index.

46. The system of claim 45 wherein the variable exhaust area is decreased if the measure of patient ventilation meets or exceeds a threshold.

47. The system of claim 45 wherein the instability index comprises at least one of a moving window standard-deviation of ventilation, a central apnoea index, a central hypopnoea index, a central apnoea-hypopnoea index, an persistent apnoea-hypopnoea index, and a respiratory disturbance index.

48. The system of claim 24 wherein the controller is configured to detect a Cheyne-Stokes respiration cycle from a patient flow signal and phase-lock adjustments to the variable exhaust area to control rebreathing cycles according to the phase-lock.

49. The system of claim 24 wherein the variable exhaust area is defined by overlapping apertures.

* * * * *